(12) United States Patent
Newman

(10) Patent No.: US 7,571,054 B2
(45) Date of Patent: Aug. 4, 2009

(54) METHOD AND SYSTEM FOR INTERPRETING TUBING DATA

(75) Inventor: Frederic M. Newman, Midland, TX (US)

(73) Assignee: Key Energy Services, Inc., Houston, TX (US)

(*) Notice: Subject to any disclaimer, the term of this patent is extended or adjusted under 35 U.S.C. 154(b) by 111 days.

(21) Appl. No.: 11/690,904

(22) Filed: Mar. 26, 2007

(65) Prior Publication Data

US 2008/0035334 A1 Feb. 14, 2008

Related U.S. Application Data

(60) Provisional application No. 60/786,252, filed on Mar. 27, 2006, provisional application No. 60/786,272, filed on Mar. 27, 2006, provisional application No. 60/786,273, filed on Mar. 27, 2006.

(51) Int. Cl.
*G06F 19/00* (2006.01)
(52) U.S. Cl. .......................... 702/6; 235/449
(58) Field of Classification Search .................. 702/6, 702/9, 14, 182–185, 188; 235/375, 449
See application file for complete search history.

(56) References Cited

U.S. PATENT DOCUMENTS

| | | | |
|---|---|---|---|
| 4,393,485 A | 7/1983 | Redden | |
| 4,545,017 A | 10/1985 | Richardson | 702/9 |
| 4,660,419 A | 4/1987 | Derkacs et al. | 73/622 |
| 4,700,142 A | 10/1987 | Kuckes | 340/853.5 |
| 4,779,201 A | 10/1988 | Iizuka et al. | 702/10 |
| 4,851,773 A | 7/1989 | Rothstein | 324/220 |
| 5,043,663 A | 8/1991 | Lam | 324/242 |
| 5,051,962 A | 9/1991 | Eaton | 367/33 |
| 5,193,628 A | 3/1993 | Hill et al. | 175/45 |
| 5,218,301 A | 6/1993 | Kuckes | 324/346 |
| 5,237,539 A | 8/1993 | Selman | 367/69 |

(Continued)

FOREIGN PATENT DOCUMENTS

WO   WO 2004/074808 A2   9/2004

OTHER PUBLICATIONS

PCT/US07/64894 International Search Report and the Written Opinion of the International Searching Authority, or the Declaration—Date of mailing Feb. 7, 2008.

(Continued)

*Primary Examiner*—Edward Raymond
(74) *Attorney, Agent, or Firm*—King & Spalding LLP

(57) ABSTRACT

An instrument, such as a wall-thickness, rod-wear, or pitting sensor, can monitor tubing as a field service crew extracts the tubing from an oil well or inserts the tubing into the well. A computer-based system can process data from the instrument to evaluate the validity of the data. Validating the data can comprise determining whether any features, structures, or patterns present in the data correlate with actual tubing defects or were caused by a condition unrelated to tubing quality, such as signal noise. The computer-based system can also analyze the data to deduce information about the performance of the well or to determine the well's operating state or status. For example, the data analysis can determine whether the well's fluids have a chemical condition that should be treated or whether a detrimental harmonic oscillation has been occurring in the well's mechanical pumping system.

27 Claims, 31 Drawing Sheets

U.S. PATENT DOCUMENTS

| | | | |
|---|---|---|---|
| 5,278,549 A | 1/1994 | Crawford | |
| 5,491,668 A | 2/1996 | Priest | 367/35 |
| 5,548,900 A | 8/1996 | Hunt-Grubbe | 33/302 |
| 5,626,192 A | 5/1997 | Connell et al. | 166/255.1 |
| 5,678,643 A | 10/1997 | Robbins et al. | 175/45 |
| 5,947,213 A | 9/1999 | Angle et al. | 175/24 |
| 6,021,093 A | 2/2000 | Birchak | |
| 6,079,490 A | 6/2000 | Newman | 166/77.51 |
| 6,209,639 B1 | 4/2001 | Newman | |
| 6,285,955 B1 | 9/2001 | Goldwasser | 702/6 |
| 6,316,937 B1 | 11/2001 | Edens | 324/220 |
| 6,347,292 B1 | 2/2002 | Denny et al. | 702/188 |
| 6,359,434 B1 | 3/2002 | Winslow et al. | 324/220 |
| 6,377,189 B1 | 4/2002 | Newman | 340/854.6 |
| 6,411,084 B1 | 6/2002 | Yoo | 324/221 |
| 6,571,634 B1 * | 6/2003 | Bazarov et al. | 73/623 |
| 6,728,638 B2 | 4/2004 | Newman | 702/5 |
| 6,760,665 B1 | 7/2004 | Francis | 702/6 |
| 6,896,056 B2 | 5/2005 | Mendez et al. | 166/254.2 |
| 7,006,920 B2 | 2/2006 | Newman | |
| 2004/0226712 A1 | 11/2004 | Hood et al. | 166/66 |
| 2005/0194182 A1 | 9/2005 | Rodney et al. | 175/24 |
| 2005/0267686 A1 | 12/2005 | Ward | 702/6 |
| 2006/0047430 A1 | 3/2006 | Edwards | 702/6 |

OTHER PUBLICATIONS

PCT/US07/64964 International Search Report and Written Opinion of the International Searching Authority, or Declaration—Date of mailing Feb. 22, 2008.

PCT/US07/64894 International Search Report and Written Opinion of the International Searching Authority, or Declaration—Date of mailing Feb. 7, 2008.

PCT/US07/65032 International Search Report and Written Opionion of the International Searching Authority, or Declaration—Date of mailing Jul. 2, 2008.

PCT/US07/64846 International Search Report and Written Opinion of the International Searching Authority, or Declaration—Date of mailing Dec. 12, 2007.

* cited by examiner

| Sensor Data Point Counter (S) | Data Value | Position Counter (D) | Depth (in feet) |
|---|---|---|---|
| 1 | 0.1 | 1 | 2 |
| 2 | 0.2 | 2 | 7 |
| 3 | 0.13 | 3 | 15 |
| 4 | 0.15 | 4 | 19 |
| 5 | 0.2 | 5 | 25 |
| 6 | 4.8 | 6 | 30 |
| 7 | 0.2 | 7 | 33 |
| 8 | 0.15 | 8 | 36 |
| 9 | 0.3 | 9 | 39 |
| 10 | 0.4 | 10 | 42 |
| 11 | 0.2 | 11 | 45 |
| 12 | 0.3 | 12 | 48 |
| 13 | 0.1 | 13 | 51 |
| 14 | 0.15 | 14 | 54 |
| 15 | 0.25 | 15 | 57 |
| 16 | 4.3 | 16 | 60 |
| 17 | 0.2 | 17 | 66 |
| 18 | 0.4 | 18 | 74 |
| 19 | 0.25 | 19 | 80 |
| 20 | 0.15 | 20 | 83 |

*Fig. 22B*

METHOD AND SYSTEM FOR INTERPRETING TUBING DATA

This application claims benefit of U.S. Provisional Application Ser. Nos. 60/786,252, filed on Mar. 27, 2006; 60/786,272, filed on Mar. 27, 2006; and 60/786,273, fled on Mar. 27, 2006.

FIELD OF THE INVENTION

The present invention relates to processing data describing a tube associated with an oil well and more specifically to inferring information, such as a condition of the well or the validity of the data, based on processing the data.

BACKGROUND

After drilling a hole through a subsurface formation and determining that the formation can yield an economically sufficient amount of oil or gas, a crew completes the well. During drilling, completion, and production maintenance, personnel routinely insert and/or extract devices such as tubing, tubes, pipes, rods, hollow cylinders, casing, conduit, collars, and duct into the well. For example, a service crew may use a workover or service rig to extract a string of tubing and sucker rods from a well that has been producing petroleum. The crew may inspect the extracted tubing and evaluate whether one or more sections of that tubing should be replaced due physical wear, thinning of the tubing wall, chemical attack, pitting, or another defect. The crew typically replaces sections that exhibit an unacceptable level of wear and notes other sections that are beginning to show wear and may need replacement at a subsequent service call.

As an alternative to manually inspecting tubing, the service crew may employ an instrument to evaluate the tubing as the tubing is extracted from and/or inserted into the well. The instrument typically remains stationary at the wellhead, and the workover rig moves the tubing through the installment's measurement zone.

The instrument typical measures pitting and wall thickness, and can also identity cracks in the tubing wall. Radiation, field strength (electrical, electromagnetic, or magnetic), sonic/ultrasonic signals, and/or pressure differential may interrogate the tubing to evaluate these wear parameters. The instrument typically produces a raw analog signal and outputs a sampled or digital version of that analog signal.

The instrument typically stimulates a section of the tubing using a field, radiation, or pressure and detects the tubing's interaction with or response to the stimulus. An element, such as a transducer, converts the response into an analog electrical signal. For example, the instrument may create a magnetic field into which the tubing is disposed, and the transducer may detect changes or perturbations in the field resulting from the presence of the tubing and any anomalies of that tubing.

The analog electrical signal output by the transducer can have an arbitrary or essentially unlimited number of states or measurement possibilities. Rather than having two discrete or binary levels, typical transducers produce signals that can assume any of numerous levels or values. As tubing passes through the measurement field of the instrument, the analog transducer signal varies in response to variations and anomalies in the wall of the moving tubing.

The transducer and its associated electronics may have a dampened or lagging response that tends to reduce the responsiveness of the signal to tubing wall variations and/or noise. In other words, the instrument may acquire and process analog signals in a manner that steadies or stabilizes those analog signals. In typical conventional instruments, the analog processing remains fixed. Any damping or filtering of those signals is generally constant and inflexible.

The instrument also typically comprises a system, such as an analog-to-digital converter ("ADC"), that converts the analog transducer signal into one or more digital signals suited for reception and display by a computer. In conventional instruments, those digital signals typically provide a "snapshot" of the transducer signal. The ADC typically outputs a number, or set of a numbers, that represents or describes the analog transducer signal at a certain instant or moment in time. Because the analog transducer signal describes the section of tubing that is in the instrument's measurement zone, the digital signal is effectively a sample or a snapshot of a parameter-of-interest of that tubing section.

The analog-to-digital conversion typically occurs on a fixed-time basis, for example one, eight, or sixteen times per second. That is, conventional instruments usually acquire measurement samples at a predetermined rate or on a fixed time interval. Meanwhile, the speed of the tubing passing through the measurement zone may fluctuate or change erratically. The operator may change the extraction speed in an unrepeatable fashion or in a manner not known in advance, a priori, or before the speed-change event.

The instrument may output a series of samples or digital snapshots with each sample separated by a tubing length not readily determined using conventional technology. The separation between samples may be a millimeter, a centimeter, or a meter of tubing length, for example. Distance between samples may vary, fluctuate, or change erratically as the operator changes the tubing speed. Moreover, sample data may blur or become smeared when the tubing is moving rapidly. Consequently, fixing the time interval between each snapshot and allowing the tubing speed to vary between snapshots, as occurs in most conventional instruments, can produce data that is difficult to interpret or fails to adequately characterize the tubing.

Another shortcoming of conventional instruments is that they generally provide an insufficient or limited level of processing of the digital samples. When the tubing is moving slowly through the instrument's measurement zone or is stationary, an operator may incorrectly interpret variation in the digital samples as a wall defect; however, the variation may actually result from an extraneous effect or signal noise. At slow tubing speeds, signal spikes due to noise or a random event can be mistaken for a defective tubing condition.

Meanwhile, when the tubing is moving quickly through the measurement zone, the tubing motion may blur or smooth signal spikes that are actually due to tubing defects, thereby hiding those defects from operator observation. That is, with conventional instruments, high-speed tubing motion may mask or obscure tubing wall defects. This phenomenon can be likened to the image blurring that can occur when a person takes a photograph of a fast moving car. Conventional technologies often fail to differentiate between signal features that indicate the presence of valid tubing defects and other signal features caused by phenomena unrelated to tubing defects. An observer may struggle to determine with confidence whether actual tubing defects are associated with signal anomalies, for example.

Beyond the limitations associated with validating tubing data, conventional instrumentation technologies typically provide little or no capabilities for data interpretation. A well may have a chemical condition that causes tubing corrosion or that negatively impacts production. The sucker rods may exhibit harmonic oscillations that cause premature tubing wear, also inhibiting production. Identifying these or other well conditions is generally difficult using conventional techniques for presentation and manual review of tubing data.

To address these representative deficiencies in the art, an improved capability for processing data is needed, for example in a petroleum application wherein the data is collected from tubing that has been disposed in an oil well. A need also exists for a method to determine whether structures or features in the data are valid and/or indicate the presence of a tubing defect. A further need exists for a capability to interpret tubing data so as to deduce from that data the operational state of the well. Yet another need exists for a computer-based method of identifying and diagnosing well problems based on scanning tubing that has been removed from the well. A capability addressing one or more of these needs would promote more effective or more profitable well operation.

SUMMARY OF THE INVENTION

The present invention supports deducing information about an oil well based on evaluating an item, such as a piece of tubing or a rod, in connection with placing the item into an oil well or removing the item from the well. Evaluating the item can comprise sensing, scanning, monitoring, inspecting, assessing, or detecting a parameter, characteristic, or property of the item.

In one aspect of the present invention, an instrument, scanner, or sensor can monitor tubing, tubes, pipes, rods, hollow cylinders, casing, conduit, collars, or duct near a wellhead of the oil well. The instrument can comprise a wall-thickness, rod-wear, collar locating, crack, imaging, or pitting sensor, for example. As a field service crew extracts tubing from the oil well or inserts the tubing into the well, the instrument can evaluate the tubing for defects, integrity, wear, fitness for continued service, or anomalous conditions. The instrument can provide tubing information in a digital format for example as digital data, one or more numbers, samples, or snapshots. A computer-implemented method can process the tubing data to evaluate whether one or more components of the data is valid, credible, or erroneous or to assign a confidence indicator to the data. For example, validating the data can comprise determining whether any features, structures, or patterns present in the data correlate with actual tubing defects or were caused by a condition unrelated to tubing qualify, such as signal noise or rig speed. The computer-implemented method can also analyze the data to deduce information about the performance of the well or to determine the well's operating state, status, or condition. For example, the data analysis can determine whether the well's fluids have a chemical condition that should be treated or whether a detrimental harmonic oscillation has been occurring in the well's mechanical pumping system. Moreover, the product of the data analysis can comprise a data interpretation, an identification of a data inconsistency, an inference, a deduction, a diagnosis of the well, or a recommended procedure for addressing an identified problem, to name a few possibilities.

In another aspect, the present invention provides a method for interpreting tubing data. The method includes the steps of scanning a plurality of tubing segments with a tubing scanner to produce tubing segment scan data, wherein the scanner includes at least one sensor. The scan data for the segment is correlated with the positional data from an encoder, and the rod wear data is analyzed to identify rod wear patterns. In one embodiment the tubing scanner includes a rod-wear sensor. In another, the tubing scanner includes a pitting sensor. The method may also include the use of pattern recognition software, which may employ Fourier transform processing to identify features that repeat at regular depth intervals. Other embodiments may process the data using genetic algorithm, fractal mathematics, artificial intelligence, adaptive filtering, Kalman filtering, least squares analysis, partial least squares analysis, stochastic filtering, statistical pattern recognition, linear algorithm, or linear programming. The pattern recognition software may flag regions having significant pitting without significant rod wear, or it may flag regions having significant rod wear without significant pitting.

The discussion of processing tubing data presented in this summary is for illustrative purposes only. Various aspects of the present invention may be more clearly understood and appreciated from a review of the following detailed description of the disclosed embodiments and by reference to the drawings and any claims that may follow. Moreover, other aspects, systems, methods, features, advantages, and objects of the present invention will become apparent to one with skill in the art upon examination of the following drawings and detailed description. It is intended that all such aspects, systems, methods, features, advantages, and objects are to be included within this description, are to be within the scope of the present invention, and are to be protected by any accompanying claims.

BRIEF DESCRIPTION OF THE DRAWINGS

FIG. 3, are a flowchart of an exemplary process for obtaining information about tubing that is being inserted into or extracted from an oil well and for analyzing that information in accordance with an embodiment of the present invention.

FIG. 5, are illustrations of exemplary well conditions associated with rod wear in accordance with an embodiment of the present invention.

FIG. 8, are a flowchart of an exemplary method for processing tubing data to validate and interpret the data in accordance with an embodiment of the present invention.

FIG. 9, are a flowchart of an exemplary process for obtaining information about tubing that is being inserted into or extracted from an oil well in accordance with an embodiment of the present invention.

FIG. 5, are a graphical plot and an accompanying table of exemplary raw and filtered data samples in accordance with an embodiment of the present invention.

FIG. 13, are a graphical plot and an accompanying table of tubing data filtered with an exemplary adaptive filter in accordance with an embodiment of the present invention.

FIGS. 22, 22A, and 22B are exemplary charts and data tables displaying the steps for overlaying the associated depth data on the analysis data chart in accordance with one exemplary embodiment of the present invention;

Figure 1:
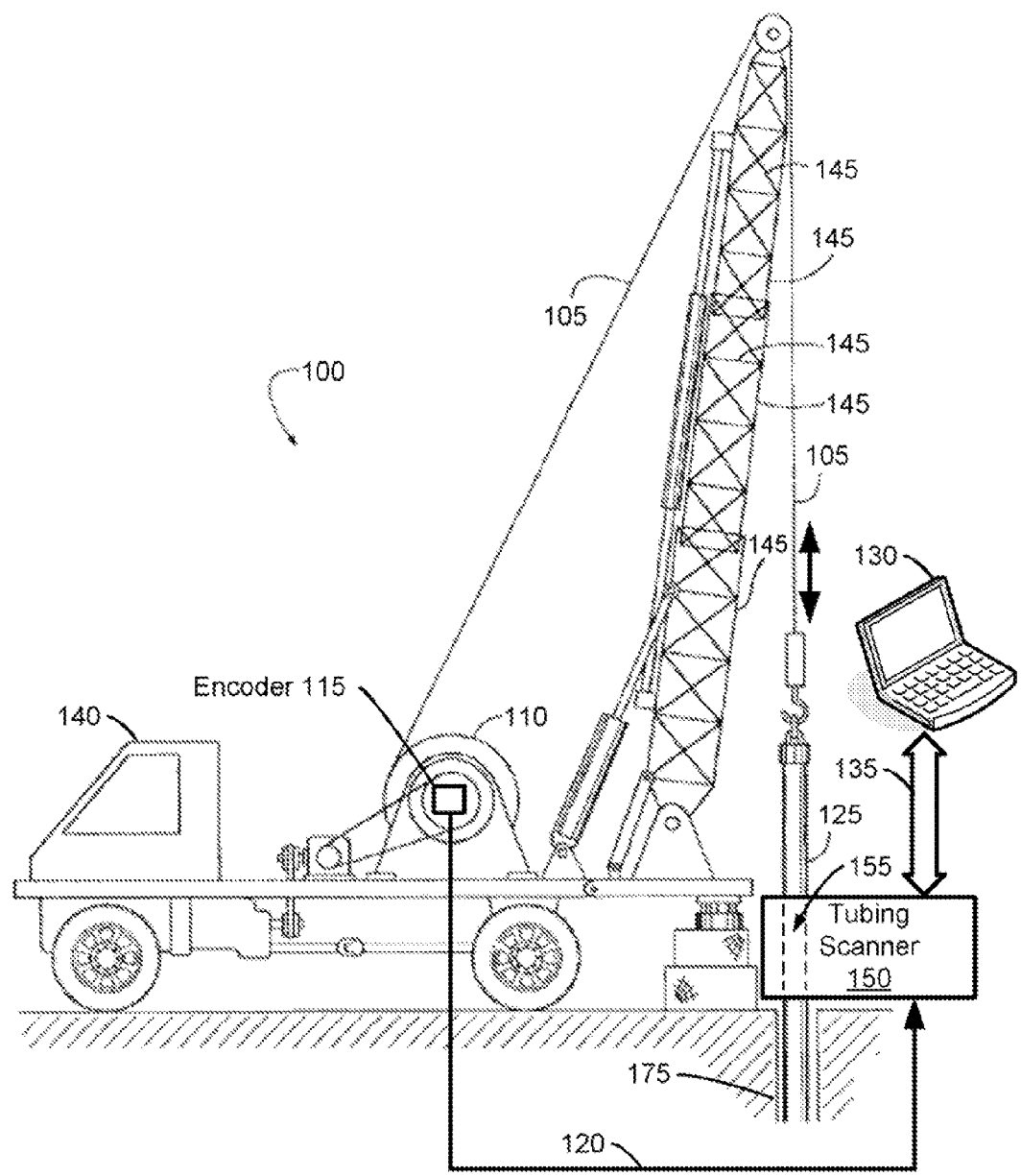
FIG. 1 is an illustration of an exemplary system for servicing an oil well that scans tubing as the tubing is extracted from or inserted into the well in accordance with an embodiment of the present invention.

Many aspects of the invention can be better understood with reference to the above drawings. The components in the drawings are not necessarily to scale, emphasis instead being placed upon clearly illustrating the principles of exemplary embodiments of the present invention. Moreover, in the drawings, reference numerals designate like or corresponding, but not necessarily identical, elements throughout the several views.

DETAILED DESCRIPTION OF EXEMPLARY EMBODIMENTS

To more adequately describe the present invention, the Detailed Description has been broken up into three sections. In Section I, the present invention supports processing information or data that describes or characterizes a tubing parameter, such as pitting, wall thickness, wall cracks, or some other indication of tubing quality or integrity. Processing the tubing data can comprise validating and/or interpreting the data. A validation procedure can evaluate whether the data is indicative of an actual tubing defect. An interpretive method can identify and/or diagnosis well conditions, such as a chemical problem or a detrimental harmonic oscillation of a reciprocating sucker rod.

In Section II, the present invention supports processing information or data that describes or characterizes a tubing parameter, such as pitting, wall thickness, wall cracks, or some other indication of tubing quality or integrity. Processing tubing data can enhance the utility, usefulness, or fidelity of the data, for example helping determine whether a piece of tubing remains fit for continued service. Thus, an oilfield service crew can make efficient, accurate, or sound evaluations of how much life, if any, remains in each joint of tubing in a string of tubing.

In Section III, the present invention supports methods for retrieving and displaying tubing analysis data with corresponding depth data associated with the tubing analysis data from tubing sections retrieved or inserted into an oil well to improve the ability of an oilfield service crew to determine problems with the well or tubing and determine if the data provided in the analysis scan does not make sense. Providing consistent reliable analysis data and displaying it in a consistent and easy to understand manner will help an oilfield service crew can make more efficient, accurate, and sound evaluations of the well and the tubing, collars and sucker rods used in the operation of the well.

Figure 2:
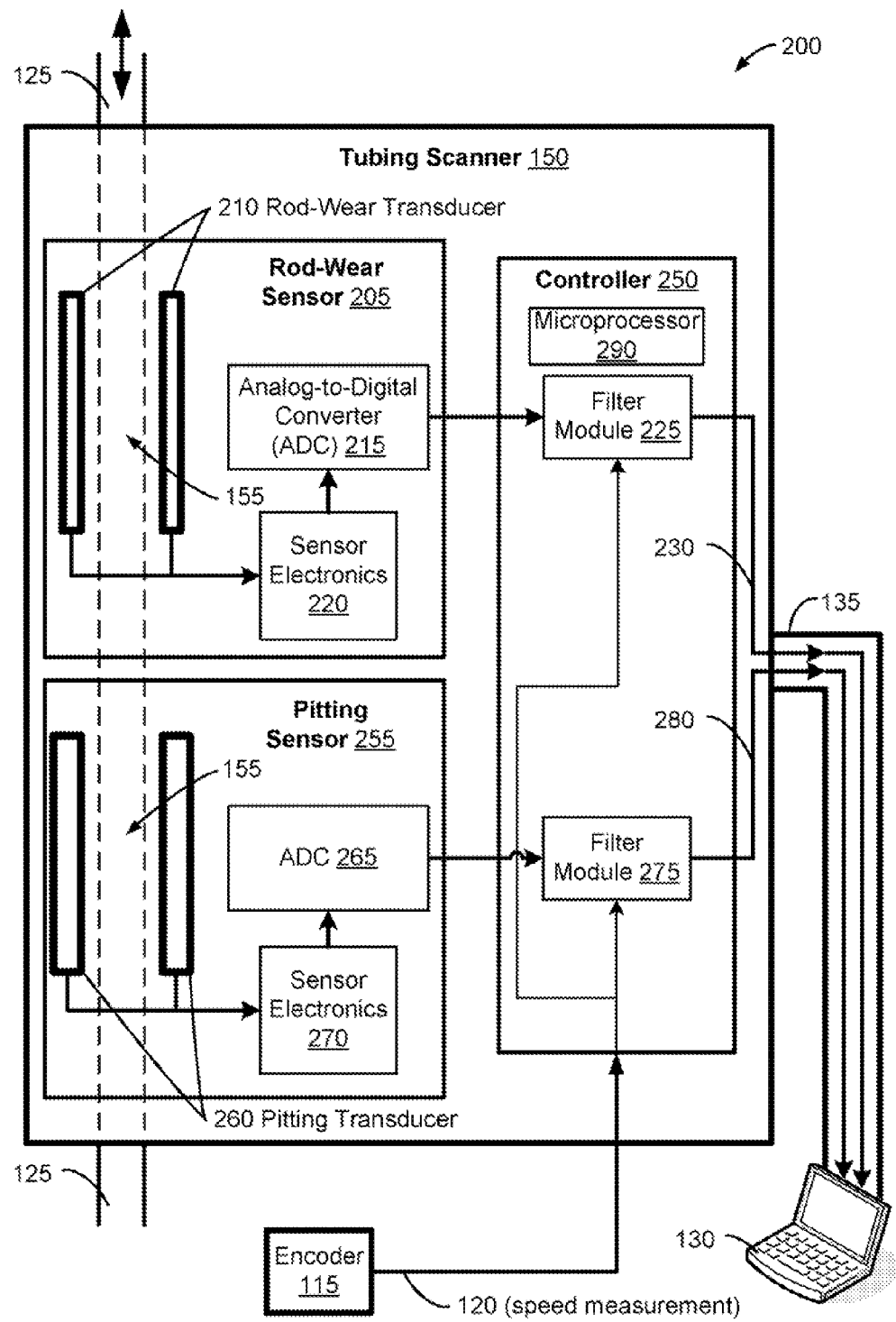
FIG. 2 is a functional block diagram of an exemplary system for scanning tubing that is being inserted into or extracted from an oil well in accordance with an embodiment of the present invention.
Figure 3A:
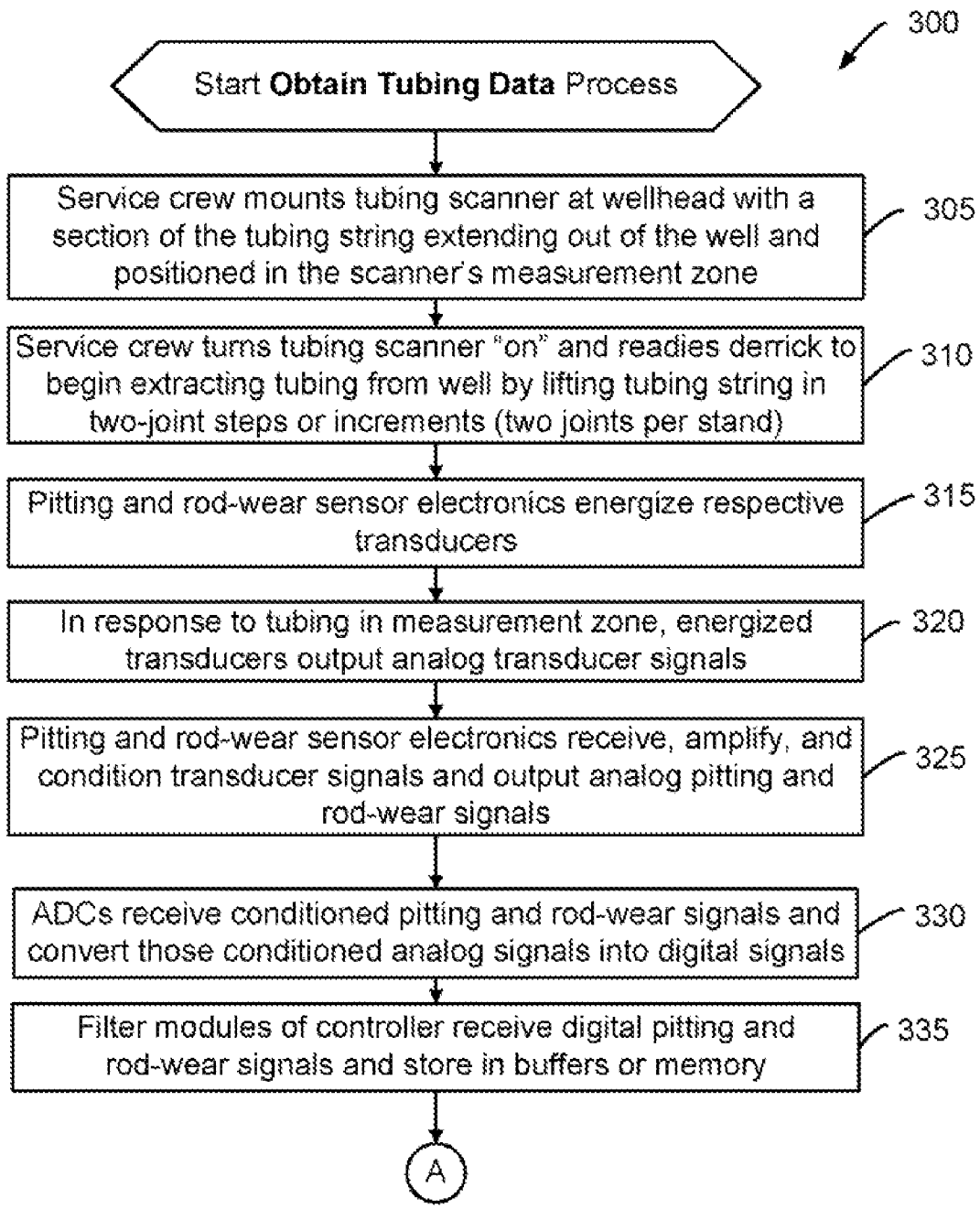
FIGS. 3A and 3B, collectively
Figure 3B:
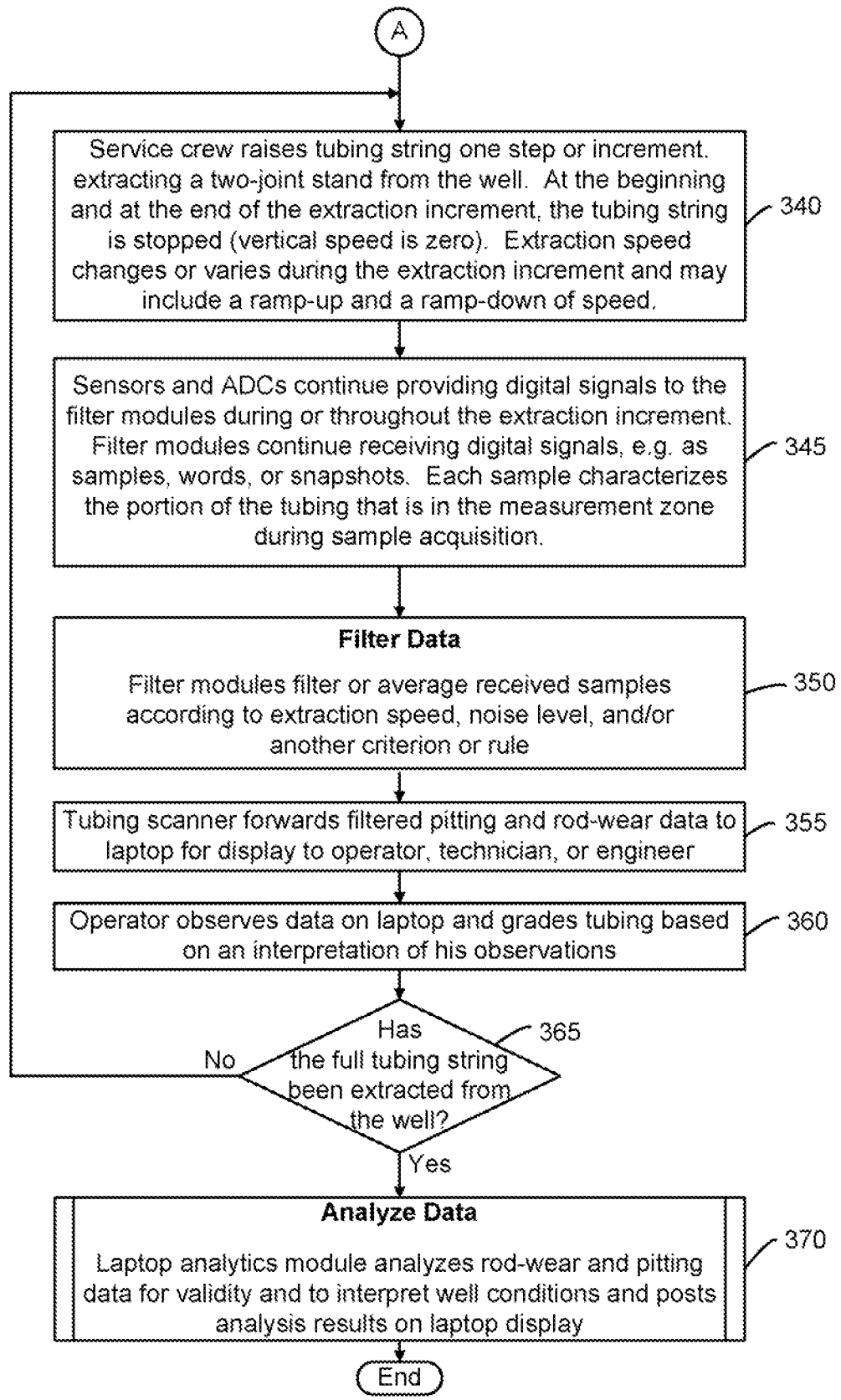
Figure 4:
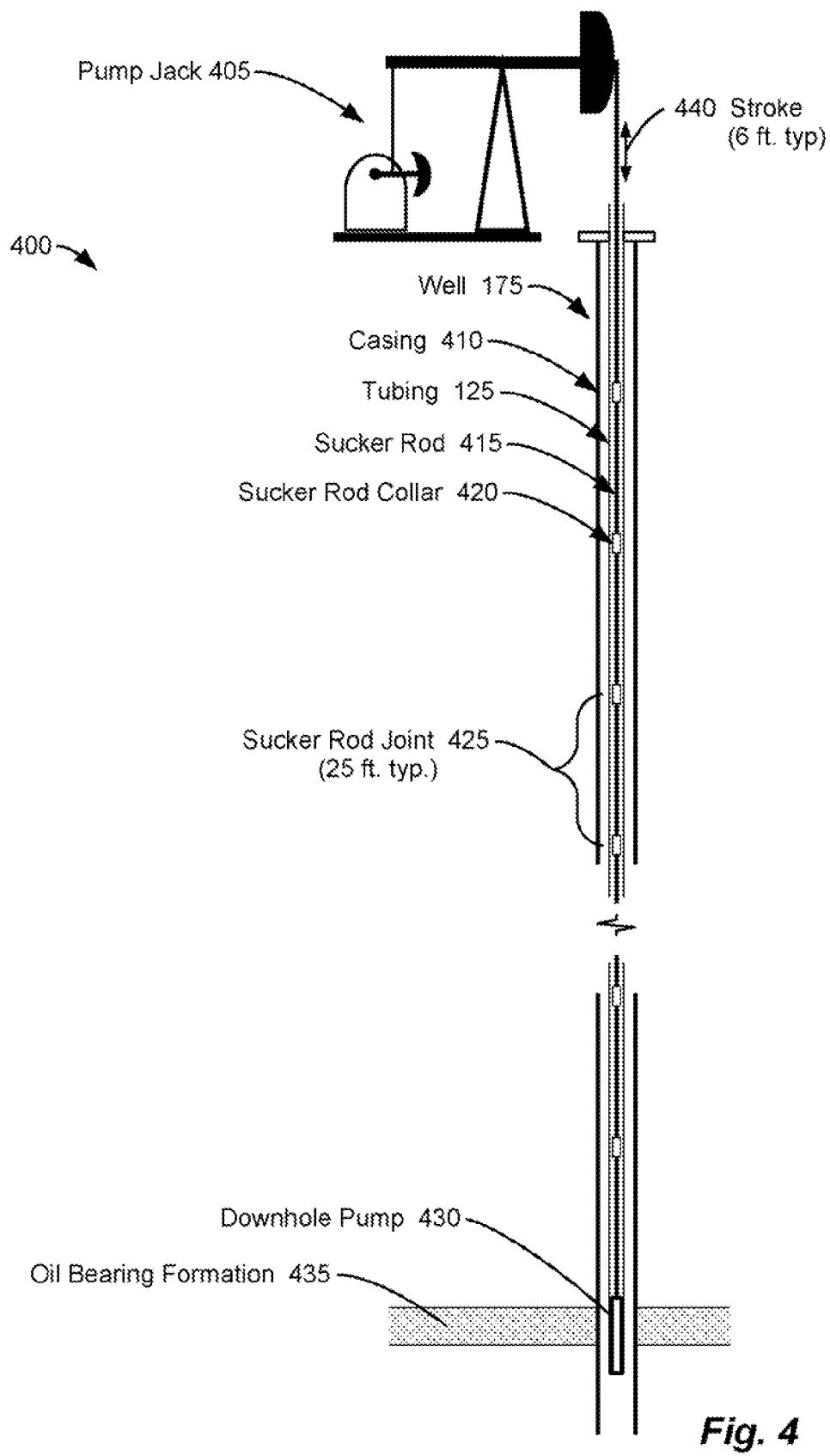
FIG. 4 is an illustration of an exemplary system for obtaining hydrocarbons from an oil well in accordance with an embodiment of the present invention.
Figure 6:
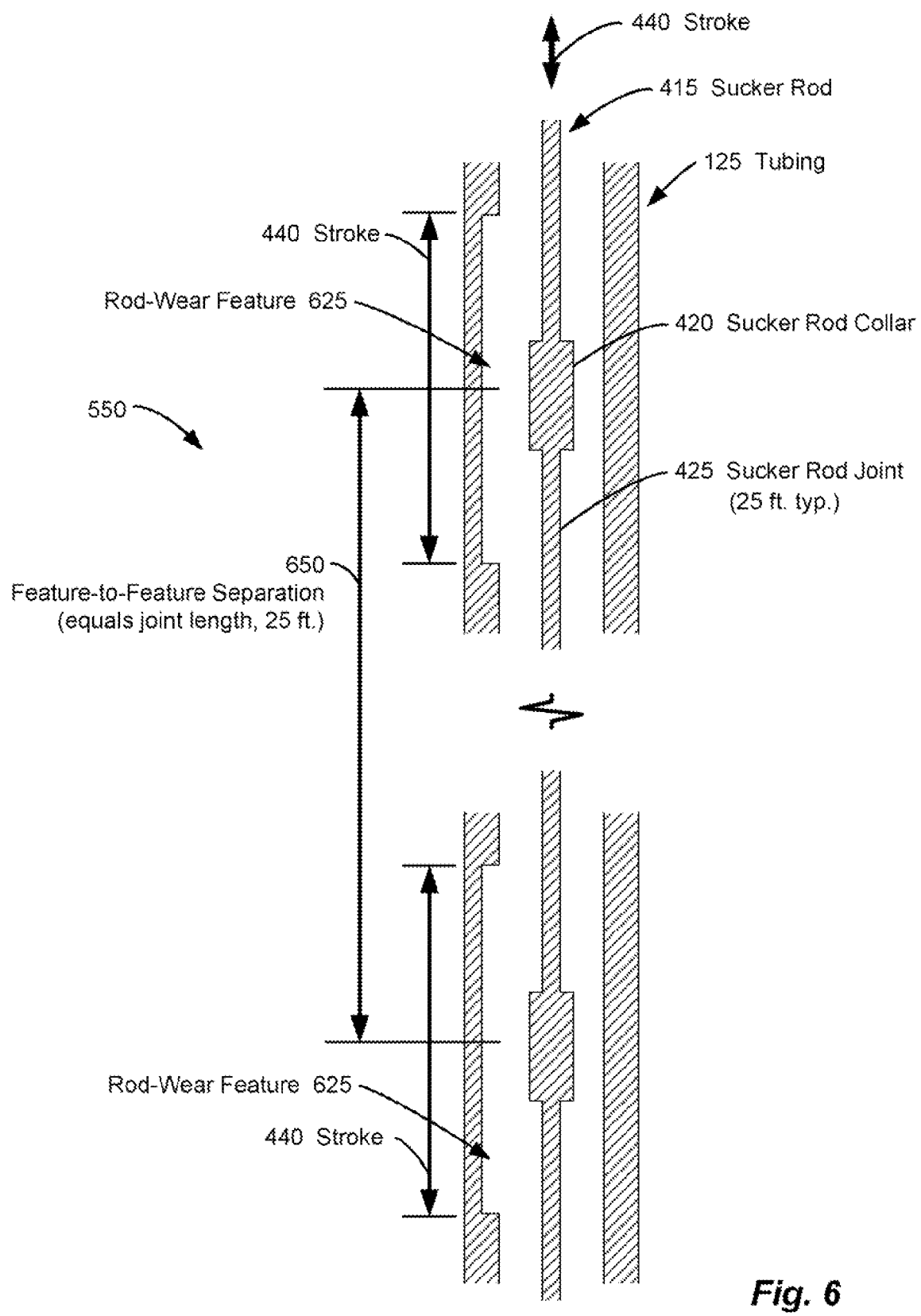
FIG. 6 is an illustration of an exemplary rod-wear pattern in accordance with an embodiment of the present invention.
Figure 7:
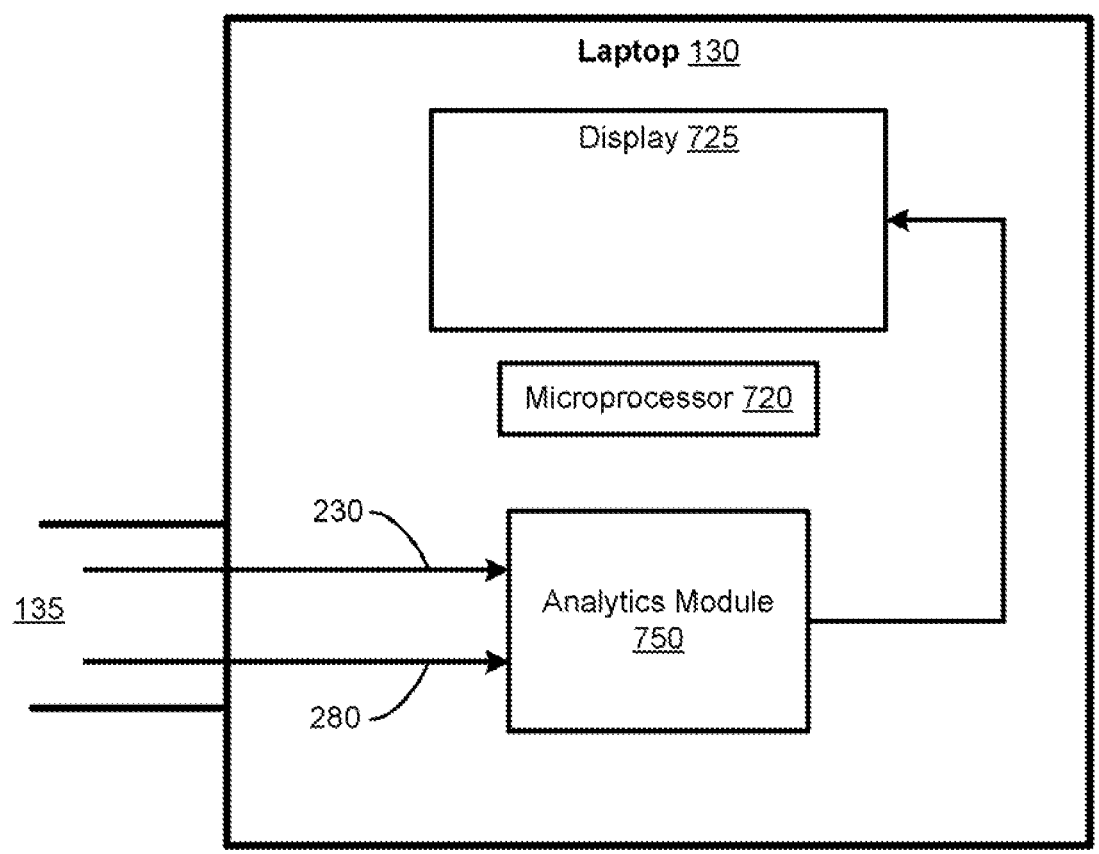
FIG. 7 is a functional block; diagram of an exemplary computer system for analyzing and displaying tubing data in accordance with an embodiment of the present invention.

The methods and systems of the present invention will now be described more fully hereinafter with reference to FIGS. 1-24, which show representative embodiments of the present invention. FIG. 1 depicts a workover rig moving tubing through a tubing scanner in a representative operating environment for an embodiment the present invention. FIGS. 2 and 7 provide block diagrams of an instrumentation system that monitors, senses, or characterizes tubing and that validates and interprets tubing data. FIGS. 3 and 8 provide flow diagrams of methods for acquiring, processing, validating, and interpreting tubing data. FIGS. 4, 5, 6 provide illustrations of an oil well pumping system and operational conditions thereof.

The invention can be embodied in many different forms and should not be construed as limited to the embodiments set forth herein; rather, these embodiments are provided so that this disclosure will be thorough and complete, and will fully convey the scope of the invention to those having ordinary skill in the art. Furthermore, all "examples" or "exemplary embodiments" given herein are intended to be non-limiting, and among others supported by representations of the present invention.

Moreover, although an exemplary embodiment of the invention is described with respect to sensing or monitoring a tube, tubing, or pipe moving though a measurement zone adjacent a wellhead, those skilled in the art will recognize that the invention may be employed or utilized in connection with a variety of applications in the oilfield or another operating environment.

Turning now to FIG. 1, this figure illustrates a system 100 for servicing an oil well 175 that scans tubing 125 as the tubing 125 is extracted from or inserted into the well 175 according to an exemplary embodiment of the present invention.

The oil well 175 comprises a hole bored or drilled into the ground to teach an oil-bearing formation. The borehole of the well 175 is encased by a tube or pipe (not explicated shown in FIG. 1), known as a "casing," that is cemented to down-hole formations and that protects the well from unwanted formation fluids and debris.

Within the casing is a tube 125 that carries oil, gas, hydrocarbons, petroleum products, and/or other formation fluids, such as water, to the surface. In operation, a sucker rod string (not explicitly shown in FIG. 1), disposed within the tube 125, forces the oil uphole. Driven by strokes from an uphole machine, such as a "rocking" pump jack, the sucker rod moves up and down to communicate reciprocal motion to a downhole pump (not explicitly shown in FIG. 1). With each stroke, the downhole pump moves oil up the tube 125 towards the wellhead. FIG. 4, discussed below, illustrates an exemplary pumping system for an oil well 175.

As shown in FIG. 1, a service crew uses a workover or service rig 140 to service the well 175. During the illustrated procedure, the crew pulls the tubing 125 from the well, for example to repair or replace the downhole pump. The tubing 125 comprises a string of sections, each of which may be referred to as a "joint," that typically range in length from 29 to 34 feet (about 8.8 to 10.3 meters). The joints screw together via unions, tubing joints, or threaded connections.

The crew uses the workover rig 140 to extract the tubing 125 in increments or steps, typically two joints per increment. The rig 140 comprises a derrick or boom 145 and a cable 105 that the crew temporarily fastens to the tubing string 125. A motor-driven reel 110, drum, winch, or block and tackle pulls the cable 105 thereby hoisting or lifting the tubing string 125 attached thereto. The crew lifts the tubing string 125 a vertical distance that approximately equals the height of the derrick 145, typically about sixty feet or two joints.

More specifically, the crew attaches the cable 105 to the timing string 125, which is vertically stationary during the attachment procedure. The crew then lifts the tubing 125, generally in a continuous motion, so that two joints are extracted from the well 175 while the portion of the tubing string 125 below those two joints remains in the well 175. When those two joints are out of the well 175, the operator of the reel 110 stops the cable 105, thereby halting upward motion of the tubing 125. The crew then separates or unscrews the two exposed joints from the remainder of the tubing string 125 that extends into the well 175. A clamping apparatus grasps the tubing string 125 while the crew unscrews the two exposed joints, thereby preventing the string 125 from dropping into the well 175 when those joints separate from the main string 125.

The crew repeats the process of lifting and separating two-joint sections of tubing from the well 175 and arranges the extracted sections in a stack of vertically disposed joints, known as a "stand" of tubing. After extracting the full tubing string 125 from the well 175 and servicing the pump, the crew reverses the step-wise tube-extraction process to place the tubing string 125 back in the well 175. In other words, the crew uses the rig 140 to reconstitute the tubing string 125 by threading or "making up" each joint and incrementally lowering the tubing string 125 into the well 175.

The system 100 comprises an instrumentation system for monitoring, scanning, assessing, or evaluating the tubing 125 as the tubing 125 moves into or out of the well 175. The instrumentation system comprises a tubing scanner 150 that obtains information or data about the portion of the tubing 125 that is in the scanner's sensing or measurement zone 155. Via a data link 120, an encoder 115 provides the tubing scanner 150 with speed, velocity, and/or positional information about the tube 125. That is, the encoder 115 is mechanically linked to the reel 110 to determine motion and/or position of the tubing 125 as the tubing 125 moves through the measurement zone 155.

As an alternative to the illustrated encoder 115, some other form of positional or speed sensor can determine the derrick's block speed or the rig engine's rotational velocity in revolution per minute ("RPM"), for example.

Another data link 135 connects the tubing scanner 150 to a computing device, which can be a laptop 130, a handheld, a personal communication device ("PDA"), a cellular system, a portable radio, a personal messaging system, a wireless appliance, or a stationary personal computer ("PC"), for example. The laptop 130 displays data that the tubing scanner 150 has obtained from the tubing 125. The laptop 130 can present the tubing data graphically, for example in a trend format. The service crew monitors or observes the displayed data on the laptop 130 to evaluate the condition of the tubing 125. The service crew can thereby grade the tubing 125 according to its fitness for continued service, for example.

The communication link 135 can comprise a direct link or a portion of a broader communication network that carries information among other devices or similar systems to the system 100. Moreover, the communication link 135 can comprise a path through the internet, an intranet, a private network, a telephony network; an internet protocol ("IP") network, a packet-switched network, a circuit-switched network, a local area network ("LAN"), a wide area network ("WAN"), a metropolitan area network ("MAN"), the public switched telephone network ("PSTN"), a wireless network, or a cellular system, for example. The communication link 135 can further comprise a signal path that is optical, fiber optic, wired, wireless, wire-line, waveguided, or satellite-based, to name a few possibilities. Signals transmitting over the link 135 can carry or convey data or information digitally or via analog transmission. Such signals can comprise modulated electrical, optical, microwave, radiofrequency, ultrasonic, or electromagnetic energy, among other energy forms.

The laptop 130 typically comprises hardware and software. That hardware may comprise various computer components, such as disk storage, disk drives, microphones, random access memory ("RAM"), read only memory ("ROM"), one or more microprocessors, power supplies, a video controller, a system bus, a display monitor, a communication interface, and input devices. Further, the laptop 130 can comprise a digital controller, a microprocessor, or some other implementation of digital logic, for example.

The laptop 130 executes software that may comprise an operating system and one or more software modules for managing data. The operating system can be the software product that Microsoft Corporation of Redmond, Wash. sells under the registered trademark WINDOWS, for example. The data management module can store, sort, and organize data and can also provide a capability for graphing, plotting, charting, or trending data. The data management module can be or comprise the software product that Microsoft Corporation sells under the registered trademark EXCEL, for example.

In one exemplary embodiment of the present invention, a multitasking computer functions as the laptop 130. Multiple programs can execute in an overlapping timeframe or in a manner that appears concurrent or simultaneous to a human observer. Multitasking operation can comprise time slicing or timesharing, for example.

The data management module can comprise one or more computer programs or pieces of computer executable code. To name a few examples, the data management module can comprise one or more of a utility, a module or object of code, a software program, an interactive program, a "plug-in," an "applet," a script, a "scriptlet," an operating system, a browser, an object handler, a standalone program, a language, a program that is not a standalone program, a program that runs a computer, a program that performs maintenance or general purpose chores, a program that is launched to enable a machine or human user to interact with data, a program that creates or is used to create another program, and a program that assists a user in the performance of a task such as database interaction, word processing, accounting, or file management.

As discussed in further detail below and as shown in FIG. 7, the laptop 130 can process and analyze tubing data via a software program, machine executable instructions, or an analytics module. The analytics module validates or qualifies tubing data, for example determining which features or structures in the data are associated with actual defects or quality conditions and identifying other features and structures that seem unrelated to tubing quality. Moreover, the analytics module interprets the tubing data to help identify and diagnosis operating parameters and conditions of the well 175.

The analytics module and the data management module can interface with or connect to one another. The two modules may reside on a single computer or on separate computers. In one exemplary embodiment, the data management module comprises the analytics module. In one exemplary embodiment, the analytics module comprises the data management module. In one exemplary embodiment, the analytics module provides one or more of the functionalities of the data management module, as discussed above.

Turning now to FIG. 2, this figure illustrates a functional block diagram of a system 200 for scanning tubing 125 that is being inserted into or extracted from an oil well 175 according to an exemplary embodiment of the present invention. Thus, the system 200 provides an exemplary embodiment of the instrumentation system shown in FIG. 1 and discussed above, and will be discussed as such.

Those skilled in the information-technology, computing, signal processing, sensor, or electronics arts will recognize that the components and functions that are illustrated as individual blocks in FIG. 2, and referenced as such elsewhere herein, are not necessarily well-defined modules. Furthermore, the contents of each block are not necessarily positioned in one physical location. In one embodiment of the present invention, certain blocks represent virtual modules, and the components, data, and functions may be physically dispersed. Moreover, in some exemplary embodiments, a single physical device may perform two or more functions that FIG. 2 illustrates in two or more distinct blocks. For example, the function of the personal computer 130 can be integrated into the tubing scanner 150 to provide a unitary or commonly-housed hardware and software element that acquires and processes data and displays processed data in graphical form for viewing by an operator, technician, or engineer.

The tubing scanner 150 can include a rod-wear sensor 205 and a pitting sensor 255 for determining parameters relevant to continued use of the tubing 125. The rod-wear sensor 205 can assess relatively large tubing defects or problems such as wall thinning. Wall thinning may be due to physical wear or abrasion between the tubing 125 and the sucker rod that is reciprocates therein, for example. The pitting sensor 255 can detect or identify smaller flaws, such as pitting stemming from corrosion or some other form of chemical attack within the well 175. Those small flaws may be visible to the naked eye or may have microscopic features. Pitting can occur on the inside surface of the tubing 125, the so-called "inner diameter," or on the outside of the tubing 125.

The inclusion of the rod-wear sensor 205 and the pitting sensor 255 in the tubing scanner 150 is intended to be illustrative rather than limiting. The tubing scanner 150 can comprise another sensor or measuring apparatus that may be suited to a particular application. For example, the instrumentation system 200 can comprise a collar locator, a device that detects tubing cracks or splits, a temperature gauge, a camera, a hydrostatic tester, etc. In one exemplary embodiment of the present invention, the scanner 150 comprises or is coupled to an inventory counter, such as one of the inventory counting devices disclosed in U.S. Patent Application Publication Number 2004/0196032.

The tubing scanner 150 also comprises a controller 250 that processes signals from the rod-wear sensor 205 and the pitting sensor 255. The exemplary controller 250 has two filter modules 225, 275 that each, as discussed in further detail below, adaptively or flexibly processes sensor signals. In one exemplary embodiment, the controller 250 processes signals according to a speed measurement from the encoder 115.

The controller 250 can include a computer, microprocessor 290, computing device, or other implementation of programmable or hardwired digital logic. In one embodiment, the controller 250 comprises one or more application specific integrated circuits ("ASICS") or digital signal processing ("DSP") chips that perform the functions of the filters 225, 275, as discussed below. The filter modules 225, 275 can comprise executable code stored on ROM, programmable ROM ("PROM"), RAM, an optical disk, a hard drive, magnetic media, tape, paper, or some other machine readable medium.

The rod-wear sensor 205 comprises a transducer 210 that outputs an electrical signal containing information about the section of tubing 125 that is in the measurement zone 155. As discussed above, the transducer 210 typically responds to the magnetic flux density or flux intensity in the measurement zone 155 adjacent the tube 125. Sensor electronics 220 amplify or condition that output signal and feed the conditioned signal to the ADC 215. The ADC 215 converts the signal into a digital format, typically providing samples or snapshots of the wall thickness of the portion of the tubing 125 that is situated in the measurement zone 155.

The rod-wear filter module 225 receives the samples or snapshots from the ADC 215 and digitally processes those signals to facilitate machine- or human-based signal interpretation. The communication link 135 carries the digitally processed signals 230 from the rod-wear filter module 225 to the laptop 130 for recording and/or review by one or more members of the service crew. The service crew can observe the processed data to evaluate the suitability of the tubing 125 for ongoing service.

Similar to the rod-wear sensor 205, the pitting sensor 255 comprises a pitting transducer 260, sensor electronics 270 that amplify the transducer's output, and an ADC 265 for digitizing and/or sampling the amplified signal from the sensor electronics 270, Like the rod-wear filter module 225, the pitting filter module 275 digitally processes measurement samples from the ADC 265 and outputs a signal 280 that exhibits improved signal fidelity for display on the laptop 130.

Each transducers 210, 260 generates a stimulus and outputs a signal according to the tubing's response to that stimulus. For example, one of transducers 210, 260 may generate a magnetic field and detect the tubing's effect or distortion of that field. in one embodiment, the pitting transducer 260 comprises field coils that generate the magnetic field and flail effect sensors or magnetic "pickup" coils that detect field strength.

In one exemplary embodiment, one of the transducers 210, 260 may output ionizing radiation, such as gamma rays, incident upon the tubing 125. The tubing 125 blocks or deflects a fraction of the radiation and allows transmission of another portion of the radiation. In this example, one or both of the transducers 210, 260 comprises a detector that outputs an electrical signal with a strength or amplitude that changes according to the number of gamma rays detected. The detector may count individual gamma rays by outputting a discrete signal when a gamma ray interacts with the detector, for example. Ultrasonic or sonic energy can also be used to probe the tubing 125.

Processes of exemplary embodiments of the present invention will be discussed below with reference to FIGS. 3 and 8. An exemplary embodiment of the present invention can comprise one or more computer programs or computer-implemented methods that implement functions or steps described herein and illustrated in the exemplary flowcharts of FIGS. 3 and 8 and the diagrams of FIGS. 1, 2, and 4-7. However, it should be apparent that there could be many different ways of implementing the invention in computer programming, and the invention should not be construed as limited to any one set of computer program instructions. Further, a skilled programmer would be able to write such a computer program to implement the disclosed invention without difficulty based on the exemplary system architectures, data tables, data plots, and flowcharts and the associated description in the application text, for example.

Therefore, disclosure of a particular set of program code instructions is not considered necessary for an adequate understanding of how to make and use the invention. The inventive functionality of any claimed process, method, or computer program will be explained in more detail in the following description in conjunction with the remaining figures illustrating representative functions and program flow.

Certain steps in the processes described below must naturally precede others for the present invention to function as described. However, the present invention is not limited to the order of the steps described if such order or sequence does not alter the functionality of the present invention in an undesirable manner. That is, it is recognized that some steps may be performed before or after other steps or in parallel with other steps without departing from the scope and spirit of the present invention.

Section I: Interpreting Tubing Data

Turning now to FIG. 3, this two-part figure illustrates a flowchart of a process 300 for obtaining information about tubing 125 that is being inserted into or extracted from an oil well 175 and for analyzing that information according to an exemplary embodiment of the present invention. While process 300, which is entitled Obtain Tubing Data, describes conducting a tubing evaluation using the rod-wear sensor 205 and the pitting sensor 225, the underlying method can be applied to a wide variety of sensors and monitoring devices.

At step 305, the oil field service crew arrives at the well site with the tubing scanner 150 and the workover rig 140. The crew places the tubing scanner 150 at the wellhead, typically via a detachable mount, and locates the derrick 145 over the well 175. As illustrated in FIG. 1, a portion of the tubing 125 is disposed in the measurement zone 155 of the tubing scanner 150, while another portion, suspended below, extends in to the well 175.

At step 310, the service crew applies power to the tubing scanner 150 or turns it "on" and readies the derrick 145 to begin lifting the tubing string 125 out of the well 175 in two-joint steps or increments.

At step 315, pitting sensor electronics 270 and rod-wear sensor electronics 220 receive electrical energy from a power source (not shown in FIG. 2) and, in turn, supply electrical energy to the pitting transducer 260 and the rod-wear transducer 210. The transducers 210, 260 may generate magnetic fields with flux lines through the wall of the tubing 125, running generally parallel to the longitudinal axis of the tubing 125.

At step 320, the pitting transducer 260 outputs an electrical signal based on the tubing's presence in the sensor's measurement zone 155. More specifically, Hall Effect sensors, magnetic field-strength detectors, or pickup coils measure magnetic field strength at various locations near the tubing 125. The electrical signal, which may comprise multiple distinct signals from multiple detectors, carries information about the tubing wall. More specifically, the intensity of the transducer signal correlates to the amount of pitting of the section of the tubing 125 that is in the measurement zone 155. The output signal is typically analog, implying that it can have or assume an arbitrary or virtually unlimited number of states or intensity values.

The transducer 210 of the rod-wear sensor 205 also produces an analog electrical signal. The rod-wear transducer 210 may generate its signal using a magnetic field to probe the tubing, gamma rays, inductance, or some other measurement principle.

At step 325, the pitting sensor electronics 270 and the rod-wear sensor electronics 220 each receives an analog signal from the respective transducers 210, 260. The electronics 220, 270 condition the signals for subsequent processing, typically via applying amplification or gain to heighten signal intensity and/or to create more robust analog signals.

At step 330, the rod-wear ADC 215 and the pitting ADC 265 receive respective conditioned analog signals from the sensor electronics 220, 270 and generate corresponding digital signals. The digitization process creates digital or discrete signals that are each typically represented by one or more numbers. The ADCs 215, 265 generally operate on a time basis, for example each outputting one digital signal per second, sixteen per second, or some other number per second or minute, such as 10, 32, 64, 100, 1000, 10,000, etc. The ADCs 215, 265 can be viewed as sampling the analog signals from the transducers 210, 260 at a sample rate. Each output signal or sample can comprise bits transmitted on a single line or on multiple lines, for example serially or in a parallel format.

Each digital output from the ADCs 215, 265 can comprise a sample or snapshot of a transducer signal or of the extent of pitting or rod wear of the tubing 125. Thus, the ADCs 215, 265 provide measurement samples at predetermined time intervals, on a repetitive or fixed-time basis, for example.

In one exemplary embodiment of the present invention, the ADC's 215, 265 provide functionality beyond a basic conversion of analog signals into the digital domain. For example, the ADCs 215, 265 may each handle multiple digital samples and process or average those samples to output a burst or package of data. Such a data package can comprise a snapshot or a sample of tube pitting, wall thickness, or rod wear, for example.

Thus, in one exemplary embodiment, each ADC 215, 265 outputs a digital word at each sampling interval, wherein each word comprises a measurement of the signal intensity of the ADC's analog input. As discussed below, the filter modules 225, 275 filter or average those words. And in the alternative exemplary embodiment, each ADC 215, 265 not only implements the analog-to-digital conversion, but also performs at least some processing of the resulting digital words. That processing can comprise accumulating, aggregating, combining, or averaging multiple digital words and feeding the result to the appropriate filter modules 225, 275. The filter modules 225, 275, in turn, process the results output from the ADC's 215, 265, for example via adaptive filtering.

At step 335, the rod-wear filter module 225 and the pitting filter module 275 of the controller 250 receive digital signals from the ADCs 215, 265 and place those signals in memory, for example a short-term memory, a long-term memory, one or more RAM registers, or a buffer. As discussed above, the rod-wear filter module 225 and the pitting filter module 275 typically comprise executable instructions or software.

Thus, while the tubing 125 remains vertically stationary in the measurement zone 155 of the rod-wear sensor 205 and the pitting sensor 255, the ADC's 215, 265 provide a series or steam of digital samples, typically aligned on a recurring timeframe.

At step 340, the service crew raises the tubing string 125 to expose two joints or thirty-foot pieces of tubing 125 from the well 175. The service crew stops the vertical motion of the tubing 125 when the two joints are sufficiently out of the well 175 to facilitate separation of those joints from the full tubing string 125.

The service crew typically lifts the tubing string 125 in a continuous motion, keeping the tubing string 125 moving upward until the two joints have achieved an acceptable height above the wellhead. In other words, in one increment of tube extraction, the tubing string 125 starts at a rest, progresses upward with continuous, but not necessarily uniform or smooth, motion and ends at a rest. The upward motion during the increment may contain speed variations, fluctuations, or perturbations. In each step, the operator of the reel 110 may apply a different level of acceleration or may achieve a different peak speed. The operator may increase and decrease the speed in ramp-up/ramp-down fashion, for example.

At step 345, the rod-wear ADC 215 and the pitting ADC 265 continue outputting digital samples to the rod-wear filter module 225 and the pitting filter module 275. Thus, the rod-wear sensor 205 and the pitting sensor 255 can output digitally formatted measurements at regular time intervals. In one embodiment, the duration of each interval can remain fixed while the extraction speed changes and while the tubing's progress ceases between each extraction increment. In one exemplary embodiment, the ADCs 215, 265 continue outputting samples whether the tubing 125 is moving or is stopped.

At step 350, the filter modules 225, 275 filter or average the samples that they receive from the ADCs 215, 265. The filter modules 225, 275 can implement the filtering via DSP or some other form of processing the signals from the sensors 205, 255. The filter modules 225, 275 can apply flexible amounts of filtering based on an application of a rule or according to some other criterion. For example, the digital signals from the rod-wear sensor 205 and the pitting sensor 255 can receive a level of averaging, wherein the level varies according to tubing speed.

Exemplary embodiments of methods and systems for filtering signals from rod-wear sensor 205 and pitting sensor 255 are discussed in Section II.

As discussed in Section II, the filter modules 225, 275 can he employed to digitally process sensor data to improve the data's fidelity, quality, or usefulness. Subjecting the tubing data to digital signal processing ("DSP") can facilitate robust data interpretation, for example to help a person or a machine evaluate the validity or quality of the data, the condition of tubing, or the state of the well 175. Processing tubing data can comprise applying a flexible level of filtering, smoothing, or averaging to the data, wherein the level changes based on a criterion or according to a rule. The level can vary in response to a change in tubing speed, noise in the raw data, or some other parameter. For example, the filter modules 225, 275 can suppress or attenuate signal variations associated with or attributable to noise, random events, or conditions that typically have little or no direct correlation to valid tubing defects. Meanwhile, the filter modules 225, 275 can process signals in a manner that preserves signal structures, spikes, or amplitude changes that are indicative of actual tubing defects.

At step 355, the tubing scanner 150 forwards the digitally processed tubing samples to the laptop 130. The laptop 130 displays the data, typically in the form of one or more graphs, plots, or trends, for the service crew's observation.

At step 360, a member of the crew views and interprets the data displayed on the laptop 130. The operator, or an engineer or technician, typically grades or classifies each joint of extracted tubing according to pitting damage, wall thickness, and/or another factor. The operator may classify some tubing joints as unfit for continued service, while grading other sections of tubing 125 as marginal, and still others as having pristine condition. The operator may use a system of color codes, for example. In one exemplary embodiment, the grading is automatic, autonomous, or computer-implemented.

At inquiry step 365, the service crew determines whether the current extraction increment completes the tubing's extraction from the well 175. More specifically, the operator may determine if the pump attached to the bottom of the tubing string 125 is near the wellhead. If all tubing joints have been removed, process 300 executes step 370 following step 365. If tubing 125 remains downhole, process 300 loops back to step 340 and repeats step 340 and the steps that follow. In that case, the service crew continues to extract tubing 125, and the tubing scanner 150 continues to evaluate extracted tubing 125.

After servicing the pump and/or the well, the crew incrementally "makes up" and inserts the tubing string 125 into the well 175 to complete the service job. In one exemplary embodiment of the present invention, the tubing scanner 150 scans the tubing 125 while inserting the tubing 125 into the well 175, effectively conducting many of the steps of process 300 in reverse. In one exemplary embodiment of the present invention, pitting and rod-wear data is collected while the tubing 125 moves uphole, and the tubing 125 is monitored for cracks as the tubing 125 moves downhole.

If inquiry step 365 results in a determination that the full timing string 125 has been removed from the well 175, then step 370, which is entitled Analyze Data, follows step 365. That is, process 300 executes step 370 when the tubing scanner 150 has obtained rod-wear data and pitting data from the full tubing string 125.

At step 370, the laptop 130 presents a depth log of the rod-wear data and the pitting data on a graphical user interface ("GUI") or via some other display capability. The laptop 130 can generate the depth log of rod wear and pitting via correlating time-based data samples to depth according to positional information from the encoder 115.

Exemplary embodiments of methods and systems for assigning a depth to each data sample, and for generating a depth log of the data samples are discussed in Section III.

As will be discussed in further detail below, at step 370, the laptop 130 also processes and analyzes the tubing data to determine inconsistencies in the data, to validate the data, to infer operational aspects of the well 175, and/or to identify and diagnosis well conditions. FIG. 8 illustrates a flowchart of an exemplary method, process 370, for conducting the analysis of step 370. That is, process 370, discussed below, provides an exemplary embodiment of step 370 in process 300.

In preparation for discussing the steps of process 370, it will be useful to review parameters and operational conditions of a typical oil well 175 and to describe an exemplary architecture of the laptop 130. FIGS. 4, 5, and 6 present exemplary oil well conditions that may relate to data from the tubing scanner 150. Meanwhile, FIG. 7 presents an exemplary laptop system 130 for analyzing the rod-wear and pitting data. Those skilled in the art will appreciate that the elements of these figures are not drawn to scale and that various aspects and/or dimensions have been exaggerated to help describe how to make and use an exemplary embodiment of the present invention.

Turning now to FIG. 4, this figure illustrates a system 400 for obtaining hydrocarbons from an oil well 175 according to an exemplary embodiment of the present invention. A pump jack 405 imparts the sucker rod 415 with reciprocal vertical motion. As the pump jack 405 "see-saws" or rocks up and down, it drives the sucker rod 415 to piston up and down. Thus, the stroke 440 of the pump jack 405 defines the corresponding vertical travel of the sucker rod 415 at the top of the well 175.

A production engineer can set the stroke, typically about six feet, according to the depth of the well 175, the viscosity of the hydrocarbons, empirical results, or another parameter. The engineer may also set the stroke speed or the cycle time of a full stroke in an attempt to increase to well performance.

The stroke 440 typically varies along the depth of the well 175, with stroke length gradually increasing towards the bottom of the well 175 as a result of elasticity of the sucker rod 415. That is, the elasticity of the sucker rod 415 tends to amplify the stroke length along the depth of the well 175. The phenomenon is analogous to a person holding a rubber band in his hand with a ball suspended below; wherein slight hand twitches produce significant bail motions. For example, a six-foot stroke 440 at the pump jack 405 may yield a ten-foot stroke 440 at the downhole pump 430.

The well 175 has an annular casing 410, extending down to an oil bearing formation 435, that prevents borehole collapse and protects the well 175 from unwanted contamination Suspended within that casing 410 are the tubing 125 and the sucker rod 415. While the sucker rod 415 reciprocates up and down, driven by the pump jack 405, the tubing 125 remains essentially stationary. Thus, the sucker rod 415 pistons within the tubing 125 and transfers cyclical vertical motion to the pump 430. Induced vertical motion of the pump's components produces a pressure differential that causes the hydrocarbons to flow uphole, for collection at the wellhead.

Each joint 425 of the sucker rod 415 has a specified length and a specified length tolerance. For example, an oil industry standard could specify each joint 425 has a length of twenty-five feet and a length tolerance of plus-or-minus one inch. The connection point between each tubing joint 425 in the tubing string 125 can include a connector, a coupler, a union, a threaded surface, or another fastener, that can be referred to as a collar 420. The collars 420 typically have a larger diameter than the diameter of the main sections of the sucker rod joints 425, i.e., the collars 420 are somewhat bulbous.

The reciprocal motion of the sucker rod 415 within the tubing 125 tends to produce rod wear where the collars 420 contact the tubing 125. Referring now to FIG. 5, this figure illustrates well conditions associated with rod wear according to an exemplary embodiment of the present invention.

Figure 5A:
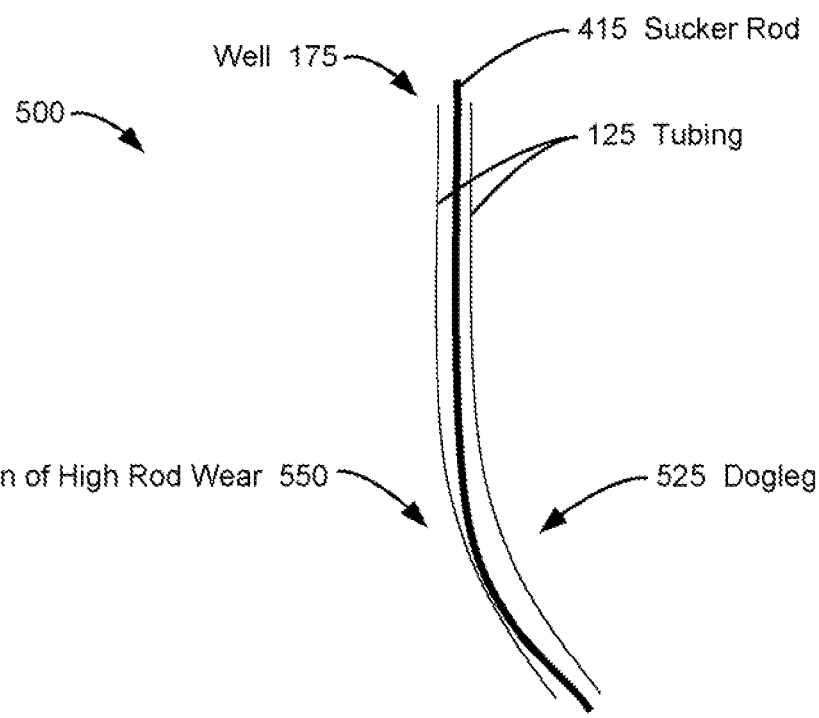
FIGS. 5A, 5B, and 5C, collectively

FIG. 5A illustrates an oil well 175 with a dogleg 525 that causes contact between the tubing 125 and the reciprocating collars 420. The dogleg 525 can comprise a directional deviation of the well borehole, a kickoff location, or a bend in the casing 410 associated with curvature of the well 175.

Intentional steering of a drill bit during drilling of the well, for example in connection with horizontal or directional drilling, may have caused the dogleg 525. Alternatively, the dogleg 525 may have resulted from inadvertent wander of the drill bit. In either case, the driller or an open-hole logging crew will typically have produced a directional map of the well 175 that describes the orientation of the well 175 along the well depth.

In the illustrated situation 500, the reciprocating collars 420 rub against the tubing surface that lies along the outer circumference of the dogleg's radius of curvature. The rubbing action typically causes a region 550 of high rod wear that is biased to the side of the tubing 550 at which contact occurs.

Figure 5B:
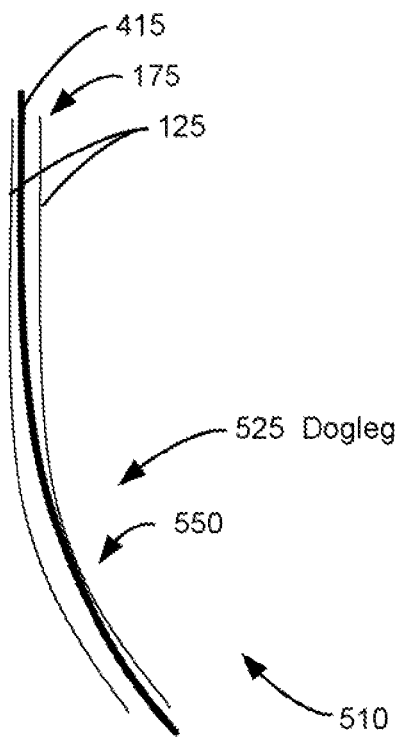

FIG. 5B illustrates another exemplary scenario 510 in which the sucker rod 415 contacts the tubing 125 along the inner portion of the radius of curvature of the dogleg 525. In this situation 510, rod wear and wall thinning may occur within the tubing 125 on the inner surface that is situated towards the inside of the dogleg bend 525.

Figure 5C:
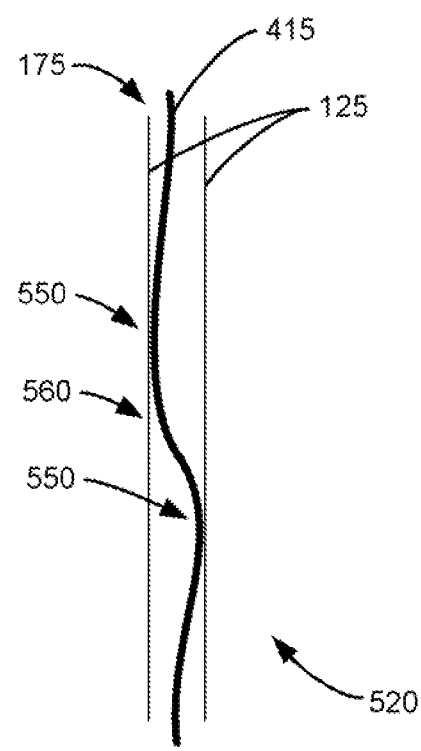

FIG. 5C illustrates yet another exemplary oil well situation 520 that may produce rod wear via contact between the tubing 125 and the collars 420 of the sucker rod 415 that moves in repetitive strokes therein. In this exemplary situation 520, a vibration or a resonant oscillation occurs or sets up in the sucker rod 415. That is, the sucker rod string 415 buckles or deforms repeatedly in response to the power strokes 415 of the pump jack 405. A dogleg 525 or a buildup of paraffin within the tubing 125 may cause such buckling, for example. Even without a dogleg 525 or a paraffin issue, a particular set of mechanical and dynamic parameters, which may involve weight distribution and component elasticity, can lead the sucker rod 415 to resonate. In other words, the system 400 can be prone to harmonic motion if the system components offer a "natural frequency" or a harmonic state that the pump jack 405 excites.

The regions of high rod wear 550 may occur at multiple depth locations in the tubing 125. A region 565 having less rod wear or no rod wear typically separates the regions 550 of high wear. In other words, unwanted sucker rod harmonics may result in a distinctive wear pattern that comprises a low-rod-wear region 560 between two high-rod-wear regions 550. Moreover, the tubing string 415 may exhibit an alternating series of high-wear regions 550 and low-wear regions 560. Each of those high-wear regions typically comprises multiple wear grooves, as shown in FIG. 6 and discussed below.

Turning now to FIG. 6, this figure illustrates a rod-wear pattern according to an exemplary embodiment of the present invention. More specifically, FIG. 6 illustrates a region 550 of rod wear representative of the high-rod-wear regions 550 shown in FIG. 5 and discussed above.

Contact between the sucker rod collars 420 and the inner wall of the tubing 125 creates a pattern of wear features 625. The reciprocal motion of the collars 420 causes wall thinning of the tubing 125 via abrasion. Each rod-wear feature 625 has a length that is similar to or that correlates with the stroke length 440. As discussed above, the stroke length 440, and thus the length of each wear feature 625, may vary according to the depth of the well 175 and the vertical location of the worn tubing section in the well 175.

The distance 650 between rod-wear features 625 approximates the length 650 of the sucker rod joints 425, which may be standardized to 25 feet. Each feature 625 in the pattern of rod-wear features 625 may be separated by a known distance 650, e.g., 25 feet.

Turning now to FIG. 7, this figure illustrates a functional block diagram of a computer system for analyzing and displaying tubing data according to an exemplary embodiment of the present invention. The laptop 130 comprises a display 725 for presenting logs of tubing data and for displaying alerts, interpretative results, validity findings, data confidence information, etc.

A microprocessor 720 or some other digital circuit executes software, instructions, or code. The analytics module 750 comprises one or more software programs that implement or embody a method for data analysis. The analytics module 750 receives digitally filtered rod-wear data 230 and digitally filtered pitting data 280 that the tubing scanner 150 supplies over the communication link 135.

A buffer, memory array, hard drive, or some other storage facility of the laptop 130 typically holds the rod-wear data and the pitting data to facilitate data access by analytics module 750. For example, a memory device associated with the analytics module 750 may store the samples in a table of memory cells, an array, or a bank of memory registers.

As will be discussed in further detail below, the analytics module provides diagnostic information about the well 175, interprets scanning data, and/or evaluates data for validity. More specifically, an exemplary embodiment of the analytics module 750 comprises instructions for executing the appropriate steps of process 370.

Turning now to FIG. 8, this figure illustrates a flowchart of a process 370 for processing tubing data to validate and interpret the data according to an exemplary embodiment of the present invention. As discussed above, process 370, which is entitled Analyze Data, provides an exemplary embodiment of step 370 of process 300, which FIG. 3 illustrates in flowchart form.

Process 800 is described in the exemplary situation of a laptop 130 performing certain of the method's steps. However, in an alternative embodiment, software executing on the tubing scanner controller 250, a remote computer, or a web-based data processing center implements one or more of the data processing steps of process 800.

At step 805 of process 370, the analytics module 750 receives positional data that the encoder 115 obtains from the rotational motion of the reel 110. The encoder data flows from the encoder 115 to the tubing scanner 150 via the data link 120 and from the tubing scanner 150 to the laptop's analytics module 750 via the data link 135. Thus, the analytics module 750 has positional information for each data sample that it receives from the tubing scanner 150.

The analytics module 750 matches or correlates each rod-wear data sample and each pitting data sample to a depth position on a tubing joint 425. In other words, the encoder data allows the analytics module 750 to assign a location of a tubing joint 425 to each data sample from the tubing scanner 150.

At step 810, the analytics module 750 assembles the rod-wear data and the pitting data of each tubing joint 425 into a log that spans the depth of the well 175. That is, the analytics module 750 creates a continuous depth log of rod wear and pitting on the tubing string 125. As discussed above, Section III describes a method for producing a depth log of tubing data for the well 175 via assembling data from individual tubing joints 425.

At step 815, the analytics module 750 processes the depth log of rod-wear data and pitting data to identify any patterns or features that may be present in the data. In other words, the analytics module 750 reviews the depth logs to determine whether they contain any substantive graphical structures that may reveal information about the well 175 or the validity of the data. Such patterns may comprise one or more distinctive signals, a series of peaks spaced at regular depth intervals, or a signal "fingerprint" that has appeared at another well site, to name a few possibilities.

In one exemplary embodiment of the present invention, processing the data comprises conducting a Fourier analysis. That is, pattern recognition software based on Fourier transformations can be employed for pattern recognition. To name a few more examples, the pattern recognition software can process the data via a genetic algorithm, fractal mathematics, artificial intelligence, adaptive filtering, Kalman filtering, least squares analysis, partial least squares, stochastic filtering, statistical pattern recognition, a linear algorithm, linear programming, or an expert system, for example. Moreover, the software may be based on commercially available code or some other pattern identification or recognition technique or tool known to those skilled in the art.

Identifying patterns can include determining if one or more rod-wear feature or pitting feature appears at regular or repeating depth intervals. The analytics module 750 can compare the features of the rod-wear log to the features of the pitting log to determine how much correlation exists between the logs and to identify related features.

While the data processing and analysis of step 815 may be implemented via computer, one embodiment of step 815 includes human intervention. Moreover, a human may view the logs and note any observed patterns or distinctive features.

At inquiry step 820, the analytics module 750 reviews the pattern analysis conducted at step 815 and determines whether the rod-wear log contains any features 625 that are isolated in depth from other rod-wear features 625. More specifically, the analytics module 750 determines if any rod-wear feature 625 exists without a corresponding rod-wear feature 625 that is displaced in depth according to the length 650 of a sucker rod joint 425. As discussed above with reference to FIGS. 4, 5, and 6, valid rod-wear features 625 typically occur in a group, with each feature 625 in the group separated by a depth 650 equivalent to the length 650 of the sucker rod joints 425.

If the analytics module 750 does not identify any isolated rod-wear features 625, then process 370 branches to step 835, and step 835 executes after step 820. Conversely, if the analytics module 750 identifies one or more isolated rod-wear features 625, then step 825 executes following step 820.

In one exemplary embodiment of the present invention, the analytics module 750 considers data from two or more tubing scans in connection with conducting steps 805-820. As discussed above, rod wear typically occurs as a series of grooves or rod-wear features 625 that are spaced from one another according to the length of the sucker rod joints 425. At each well service, the crew typically alters the tubing string 125 or the sucker rod string 415 to offset the wear patterns that occur between service calls. In other words, the crew changes the string 125 or the string 415 so that future wear is offset from past wear.

The crew may insert a shortened joint of tubing into the tubing string 125 or a shortened sucker rod joint 425 into the sucker rod string 415. In this manner, the crew avoids creating new wear grooves 625 on top of old wear grooves 625 and extends the useful life of the tubing 125. In other words, offsetting the wear features 625 that form between service calls helps avoid an accumulation of wear and wall thinning.

Accordingly, a tubing log collected at any particular service call may comprise multiple wear patterns superimposed upon one another. That is, the log characterizes the wear features 625 that occurred since the last service call as well as the features that occurred prior to that last service call.

In one exemplary embodiment of the present invention, the analytics module 750 retains, or can otherwise access, each wear log that it creates for the well 175. At each service call, the analytics module 750 can process newly acquired data based on stored data from earlier service calls.

In one exemplary embodiment, the analytics module 750 annotates the log, presented on the display 725, to differentiate between new wear features 625 and wear features that occurred prior to the most recent service call. In one exemplary embodiment, the analytics module 750 subtracts one or more of the stored logs from the current log. In this manner, the analytics module 750 generates a log from which those earlier features have been canceled. In other words, a log of rod wear and pitting can be processed to remove features or artifacts that occurred outside of a time interval between the current service call and the most recent service call.

Figure 8A:
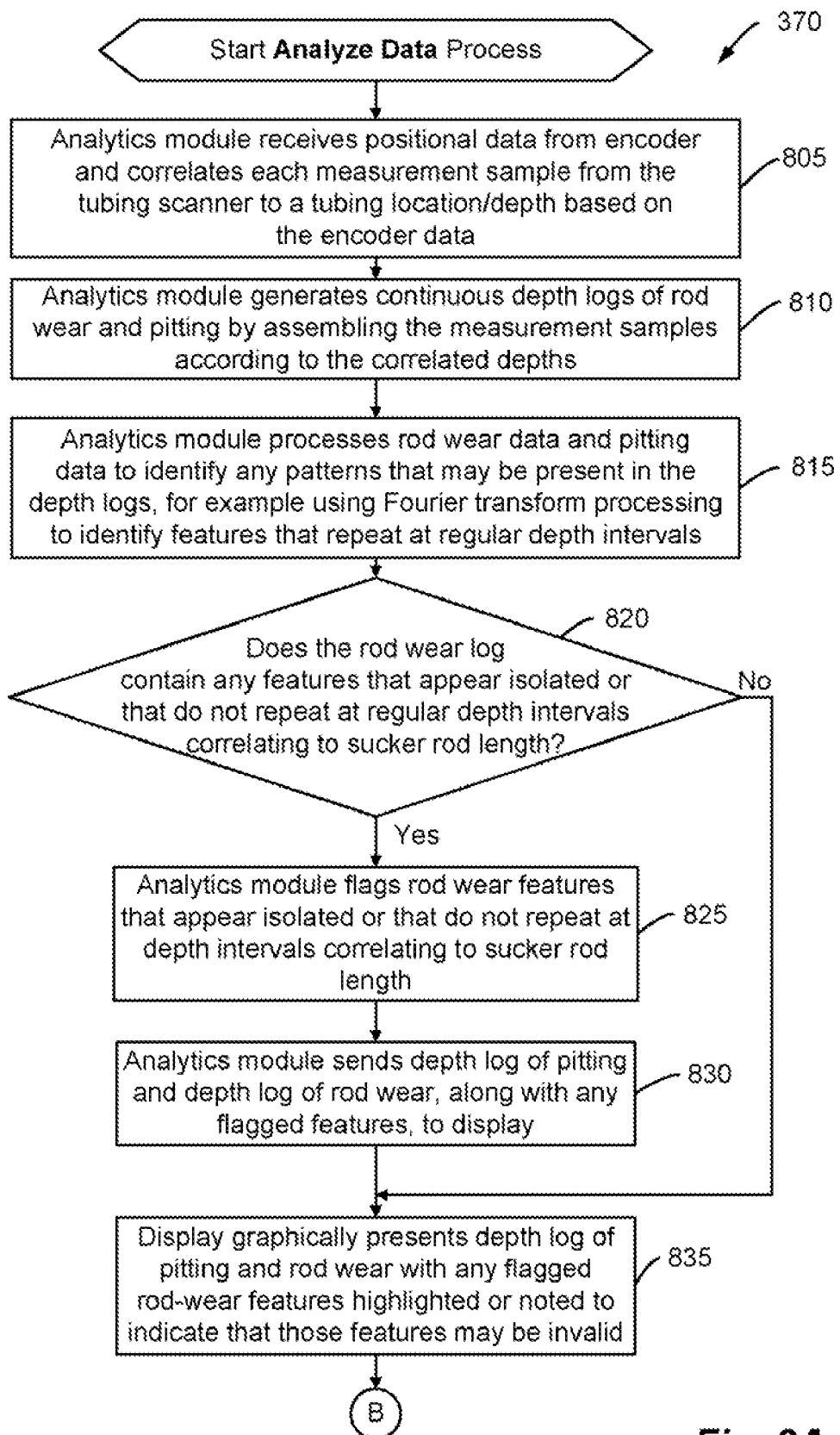
FIGS. 8A, 8B, and 8C, collectively
Figure 8B:
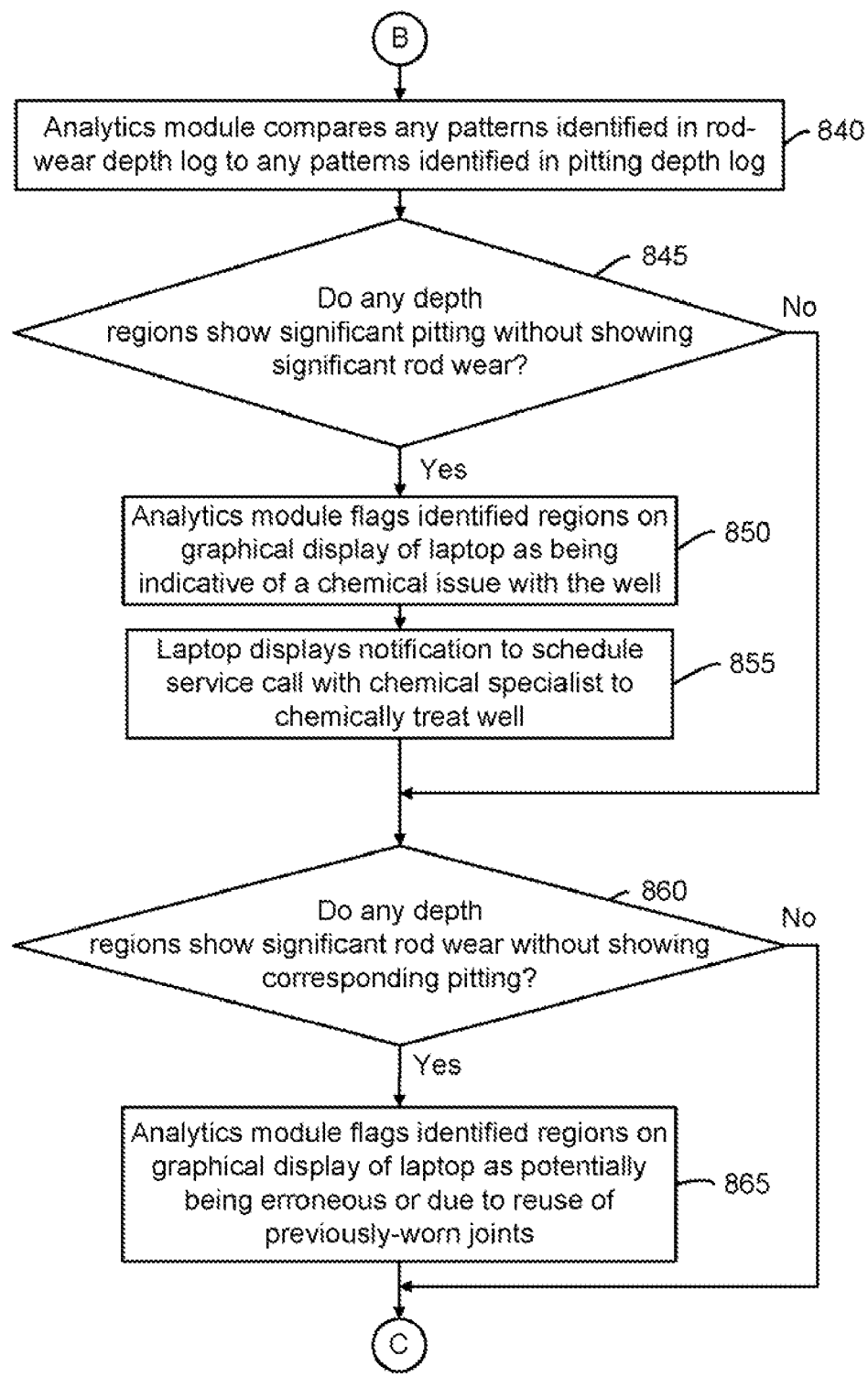

Referring now to the flowchart of FIG. 8A, at step 825, the analytics module 750 flags any rod-wear features 625 that appear isolated from other features 625 in a manner that indicates a potential validity issue with the underlying data. That is, the analytics module 750 notes any rod-wear features 625 that may unreliable based on a lack of supporting data that lends credibility to those features 625.

At step 830, the analytics module 750 sends the depth logs of rod wear and pitting to the display 725 along with any reliability or validity flags noted at step 825. At step 835, the display 725 presents the depth log of pitting and the depth log of rod wear in a graphical formal. In one exemplary embodiment, the two logs are presented on a common depth axis, for example in a single view or overlaid upon one another.

The displayed log notes or highlights any features that have been flagged as potentially invalid or of questionable reliability. In one exemplary embodiment, a confidence plot overlays or accompanies the rod-wear log. The confidence plot may comprise an indication of the reliability of each feature 625 present on the log. The confidence indication can be based on color codes, highlighted areas, icons, symbols, etc. Moreover, the display 725 may present one or more confidence indicators, confidence scores, numbers, or values that characterize the features of the log on a numerical scale.

At step 840, the analytics module 750 makes a comparison between any feature patterns identified in the rod-wear log and any feature patterns identified in the pitting log. That is, the analytics module 750 analyzes the data to determine how much, if any, correlation exists between the rod-wear patterns and the pitting patterns.

At inquiry step 845, the analytics module 750 determines whether any depth regions of the tubing string 125 have significant pitting without significant rod wear. The determination of step 845 is based on the correlation of step 840.

If the data shows that one or more tubing sections 125 has, along its depth, pitting features without corresponding rod-wear features, then step 850 follows step 845. In a well 175 that is operating properly, pitting typically accompanies rod wear. Beyond causing wall thinning via abrasion, contact between the reciprocating collars 420 and the tubing's inside diameter tends to swipe away the protective chemical film that typically coats the tubing surface. Without that protective coating, the tubing 125 is exposed to corrosive attack in the hostile downhole environment of the well 175.

Accordingly, an appearance of pitting without accompanying rod wear indicates that the tubing 125 is coming under a chemical attack that is unexplained by contact between the collars 420 and the tubing 125. Such pitting is often an indication that the well 175 is chemically imbalanced or otherwise would benefit from a chemical treatment.

At step 850, analytics module 750 flags the depth regions of the log that were identified at steps 840 and 845 to show that those regions may indicate that the well 175 should be chemically treated. The display 725 presents a message or notification of the potential need for a chemical treatment, and the message accompanies the displayed log.

At step 855, the laptop 130 displays a notification or an alert to schedule a service call with a chemical treatment specialist. In one exemplary embodiment of the present invention, the analytics module 750 autonomously contacts the specialist and may even initiate and schedule the service call or recommend a specific treatment regimen. Inquiry step 860, discussed below, follows step 855.

If the inquiry of step 845 results in a negative determination, that is a determination that the log does not contain any pitting features that are unaccompanied by rod wear, then process 370 skips steps 850 and 855. In this case, inquiry step 860 follows inquiry step 845.

At step 860, the analytics module 750 determines whether the log contains evidence of rod wear without corresponding evidence of pitting. As discussed above, valid rod-wear features 625 are typically accompanied by pitting features that occur when the reciprocating collars 420 swipe away the protective chemicals that otherwise shield the tubing 125 from chemical attack.

Accordingly, if the log contains rod wear that is unaccompanied by significant pitting, then the rod-wear data may be unreliable or of suspect quality. In this event, step 865 follows step 860. At step 865, the analytics module 750 flags as suspect any depth regions that exhibit rod wear without an expected level of pitting. The display 725 provides a visual indicator that such rod-wear features may not be valid.

The laptop 130 can mark the suspect data as potentially unreliable and can present a label on a graph of the data to highlight any suspect data. As discussed above, a graphing capability of the laptop 130 may overlay a confidence indicator upon the graphical depth log. The overlay may indicate the relative or absolute confidence of various portions of the log based on the analyses of process 370, including the result of inquiry step 860.

In one exemplary embodiment of the present invention, the analysis of steps 860 and 865 proceeds during the extraction of the tubing 125 from the well 175. That is, certain of the steps of process 370 may occur while the tubing 125 is moving or between tubing removal increments. In this event, the analytics module 750 can provide feedback to the operator of the reel 110, for example issuing an alert to slow down. In one exemplary embodiment, the analytics module 750 automatically slows the rotational speed of the reel 110, for example via a feedback loop, upon an appearance of unreliable data. In one exemplary embodiment, the analytics module 750 may instruct the service crew to lower one or more sections of the tubing 125 back into the well 175, for example to re-scan a joint 425 that is represented by apparently unreliable data. Alternatively, the crew may elect to physically mark a section of the tubing 125 that the analytics module 750 has been identified as being associated with data of suspect quality.

Figure 8C:
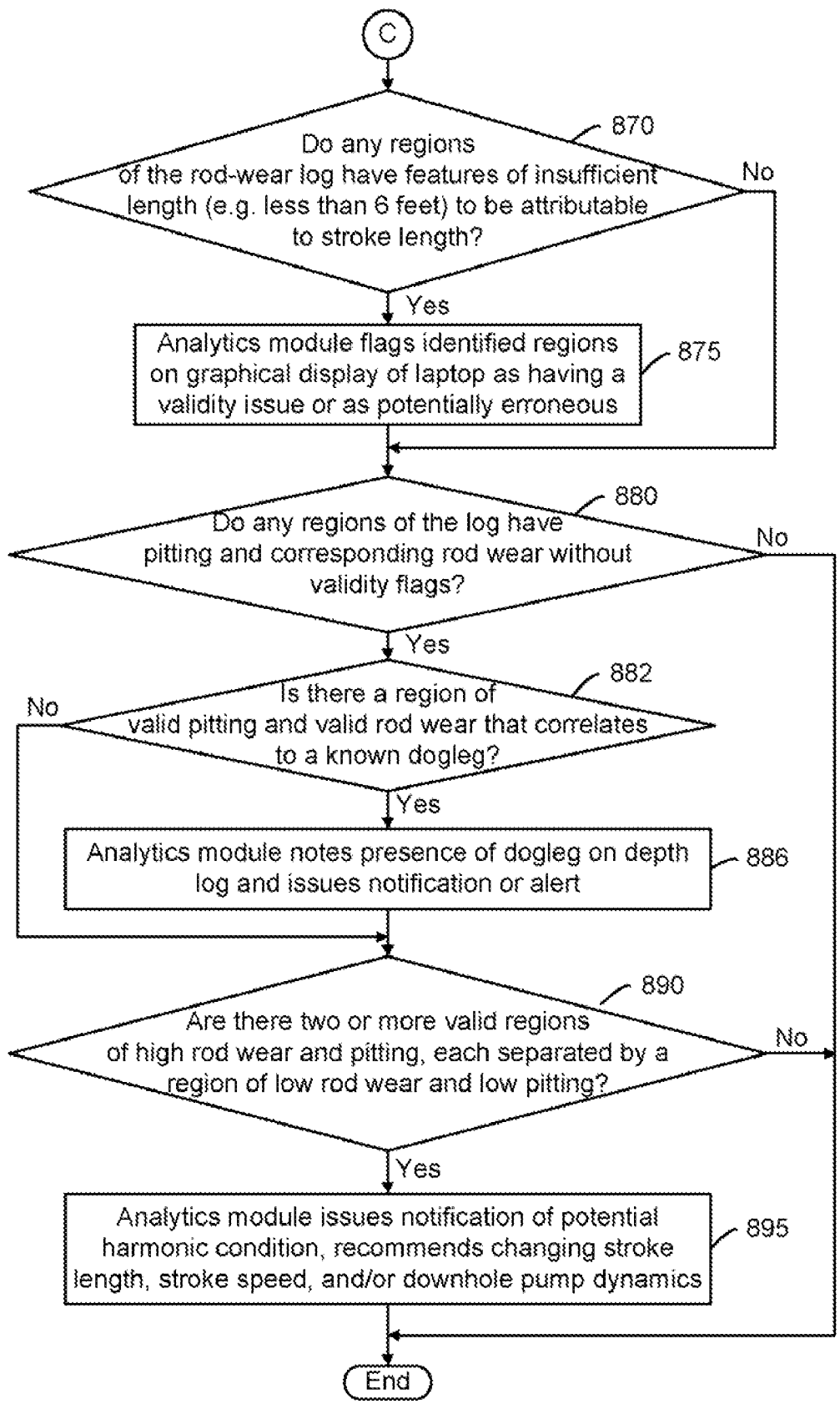

Inquiry step 870, shown on FIG. 8C, follows either of an execution of step 865 or a negative determination at step 860. At step 870, the analytics module 750 determines whether any features 625 of the rod-wear log are shorter than the stoke 440. That is, the analytics module 750 inspects the rod-wear features 625 to determine if any of those features 625 has an insufficient length to be explained by the downhole stroke 440. As discussed, the downhold stroke 440 can be longer than the uphole stroke 440.

If any feature 625 of the rod-wear log is shorter than the stroke 440, then at step 875, the analytics module 130 flags that feature 625 as being unreliable or potentially erroneous. In this case, process 370 executes step 880 following step 875. On the other hand, if all of the rod-wear features 625 are consistent with the stroke length 440, then process 370 bypasses step 875 and executes inquiry step 880 following inquiry step 870.

At inquiry step 870, the analytics module 750 determines whether any region of the log indicates both valid pitting and valid rod wear. That is, the analytics module 750 reviews the log to identify one or more depth regions that contain: pitting features that have not been flagged as having suspect validity; and rod-wear features that have not been flagged as having suspect validity. If the analytics module 750 does not identify any such depth regions, then process 370 ends following step 880. Conversely, if the analytics module 750 finds a section of tubing 125 with apparently valid pitting and apparently valid rod wear, then inquiry step 882 follows step 880.

At inquiry step 882, the analytics module 750 determines whether the well 175 has a dogleg 525 that correlates to any depth region noted at step 880. As discussed above, in many instances, a depth map of the well's borehole direction is generated in connection with drilling the well 175 or logging the well 175 prior to well completion. Thus, at each depth location, the directional deviation of the well 175 from vertical may be known, for example via a paper log or a data file.

A manager that has production responsibilities for the well 175 can obtain the well's directional information, for example from an archive, and can send that information to the laptop 130 or a user thereof. Thus, the analytics module 750 can receive directional data via an electronic data transmission or via scanning a paper log, for example.

If the analytics module 750 determines that a dogleg 525 appears to be associated with valid pitting features and valid rod-wear features, then process 370 executes step 886 following step 882. Otherwise, process 370 skips step 886 and executes step 890 following step 882.

At step 886, the analytics module 750 notes the presence of the dogleg 525 on the laptop display 725. An arrow, symbol, or icon posted over a specific depth region of the log can indicate the location of a significant change in the well's vertical direction. In one exemplary embodiment, the analytics module 750 highlights any pitting features or rod-wear features that appear to be linked to the dogleg 525.

At step 890, the analytics module 750 determines whether the log contains at least two regions that each exhibits a significant level of valid rod wear and a significant level of pitting, wherein an area of low rod wear and low pitting separates the two regions. That is, the analytics module 750 analyzes the pitting and rod-wear data to determine whether the sucker rod collars 420 appear to be rubbing against the tubing 125 in two areas that are separated in depth from one another.

If the data analysis indicates that the sucker rod 415 is wearing the tubing 125 at multiple depth locations, then step 895 follows step 890. As discussed above with reference to FIG. 5C, a pattern of rod wear that occurs at multiple depth intervals is evidence that the sucker rod 415 is vibrating or oscillating in an unwanted manner.

At step 895, the analytics module 750 issues a notification or a message that analysis of the log indicates that an uncontrolled harmonic oscillation has set up in the well's pumping system 400. In one exemplary embodiment, the notification is posted on the laptop display 725. The notification can also be transmitted to a remote location via the Internet, an intranet, a private network, a telephony network, an IP network, a packet-switched network, a circuit-switched network, a LAN, a WAN, a MAN, the PSTN, a wireless network, or a cellular system, for example.

Beyond identifying the presence of the harmonic oscillation, the analytics module 750 can recommend or prescribe a corrective action, such as a remedy. The analytics module 750 may recommend that a production engineer should change the stroke length 440 or the stroke speed, for example the number of strokes per minute. A recommended procedure to dampen or suppress the harmonics could also comprise changing some aspect of the downhole pump 430, for example replacing a tight-fitting component with a component that offers additional mechanical clearance.

Following execution of step 895 or a negative determination at step 890, process 800 ends.

Process 800 can be viewed as a method for validating information about a tube 125 that has been in a well 175, a method for analyzing and interpreting the information, and/or a method for diagnosing the well 175 based on processing the information. Moreover, an exemplary embodiment of the present invention can analyze information collected via scanning a tube 125 that has been disposed in an oil well 175, for example assigning a confidence to an aspect of the information or using the information to learn about the operation of the well 175.

Section II: Signal Filtering

Processes of exemplary embodiments of the present invention will now be discussed with reference to FIGS. 9-15. An exemplary embodiment of the present invention can comprise one or more computer programs or computer-implemented methods that implement functions or steps described herein and illustrated in the exemplary flowcharts, graphs, and data sets of FIGS. 9-15 and the diagrams of FIGS. 1 and 2. However, it should be apparent that there could be many different ways of implementing the invention in computer programming, and the invention should not, be construed as limited to any one set of computer program instructions. Further, a skilled programmer would be able to write such a computer program to implement the disclosed invention without difficulty based on the exemplary system architectures, data tables, data plots, and flowcharts and the associated description in the application text, for example.

Therefore, disclosure of a particular set of program code instructions is not considered necessary for an adequate understanding of how to make and use the invention. The inventive functionality of any claimed process, method, or computer program will be explained in more detail in the following description in conjunction with the remaining figures illustrating representative functions and program flow.

Certain steps in the processes described below must naturally precede others for the present invention to function as described. However, the present invention is not limited to the order of the steps described if such order or sequence does not alter the functionality of the present invention in an undesirable manner. That is, it is recognized that some steps may be performed before or after other steps or in parallel with other steps without departing from the scope and spirit of the present invention.

Figure 9A:
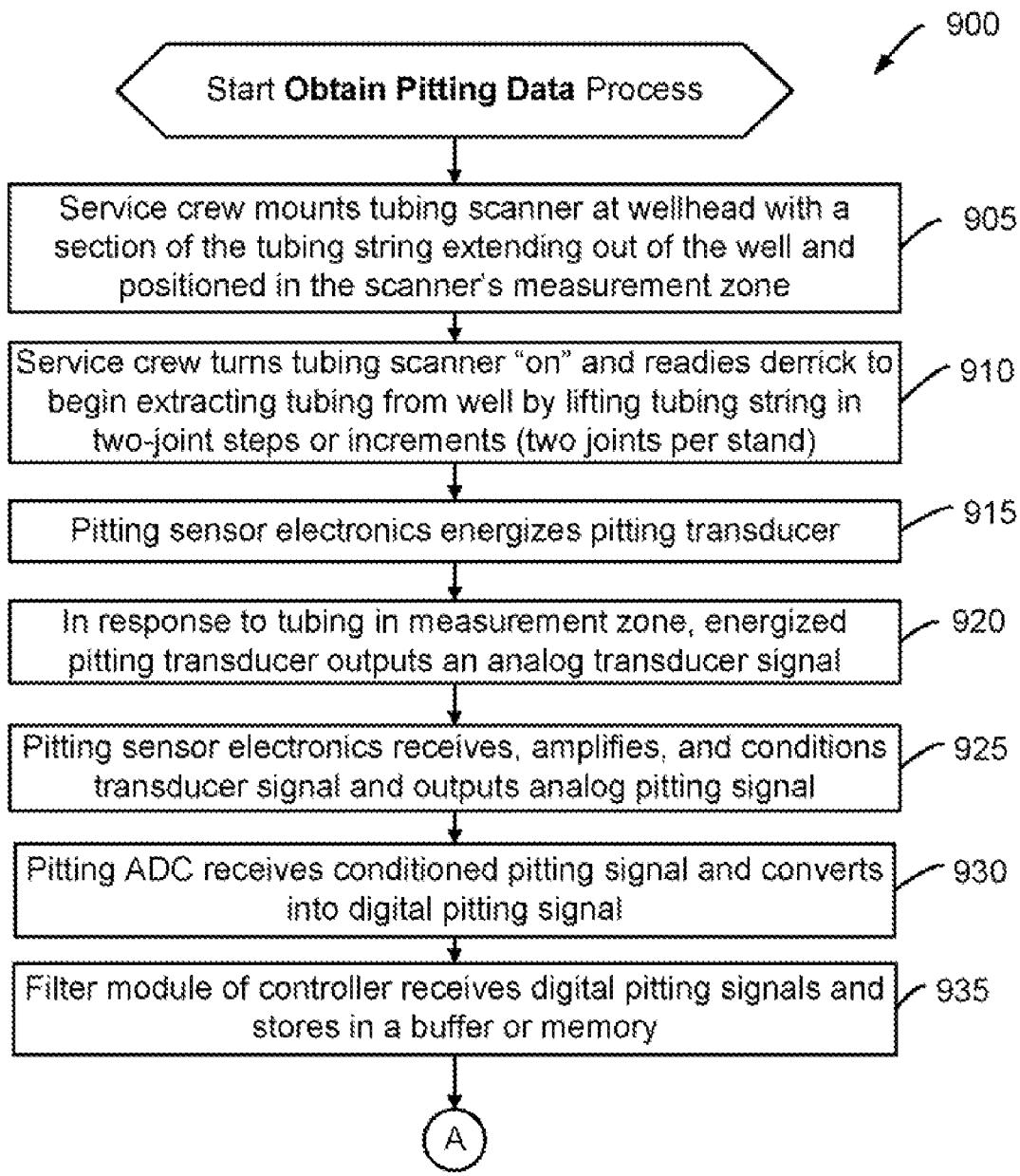
FIGS. 9A and 9B, collectively
Figure 9B:
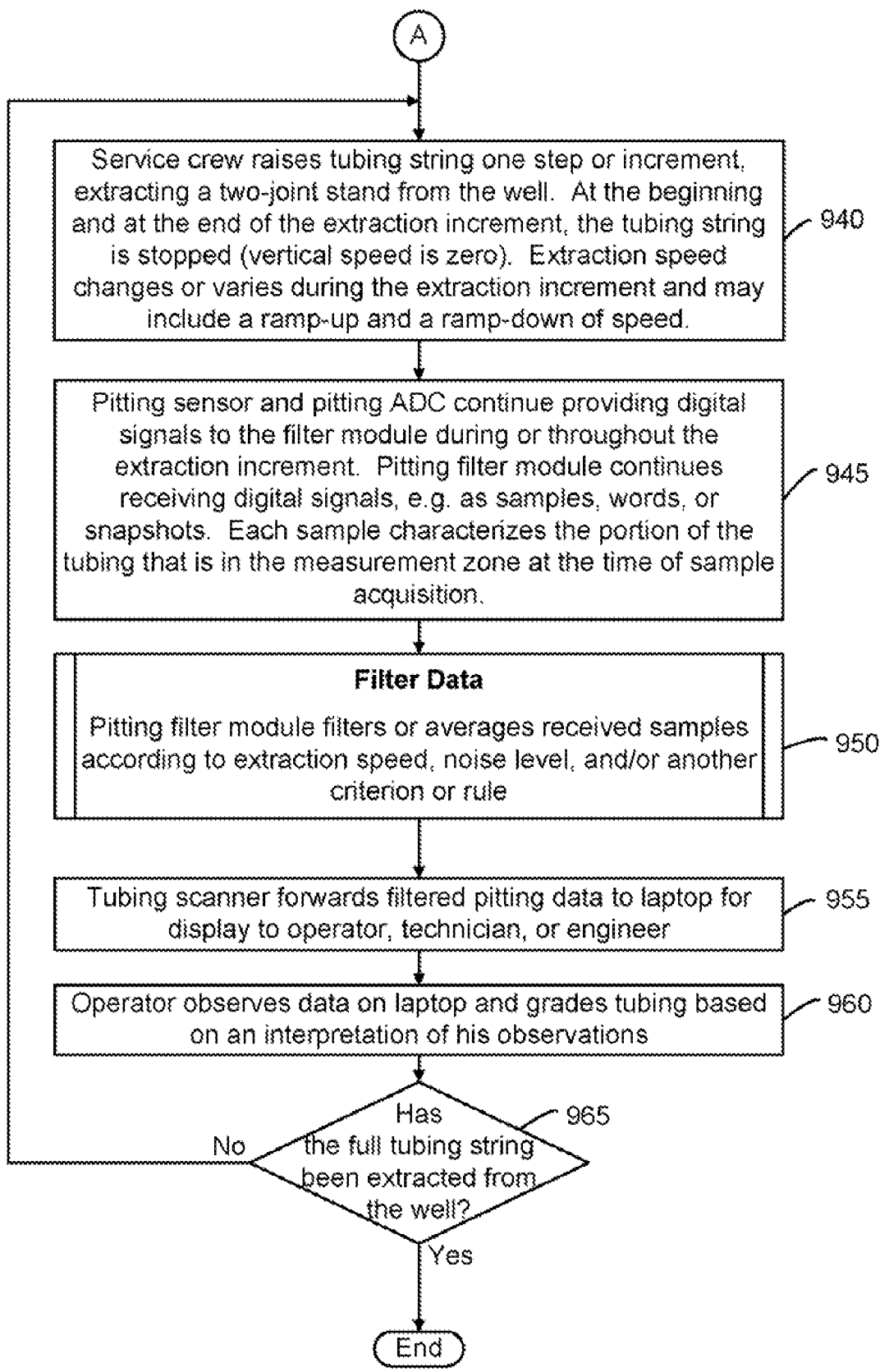

Turning now to FIG. 9, this two-part figure illustrates a flowchart of a process 900 for obtaining information about tubing 125 that is being inserted into or extracted from an oil well 175 according to an exemplary embodiment of the present invention. While process 900, which is entitled Obtain Pitting Data, describes conducting a tubing evaluation using the pitting sensor 225, the underlying method can be applied to various sensors and monitoring devices, including the rod-wear sensor 205 shown in FIG. 2 and discussed above.

At step 905, the oil field service crew arrives at the well site with the tubing scanner 150 and the workover rig 140. The crew places the tubing scanner 150 at the wellhead, typically via a detachable mount, and locates the derrick 145 over the well 175. As illustrated in FIG. 1, a portion of the tubing 125 is disposed in the measurement zone 155 of the tubing scanner 150, while another portion, suspended below, extends in to the well 175.

At step 910, the service crew applies power to the tubing scanner 150 or turns it "on" and readies the derrick 145 to begin lifting the tubing string 125 out of the well 175 in two-joint steps or increments.

At step 915, the pitting sensor electronics 270 receives electrical energy from a power source (not explicitly shown in FIG. 2) and, in turn, supplies electrical energy to the pitting transducer 260. The pitting transducer 260 generates a magnetic field with flux lines through the wall of the tubing 125, running generally parallel to the longitudinal axis of the tubing 125

At step 920, the pitting transducer 260 outputs an electrical signal based on the tubing's presence in the sensor's measurement zone 155. More specifically, Hall effect sensors, magnetic field-strength detectors, or pickup coils measure magnetic field strength at various locations near the tubing 125. The electrical signal, which may comprise multiple distinct signals from multiple detectors, carries information about the tubing wall. More specifically, the intensity of the transducer signal correlates to the amount of pitting of the section of the tubing 125 that is in the measurement zone 155. The output signal is typically analog, implying that it can have or assume an arbitrary or virtually unlimited number of states or intensity values.

At step 925, the pitting sensor electronics 270 receives the analog signal from the pitting transducer 260. The electronics 270 conditions the signal for subsequent processing, typically via applying amplification or gain to heighten signal intensity and/or to create a more robust analog signal.

At step 930, the ADC 265 receives the conditioned analog signal from the sensor electronics 270 and generates a corresponding digital signal. The digitization process creates a digital or discrete signal that is typically represented by one or more numbers. The ADC 265 generally operates on a time basis, for example outputting one digital signal per second, sixteen per second, or some other number per second or minute, such as 10, 32, 64, 100, 1000, 10,000, etc. The ADC 265 can be viewed as sampling the analog signal from the transducer 260 at a sample rate. Each output signal or sample can comprise bits transmitted on a single line or on multiple lines, for example serially or in a parallel format.

Each digital output from the ADC 265 can comprise a sample or snapshot of the transducer signal or of the extent of pitting of the tubing 125. Thus, the ADC 265 provides measurement samples at predetermined time intervals, on a repetitive or fixed-time basis, for example.

In one embodiment of the present invention, the ADC 265 provides functionality beyond a basic conversion of analog signals into the digital domain. For example, the ADC 265 may handle multiple digital samples and process or average those samples to output a burst or package of data. Such a data package can include a snapshot or a sample of tubing pitting, for example.

Thus, in one embodiment, the ADC 265 outputs a digital word at each sampling interval, wherein each word comprises a measurement of the signal intensity of the ADC's analog input. As discussed below, the filter module 275 filters or averages those words. And in an alternative embodiment, the ADC 265 not only implements the analog-to-digital conversion, but also performs at least some processing of the resulting digital words. That processing can include accumulating, aggregating, combining, or averaging multiple digital words and feeding the result to the filter module 275. The filter module 275, in turn, can process the results output from the ADCs 265, for example via adaptive filtering.

At step 935, the pitting filter module 275 of the controller 250 receives the digital signals from the ADC 265 and places those signal in memory, for example a short-term memory, a long-term memory, one or more RAM registers, or a buffer. As discussed above, the pitting filter module 275 typically comprises executable instructions or software.

Thus, while the tubing 125 remains vertically stationary in the measurement zone 155 of the pitting sensor 255, the ADC 265 provides a series or steam of digital samples, typically aligned on a recurring timeframe.

At step 940, the service crew raises the tubing string 125 to expose two joints or thirty-foot pieces of tubing 125 from the well 175. The service crew stops the vertical motion of the tubing 125 when the two joints are sufficiently out of the well 175 to facilitate separation of those joints from the full tubing string 125.

The service crew typically lifts the tubing string 125 in a continuous motion, keeping the tubing string 125 moving upward until the two joints have achieved an acceptable height above the wellhead. In other words, in one increment of tube extraction, the tubing string 125 starts at a rest, progresses upward with continuous, but not necessarily uniform or smooth, motion and ends at a rest. The upward motion during the increment may contain speed variations, fluctuations, or perturbations. In each step, the operator of the reel 110 may apply a different level of acceleration or may achieve a different peak speed. The operator may increase and decrease the speed in ramp-up/ramp-down fashion, for example.

At step 945, the pitting sensor ADC 265 continues outputting digital samples to the pitting filter module 275. Thus, the pitting sensor 255 can output digitally formatted measurements at regular time intervals. In one exemplary embodiment, the duration of each interval can remain fixed while the extraction speed changes and while the tubing's progress ceases between each extraction increment. In one exemplary embodiment the ADC 265 continues outputting samples whether the tubing 125 is moving or is stopped.

At step 950, the pitting filter module 275 filters or averages the samples that it receives from the pitting ADC 265. The pitting filter module 275 can implement the filtering via DSP or some other form of processing the signals from the pitting sensor 255. As will be discussed in further detail below, the pitting filter module 275 can apply a flexible amount of filtering based on an application of a tide or according to some other criterion. For example, the digital signals from the pitting sensor 255 can receive a level of averaging, wherein the level varies according to tubing speed.

Figure 10:
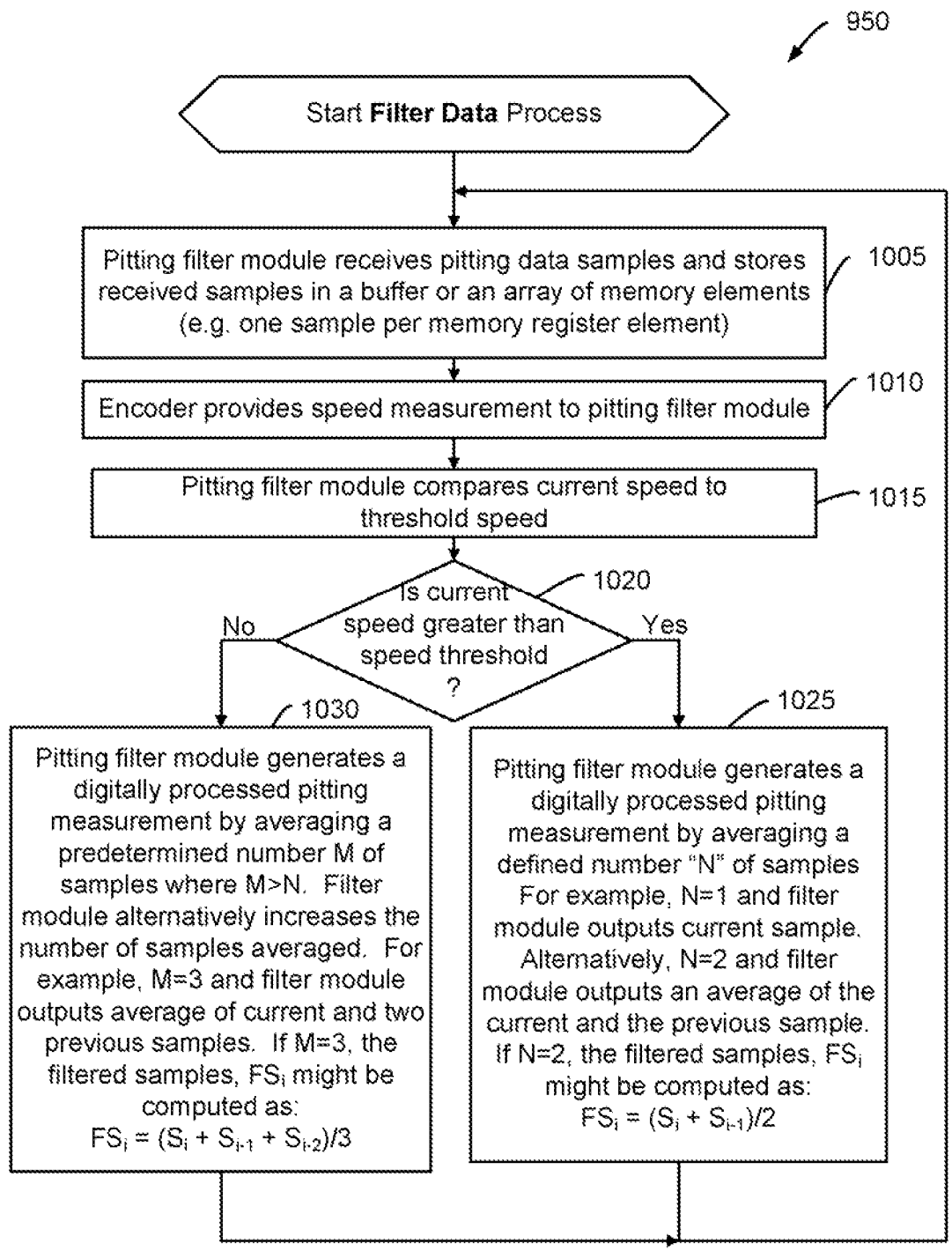
FIG. 10 is a flowchart of an exemplary process for filtering data that characterizes tubing in accordance with an embodiment of the present invention.

FIGS. 10 and 11 respectively present a flowchart and an accompanying dataset of an exemplary embodiment of step 950, as process 950, which is entitled Filter Data. In the exemplary embodiment of FIGS. 10 and 11, process 950 conducts data processing in an iterative manner. More specifically and as discussed in further detail below, process 950 typically runs or executes in parallel with and/or in coordination with certain other steps of process 900. Thus, process 900 avoids remaining "stuck" in the iterative loop of FIG. 4.

At step 955, the tubing scanner 150 forwards the digitally processed tubing samples to the laptop 130. The laptop 130 displays the data, typically in the form of one or more graphs, plots, or trends, for the service crew's observation.

At step 960, a member of the crew views and interprets the data displayed on the laptop 130. The operator, or an engineer or technician, typically grades or classifies each joint of extracted tubing according to pitting damage, wall thickness, and/or another factor. The operator may classify some tubing joints as unfit for continued service, while grading other sections of tubing 125 as marginal, and still others as having pristine condition. The operator may use a system of color codes, for example. In one exemplary embodiment, the grading is automatic, autonomous, or computer-implemented.

At inquiry step 965, the service crew determines whether the current extraction increment completes the tubing's extraction from the well 175. More specifically, the operator may determine if the pump attached to the bottom of the tubing string 125 is near the wellhead. If all tubing joints have been removed, process 900 ends. If tubing 125 remains downhole, process 900 loops back to step 940 and repeats step 940 and the steps that follow. In that case, the service crew continues to extract tubing 125, and the tubing scanner 150 continues to evaluate the extracted tubing 125.

After servicing the pump and/or the well, the crew incrementally "makes up" and inserts the tubing string 125 into the well 175 to complete the service job. In one exemplary embodiment of the present invention, the tubing scanner 150 scans the tubing 125 while inserting the tubing 125 into the well 175, effectively conducting many of the steps of process 900 in reverse. In one exemplary embodiment of the present invention, pitting and rod-wear data is collected while the tubing 125 moves uphole, and the tubing 125 is monitored for cracks as the tubing 125 moves downhole.

Turning now to FIGS. 10 and 11, FIG. 10 illustrates a flowchart of a process 950 for filtering data that characterizes tubing 125 according to an exemplary embodiment of the present invention. FIG. 11 illustrates a graphical plot 1100 and an accompanying table 1150 of raw data samples 1155 and filtered data samples 1160, 1165 according to an exemplary embodiment of the present invention. As discussed above, FIGS. 10 and 11 illustrate an exemplary embodiment of step 950 of process 900.

At step 1005, the pitting filter module 275 begins processing the digital samples 1155 that it received at step 945 of process 900. The table 1150 of FIG. 5B provides simulated digital samples 1155 as an example. The pitting filter module 275 places the samples 1155 in a buffer, a memory array, or some other storage facility. For example, a memory device may hold one sample 1155 per table cell or per memory register.

At step 1010, the encoder 115 measures the speed of the tubing 125 and outputs the speed measurement to the pitting filter module 275 via. the communication link. 120. Thus, the pitting filter module 275 has access to information about the speed of the tubing 125 throughout each extraction increment. As discussed above, the tubing's extraction speed may fluctuate, may change in an uncontrolled manner, or may be erratic.

At step 1015, the pitting filter module 275 compares the measured tubing speed to a speed threshold. The speed threshold can be a setting input by an operator, technician, or engineer via the laptop 130. Alternatively, the speed threshold can be software generated, for example derived from an assessment of the pitting sensor's performance and/or responsiveness. Moreover, the speed threshold can be determined empirically or based on a calibration procedure, a standardization process, a rule, or some protocol or procedure.

The flow of process 950 branches at inquiry step 1020 according to whether the measured speed is greater that the speed threshold. If the measured speed is greater than the speed threshold, then step 1025 follows step 1020, if the measured speed is not greater than the speed threshold, then step 1030 follows step 1020. After executing one of step 1030 and 1025, process 950 loops back to step 1005 and continues digitally processing sensor samples 555. Step 430 applies a greater level of filtering or averaging than step 425 applies.

Thus, at lower speeds, the pitting filter module 275 applies more filtering than it applies at higher speeds. In other words, the pitting filter module 275 applies greater smoothing or averaging in response to a tubing speed decrease or in response to the tubing speed dropping below a threshold or a limit.

As discussed above, process 900 typically executes step 950 without waiting for the flow of process 950 to exit the iterative loop shown in FIG. 10. For example, process 950 may run in the background, with process 900 obtaining output from process 950 on an as-needed basis. Moreover, process 900 may stop and start process 950, as step 950, for example causing process 950 to perform a predetermined number of iterative cycles or halting its execution after achieving some computational result.

In an alternative exemplary embodiment of the present invention, step 1020 is adapted, relative to the version illustrated on FIG. 10, to compare the current speed to a band or a range of speeds. If the current speed is above the band, then step 1025 follows step 1020 as a first filtering mode. If the current speed is below the band, then, step 1030 follows step 1025 as a second filtering mode. If the current speed is within the band, then process 950 selects another step (not shown in FIG. 10) as a third filtering mode.

In one embodiment, that third filtering mode may alternatively provide a level of filtering somewhere between the filtering of the first mode and the filtering of the second mode. The third filtering mode can also comprise a refined filtering approach or a user-selected level of filtering, for example.

The third filtering mode may alternatively comprise the last filtering mode used prior to the speed entering the band. In other words, the speed band has an upper speed threshold at the top of the band and a lower speed threshold at the bottom of the band. If the current speed is greater than the upper speed threshold, the filter module 275 applies the first filtering mode. If the current speed then drops below the upper speed threshold without falling below the lower speed threshold, the filter module 275 continues applying the first filtering mode. If the current speed then drops below the lower threshold (from within the band), the filter module 275 applies the second filtering mode. If the speed then increases back into the band, the filter module 275 continues applying the second filtering mode until the speed increases above the band. Thus, in this embodiment, the filter module 275 can be viewed as using a "dead band" as a criterion for selecting a filtering mode or state.

Referring now to the flowchart FIG. 10, at step 1025, which executes in response to the tubing speed being above the speed threshold, the pitting filter module 275 applies a first level of filtering or averaging to the raw data 1155 In one exemplary embodiment, the digital signal processing of step 1025 comprises averaging a number "N" of the samples 1155. The number "N" may be set to one or two, for example.

For example, as shown in the table 1150 of FIG. 11B, the pitting filter module 275 can average two of the samples 1155 using the computation or equation shown immediately below. In this computation "$FS_i$" denotes the current filtered sample 1160, "$S_i$" denotes the current raw sample 1155, and "$S_{i-1}$" denotes the raw sample 1155 acquired immediately before the current raw sample 1155.

$$FS_i=(S_i+S_{i-1})/2$$

As shown in the plot 1110 of the level-one-filtered data samples 1160, the level-one filtering suppresses or smoothes some of the peaks present in the raw data plot 1105, while retaining the raw data plot's general structure.

If the tubing 125 is moving rapidly, low filtering or no filtering may be appropriate. The motion of the tubing through the measurement zone 155 can, itself, smooth the data 1155. In other words, in many circumstances, spikes present in raw data 1155 obtained from a fast-moving tubing 125 can be attributable to valid tubing conditions, may be of interest to the operator, and may bear on grading the tubing 125.

At step 1030, which process 950 executes in response to the tubing speed being below the speed threshold, the pitting filter module 275 applies a second, higher level of filtering or averaging to the raw data 1155. In one exemplary embodiment, the digital signal processing of step 1030 comprises averaging a number "M" of the samples 1155, wherein M is greater than N(M>N). The number "M" may be set to three, for example.

Figures 11A, 11B:
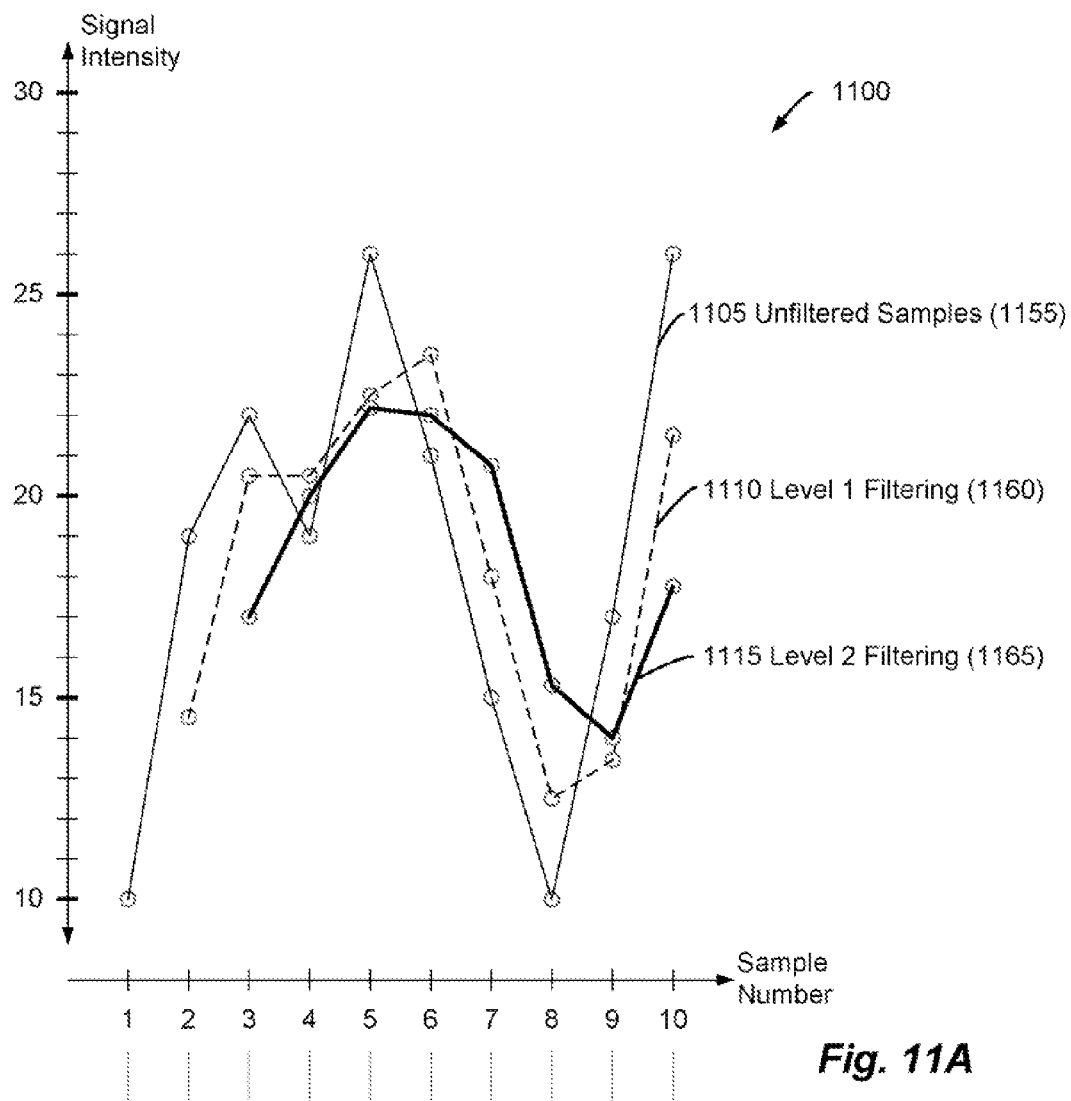
FIGS. 11A and 11B, collectively

For example, as shown in the table 1150 of FIG. 11B, the pitting filter module 275 can average three of the samples 1155 using the following computation:

$$FS_i=(S_i+S_{i-1}+S_{i-2})/3$$

The symbols of this equation follow the same conventions of the equation of step 1025, discussed above. As shown in the plot 1115 of the level-two-filtered data samples 1165, the level-two filtering further suppresses or smoothes the peaks present in the raw data plot 1105.

With the tubing string 125 moving very slowly or stopped, level-two suppression can suppress high-frequency components of the raw data 1155. Such spikes could be attributed to noise, an extraneous effect, or some influence that is not directly related to grading the tubing 125. In one embodiment of the present invention, process 950 applies a third level of suppression when the tubing string 125 is stopped. That third level can further smooth signal spikes, for example by setting M to five, ten, or twenty.

Process 950 may be viewed as a method for changing the filtering in response to a speed event or a noise event. While process 950 provides two discrete levels of filtering, other embodiments may implement more filtering levels, such as three, ten, one hundred, etc. In one embodiment, the number of levels is large enough to approximate continuity, to be continuous, or to provide an essentially unlimited number of levels.

In one exemplary embodiment, process 950 can be viewed as a rule-based method for digitally processing signals. Moreover, process 950 can be viewed as a method for filtering the output of the pitting sensor 255 using two filtering modes, wherein a specific mode is selected based on an event related to signal integrity, fidelity, noise, or quality.

In one exemplary embodiment of the present invention, the motion of the tube 125 provides a first filtering or signal averaging, and the pitting filter module 275 provides a second filtering or signal averaging. Thus, the total filtering is the aggregate or net of the first filtering and the second filtering. A computer-based process can adjust that second filtering to offset or compensate for changes in the first filtering due to speed variations. In response to the computer adjustments of the second filtering, the net filtering may remain relatively constant or uniform despite fluctuations in tubing speed In one exemplary embodiment, the tubing scanner 150 flexibly filters sensor signals while the signals are in the analog domain. For example, the pitting sensor electronics 270 can comprise an adaptive filter that applies a variable amount of analog filtering to analog signals from the pitting transducer 260. That is, the sensor electronics 270 can process the analog pitting signal using a time constant that is set according to encoder input, speed, noise, or some other criterion, rule, or parameter. Accordingly, adaptive filtering can occur exclusively in the digital domain, exclusively in the analog domain, or in both the analog and the digital domain.

Figure 12:
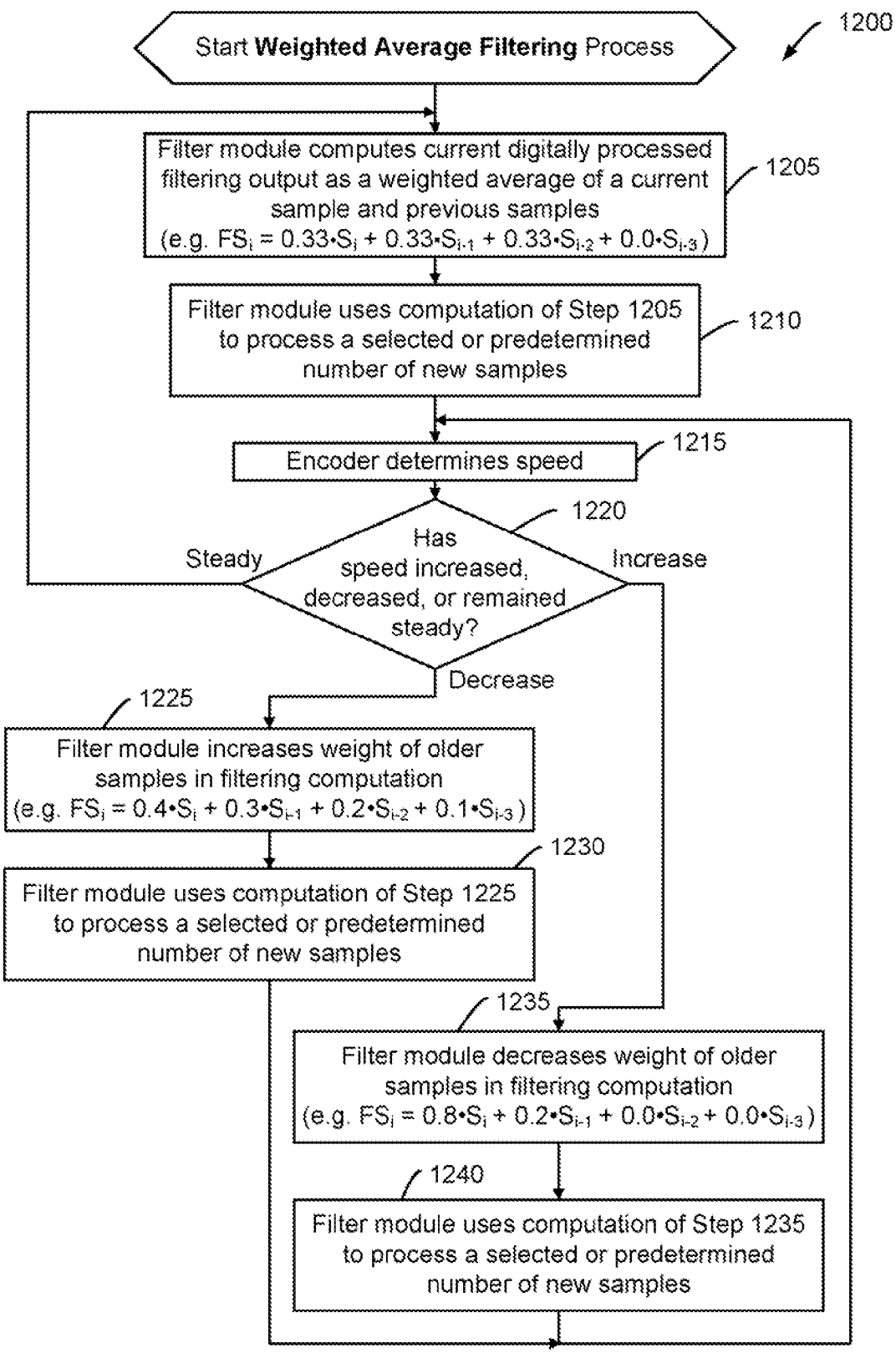
FIG. 12 is a flowchart of an exemplary process for filtering tubing data using an adaptive filter in accordance with an embodiment of the present invention.
Figures 13A, 13B:
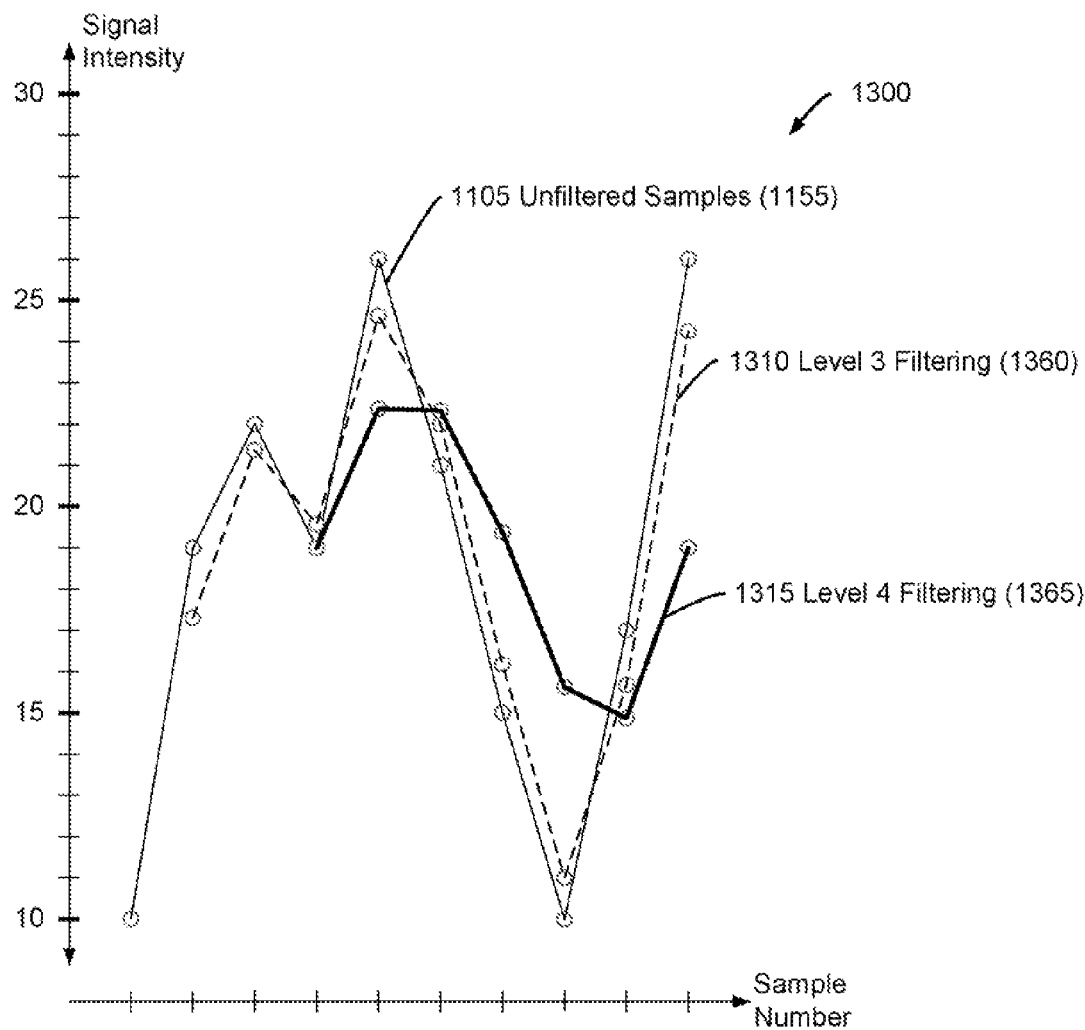
FIGS. 13A and 13B, collectively

Turning now to FIGS. 12 and 13, FIG. 12 illustrates a flowchart of a process 1200 for filtering tubing data 1155 using an adaptive filter according to an exemplary embodiment of the present invention. FIG. 7 illustrates a graphical plot 1300 and an accompanying table 1350 of raw tubing data 1155 and adaptively filtered tubing data 1360, 1365 according to an exemplar)1 embodiment of the present invention.

Although process 1200, which is entitled Weighted Average Filtering, will be discussed with exemplary reference to the pitting sensor 255, the method is applicable to the rod-wear sensor 205 or to some other sensing device that monitors tubing.

In one exemplary embodiment of the present invention, process 1200 can be implemented as step 950 of process 900, discussed above and illustrated in FIG. 3. That is, process 900 can execute process 1200 as an alternative to executing process 950 as illustrated in FIGS. 4 and 5 and discussed above.

Process 1200 outputs filtered signal samples 1165, 1360, 1365 that are each a weighted composite of four raw signal samples 1355.

At step 1205, the pitting filter module 275 computes a current processed sample 1165 as a weighted average of a present or current sample and three earlier samples. That is, the output is based on the most recently acquired sample and the three immediately-preceding samples, wherein three is an exemplary rather than restrictive number of samples.

For example, the pitting filter module 275 can apply the following computation to the raw data 1155 as a basis for generating each filtered sample output (FS$_i$) 1165 in a series of outputs 1165:

$$FS_i=0.33 \cdot S_i+0.33 \cdot S_{i-1}+0.33 \cdot S_{i-2}+0.0 \cdot S_{i-3}$$

In this equation, "$FS_i$" denotes the current filtered sample, "$S_i$" denotes the current raw sample 1155, and "$S_{i-1}$," "$S_{i-2}$," and "$S_{i-3}$" denote the three samples 1155 that arrive in series at the pitting filter module 275 in advance of the current sample 1155. FIG. 5A, discussed above, provides a plot 1115 and a data table 1165 of the results of this equation. In other words, the computation of step 1030 of process 950 provides an equivalent computation to the computation of step 1205 of process 1200.

At step 1210, the pitting filter module 275 uses the computation of step 1205 to produce a predetermined or a selected number of outputs, such as ten or one hundred, for example. Process 1200 can implement step 1210 by iterating step 1205 a fixed number of times or for a fixed amount of time. In one exemplary embodiment of the present invention, process 1200 iterates step 1205 until an event occurs; until the signal exhibits a predetermined characteristic, such as a frequency content; or until a signal processing objective, such as a stabilization criterion, is met.

At step 1215, the encoder 115 determines the tubing speed and forwards that speed to the pitting filter module 275.

At inquiry step 1220, the pitting filter module 275 applies a rule to the tubing speed, specifically determining whether the speed has increased, decreased, or remained steady, for example for a period of time. The period of time can comprise a fixed time, a configurable time, or an amount of time that varies according to a rule.

Determining whether the speed remains steady can comprise determining whether the speed remains within a speed region or a band of acceptable speeds. That is, the determination of inquiry step 1220 can be based on whether the actual speed is between two levels or thresholds. The determination of step 1220 can further comprise evaluating whether the speed is uniform, constant, consistent, smooth, or within a band of normalcy, for example.

If the speed is steady, as determined at step 1220, process 1200 iterates steps 1205 1210, 1215, and 1220 thereby using, or continuing to use, the equation of step 1205 to digitally process incoming sensor samples.

If the pitting filter module 275 determines that the speed has decreased rather than remained constant, then process 1200 executes step 1225 following step 1220. At step 1225, the filtering module 225 applies a filtering computation to the raw data 1155 that increases the weight of older samples 1155 or that includes a contribution of older samples 1155. For example, the pitting filter module 275 may use the following computation:

$$FS_i = 0.4 \cdot S_i + 0.3 \cdot S_{i-1} + 0.2 \cdot S_{i-2} + 0.1 \cdot S_{i-3}$$

The results 1365 of this equation are tabulated in table 1350 and presented graphically via the trace 1315 (arbitrarily labeled "Level 4 Filtering") of the plot 1300. The symbols of this equation follow the same notational conventions of the equation of step 1205, discussed above.

At step 1230, the pitting filter module 275 generates multiple filtered output samples 1365 using the computation of step 1225. The number of generated samples can be ten, fifty, one hundred, or one thousand, for example. Process 1200 can iterate step 1225 to achieve step 1230. The number of iterations can be based on time, output, or a number of cycles. In one exemplary embodiment of the present invention, process 1200 iterates step 1225 until an event occurs, until the filtered signal exhibits a predetermined characteristic, such as a frequency content, or until meeting a signal processing objective, such as a stabilization criterion.

Following step 1230, process 1200 loops back to step 1215 to check the tubing speed and to inquire, at step 1220, whether the tubing speed is increasing, decreasing, or remaining constant.

If the pitting filter module 275 determines, at step 1220, that the tubing speed is increasing rather than decreasing or remaining constant, then step 1235 follows step 1220. At step 1235, the pitting filter module 275 increases the contribution of the more recent samples 1155 in the filtering computation. For example, the pitting filter module 275 might apply the following computation to the raw data samples 1155:

$$FS_i = 0.8 \cdot S_i + 0.2 \cdot S_{i-1} + 0.0 \cdot S_{i-2} + 0.0 \cdot S_{i-3}$$

The row 1360 of the table 1350 provides a representative output of this computation using the raw sensor data 1155. The trace 1310, arbitrarily labeled "Level 3 Filtering" shows the filtered data 1360 in graphical form. This computation follows the same symbolic notation of the equations of steps 1205 and 1225, which are discussed above.

At step 1240, the pitting filter module 275 applies the computation of step 1235 to the incoming data samples 1155, executing at each new data element 1155, to generate the filtered output samples 1360. The pitting filter module 275 can generate either a fixed or a flexible number of filtered samples 1360, such as ten, fifty, one hundred, ten thousand, etc. Process 1200 can repeat or iteratively execute step 1235 to achieve step 1240. The number of iterations can be based on time or a number of cycles. In one exemplary embodiment of the present invention, process 1200 repeats step 1235 until an event occurs, or until the filtered signal exhibits a predetermined characteristic, such as a frequency content, or until meeting a signal processing objective, such as a stabilization criterion.

Following the execution of step 1240, process 1200 loops back to step 1215, obtains a fresh speed measurement, executes inquiry step 1220 to determine whether a speed change event has occurred, and proceeds accordingly.

Figure 14:
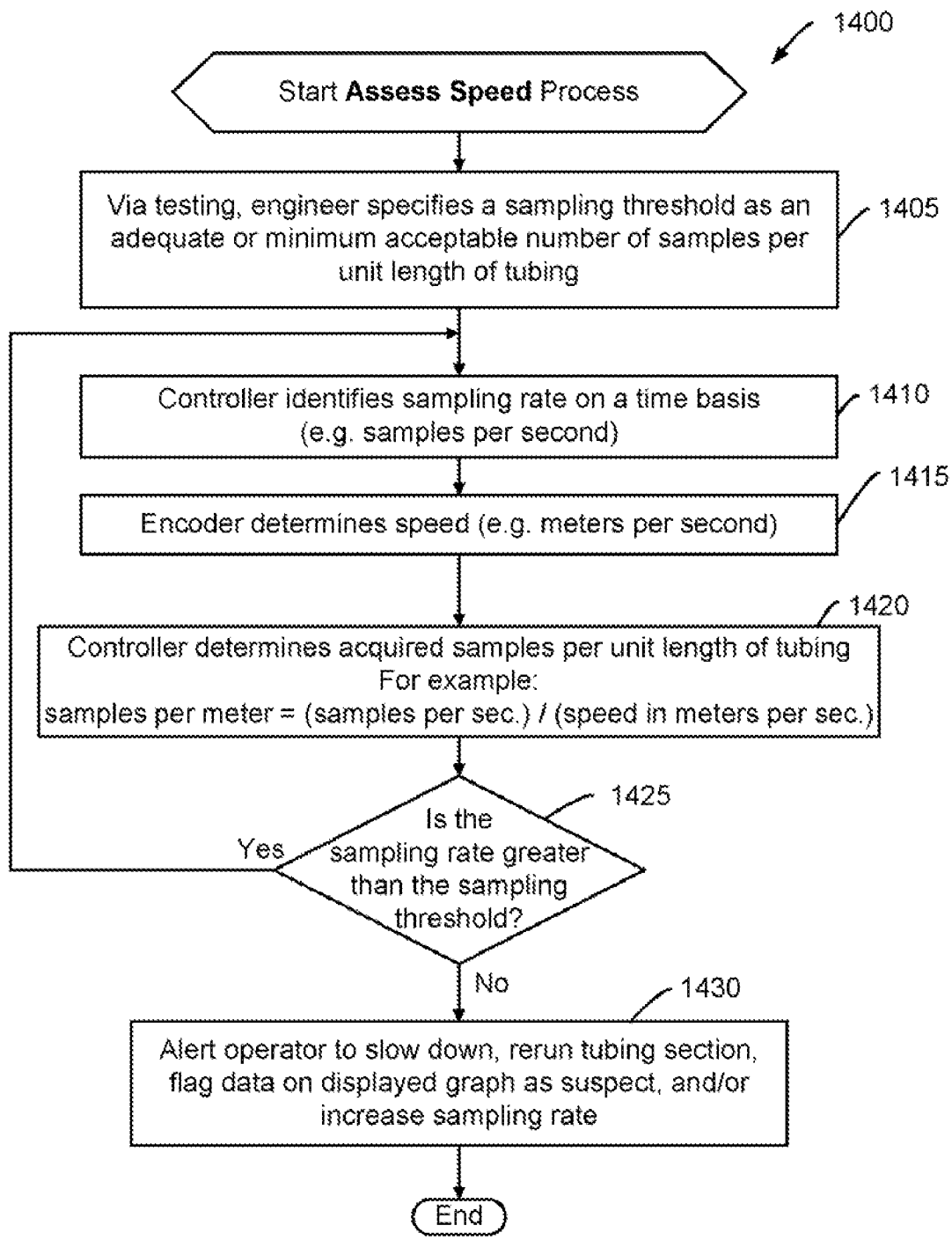
FIG. 14 is a flowchart of an exemplary process for evaluating a sampling rate of data obtained from a tubing sensor in accordance with an embodiment of the present invention.

Turning now to FIG. 14, this figure illustrates a flowchart of a process 1400 for evaluating a sampling rate of data obtained from a tubing sensor according to an exemplary embodiment of the present invention. The tubing sensor can be the tubing scanner 150, the pitting sensor 255, the rod-wear sensor 205, a collar locator, an inventory counter, an imaging apparatus, or some other monitoring or evaluating device or detection system, for example.

Process 1400, which is entitled Assess Speed, will be described in the exemplary situation of the controller 250 performing certain of the method's steps. However, in an alternative embodiment, software executing on the laptop 130 implements various steps of process 1400.

Moreover, the instrumentation system 200, which comprises the laptop 130 and the controller 250, can perform process 1400 as an adjunct, complement, or supplement to the adaptive filtering of process 950 or process 1200. Alternatively, the instrumentation system 200 can perform process 1400, or a similar process, as an alternative to performing process 950 or process 1400, process 1400 can proceed with or without the filter modules 225, 275 performing digital signal processing tasks.

At step 1405, an engineer or some other person, tests the system 200 on various tubes to identify the tubing scanner's performance characteristics at various tubing speeds. Test pieces of tubing can have assorted defects, pits, cracks, and rod-wear conditions that are representative of real-world situations. That is, the tubing scanner 150 can be characterized by scanning standard pieces of tubing 125 that have well-defined defects. The testing can comprise moving tubes, each at a known stage of deterioration, at various speeds though the measurement zone 155 of the tubing scanner 150.

The engineer uses the empirical results of those tests to specify, define, or establish a sampling threshold for operating the tubing scanner 150. That is, the engineer specifies a minimum number of samples per unit length of tubing 125 that the tubing scanner 150 should acquire to obtain reliable or interpretable data. The engineer may also use the testing as a basis to specify a tubing speed limit, for example.

At step 1410, the controller 250 determines the actual sampling rate of the ADC 265 and the ADC 215. That is, during a routine service call, as illustrated in FIG. 1 and discussed above, the controller 250 determines the data sampling rate or data capture rate of the tubing scanner 200. The controller 250 may obtain this information by polling the ADCs 215, 265, or by measuring the passage of time between incoming samples, for example. The units of the sampling rate may be "samples per second," for example.

At step 1415, the encoder 115 measures the speed and provides the speed measurement to the controller 250.

At step 1420, the controller 250 determines the number of acquired samples that the ADCs 215, 265 are supplying on a length basis. That is, the controller 250 computes, based on the time between each sample and the speed of the tubing 125, how many samples that the tubing scanner 150 is producing in a given length of tubing 125.

Software executing on the controller 250 can compute the number of samples per meter of tubing as the sample rate (in samples per second) divided by the tubing speed (in meters per second). Thus, the controller 250 might employ the following equation to evaluate whether the tubing scanner 150 is generating a sufficient or adequate number of data samples per unit length of tubing:

no. of samples per meter=(no, of samples per sec)/
(tubing speed in meters per sec.)

At inquiry step 1425, the controller 250 determines whether the actual, computed sampling rate is greater than the sampling threshold specified at step 1405, if the actual sampling rate is greater than the threshold, then at step 1425, process 1400 loops to step 1410. Thereafter, process 1400 continues monitoring the sampling rate to evaluate whether an adequate number of samples are being obtained from the tubing 125.

If the ADCs 215, 265 operate at a fixed sampling rate, then inquiry step 1425 can be viewed as assessing whether the tubing speed is within a range of acceptability.

If, at step 1425, the controller 250 determines that the tubing scanner is obtaining an insufficient number of samples of the tubing 125, then execution of step 1430 follows step 1425. At step 1430, the controller 250 takes corrective action to the under sampling condition. The controller 250 can alert the operator of the reel 110 to slow down. In one embodiment, the controller 250 automatically slows the rotational speed of the reel 110, for example via a feedback loop.

In one embodiment, the controller 250 may instruct the service crew to lower one or more sections of the tubing 125 back into the well 175, for example to re-scan a section from which an insufficient number of samples have been collected. Alternatively, the crew may elect to physically mark a section of the tubing 125 that has been identified as being associated with data of suspect quality. In one exemplary embodiment, the controller 250 sends notification to the laptop 130 that certain data is questionable or may not be reliable. The laptop 130 can mark the suspect data as potentially unreliable and can present a label on a graph of the data to highlight any suspect data. Moreover, a graphing capability, such as provided by the data management module discussed above, of the laptop 130 may overlay a confidence indicator upon the graphical data. The overlay may indicate the relative or absolute confidence of various portions of the graph according to the sampling rate.

In one exemplary embodiment of the present invention, the controller 250 sends a feedback signal to the ADCs 215, 265 upon an occurrence of a sampling rate incursion. That is, the controller 250 notifies the ADCs 215, 265 to increase their respective sampling rates if a section of tubing 125 is under sampled. The controller 250 can also increase the sampling rate of the ADCs 215, 265 if the number of samples per unit length is trending towards an unacceptable value.

Following step 1430, process 1400 ends. Process 1400 can be viewed, as a method for taking corrective action if the tubing scanner 150 fails to collect an adequate or sufficient number of measurement samples from a section of the tubing 125.

Figure 15:
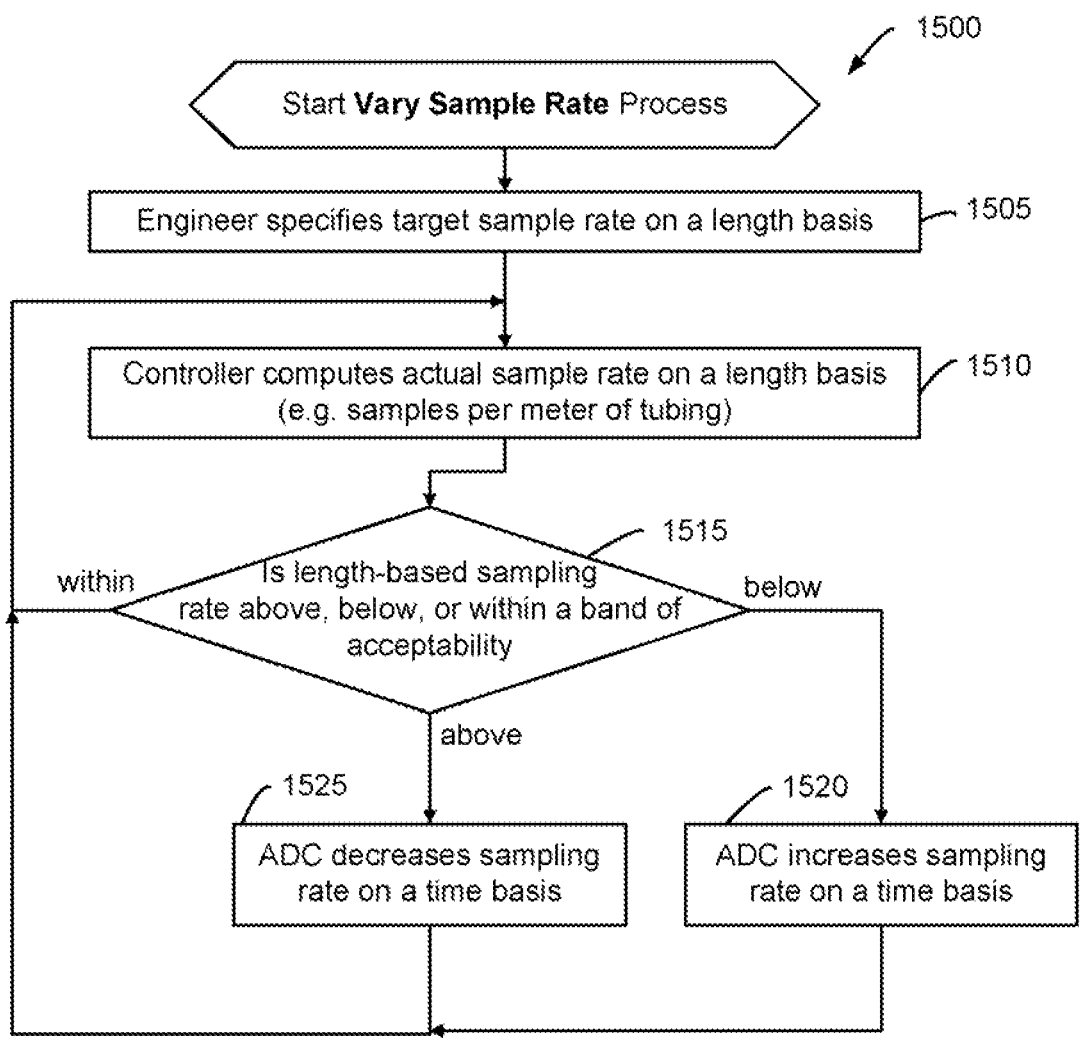
FIG. 15 is a flowchart of an exemplary process for varying a rate of obtaining data samples from a tubing sensor in accordance with an embodiment of the present invention.

Turning now to FIG. 15, this figure illustrates a flowchart of a process 1500 for varying a rate of obtaining data samples from a tubing sensor according to an exemplary embodiment of the present invention. Process 1500, which is entitled Vary Sample Rate, illustrates a method through which the tubing scanner 150 can adjust a rate of sample acquisition based on a rule or an application of a criterion.

At step 1505, an engineer specifies a target sampling rate on a length basis. As discussed above, the engineer can conduct testing to evaluate the number of samples that the tubing scanner 150 should collect from each unit length of the tubing 125 to ensure adequate data representation.

The analysis can proceed according to the principles of the Nyquist Theorem. In accordance with that theorem, the sampling should be greater than the Nyquist rate to avoid aliasing. In other words, the tubing 125 should be sampled at a frequency that is at least twice the frequency of any variation in the tubing 125 that may be relevant to evaluating or grading the tubing 125.

For example, if the tubing scanner 150 is to reliably detect tubing wall variations that are one millimeter in length and larger, then the minimum acceptable sampling rate might be specified as two samples per millimeter.

Moreover, the engineer may specify a band or range of acceptable sampling rates, wherein rates above or below the specified band are unacceptable. The sampling rate criterion can be based upon sensor resolution, for example to provide data with adequate resolution to discern features relative to a quality assessment.

At step 1510, the controller 250, or a software program executing thereon, computes the actual sampling rate on a length basis according to the time span between each sample and the speed of the tubing 125. The computation can proceed as discussed above with reference to step 1420 of process 1400, for example.

At inquiry step 1515, the controller 250 compares the actual length-based sampling rate, determined at step 1510, to the specifications defined at step 1505. Step 1515 branches the flow of process 1500 according to whether the actual sampling rate is above, below, or within a range of acceptable values.

If the sampling rate is with the acceptable range, then process 1500 avoids altering the sampling rate and, via iterating steps 1510 and 1515, continues monitoring the sampling rate to ensure that it remains within the acceptable range.

If the sampling rate is too low, then process 1500 executes step 1520. At step 1520, the controller 250 transmits a signal or command to either or both of the ADCs 215, 265. In response to that signal or command, the signaled ADC 215, 265 increases the sampling rate, typically by shortening the time between each sample acquisition.

If the controller 250 determines that the sampling rate is too high at step 1515, then execution of step 1525 follows execution of step 1515. At step 1515, the controller 250 signals the appropriate ADCs 215, 265 to decrease the sampling rate on a time basis. That is, one or both of the ADCs 215, 265 lengthen the time between each sample. One motivation to avoid an excessively high sampling rate is to conserve memory, computer processing resources, or communication bandwidth of the sampled data.

Following execution of either of steps 1520 and 1525, process 1500 loops back to step 1510 and continues monitoring the sampling rate to ensure compliance with specifications or operating parameters.

Section III: Methods for Displaying Depth Data

Turning now to FIG. 316, an exemplary process 1600 for overlaying a display of depth on an analysis data chart based on the position of the collars 157 is shown and described within the operating environment of the workover rig 140 and tubing scanner 150 of FIGS. 1 and 2. Now referring to FIGS.

1, 2, and 16, the exemplary method 1600 begins at the START step and proceeds to step 1605, where the workover rig 140 begins to remove the tubing 125 from the well 175. In step 310, the computer 130 receives analysis data from the tubing scanner 150. In one exemplary embodiment, the computer 130 receives data from the pitting sensors 255 and the rod wear sensors 205.

In step 1615, an inquiry is made to determine if collar locators 292 have detected or sensed a collar 157. In one embodiment, the collar locators 292 detect a collar 157 when the collar 157 is adjacent or nearly adjacent to the collar locators 292. In another embodiment, the collar 157 can be detected by other sensors within the tubing scanner 150. For example, sensors 205 or 252 may be used to sense for collars as well as other function because the these sensors 205, 252 tend to resister a noticeable signal variation when a collar 157 passes within range of the sensor. The computer 130 can be programmed to recognize this variation or the operator of the rig 140 may be able to view the variation and register the location of the collar 157 through the computer 130 or other device communicably attached to the computer 130. If the collar locators 292 have detected a collar 157, the "YES" branch is followed to step 320, where the computer 130 marks the analysis data to designate that a collar was detected at that time. The computer 130 can "mark" the analysis data by inserting a figure, text, or symbol that can be later detected in the chart display of the analysis data. In the alternative, the computer 130 can "mark" the analysis data by recording the analysis data in a database, such as in a database table that can accept reference to the collar 157 being detected and associate that table with the time that the analysis data was being retrieved. Further, those of ordinary skill in the art of data retrieval, analysis and manipulation will know of several other methods for signifying that a collar 157 was located at a particular time that analysis data was being received from the tubing scanner 150. The process then continues to step 1625.

If the collar locators 292 do not detect a collar 157, the "NO" branch is followed to step 1625. In step 1625, an inquiry is conducted to determine if the tubing removal process from the well 175 is complete. If the tubing removal process is not complete, the "NO" branch is followed to step 1610 to receive additional analysis data and continue detecting collars 157. Otherwise, the "YES" branch is followed to step 1630, where the length of the tubing 125 being removed from the well 175 is determined. The tubing length can be input at the computer 130 by an oilfield service operator. Alternatively, the tubing length can be received from analysis completed by the encoder 115 or other positional sensor. In one embodiment, the tubing 125 has a length of thirty feet. The computer 130 receives the stored analysis data in step 1635. In step 1640, the computer 130 determines the position in the analysis data that the first collar 157 was removed from the well 175 by looking for the inserted mark.

In step 1645, a counter variable D is set equal to zero. The counter variable D represents the depth that the tubing 125 was at within the well 175. The computer 130 designates the first collar 157 marked in the analysis data as zero feet of depth in step 1650. In another embodiment, the depth of the first collar 157 marked in the analysis data can be input and can be other than zero feet. In another embodiment, positional data can be retrieved front the encoder 115 to determine the depth of the first collar 157. In step 1655, the computer 130 analyzes the analysis data to find the mark designating the next collar detected and marked within the analysis data. The computer 130 adds the length of the tubing 125 that was input by the operator or detected by the encoder 115 or other depth device to the current length D in step 360. For example, if the first collar 157 was at zero feet and the tubing 125 is in 30 foot lengths, then the new depth is 30 feet.

The computer 130 displays the analysis data chart and overlays the depth from D to D plus one between the two collar markers in step 1665. In step 1670, the counter variable D is set equal to D plus one. In step 1675, an inquiry is conducted by the computer 130 to determine if there are any additional collars 157 that were marked in the analysis data. If so, the "YES" branch is followed back to step 1655, where the computer 130 determines the position of the next collar marker in the analysis data. Otherwise, the "NO" branch is followed to step 1680, where the computer 130 displays the analysis data chart with the overlying depth chart. The process then continues to the END step.

Figure 16:
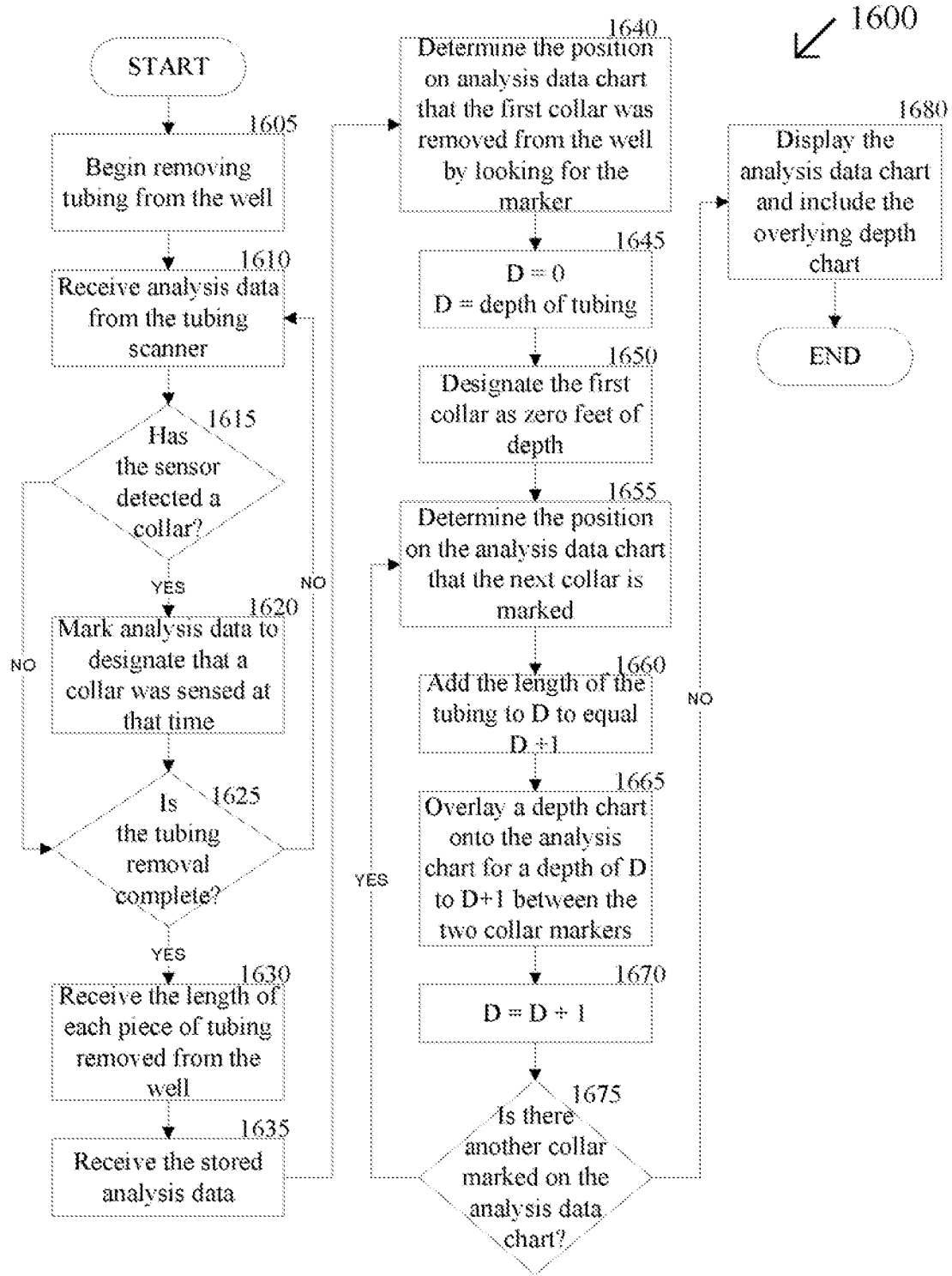
FIG. 16 is a flowchart diagram of an exemplary method for overlaying a display of depth on a analysis data chart based on the position of one or more collars in accordance with one exemplary embodiment of the present invention.
Figure 17:
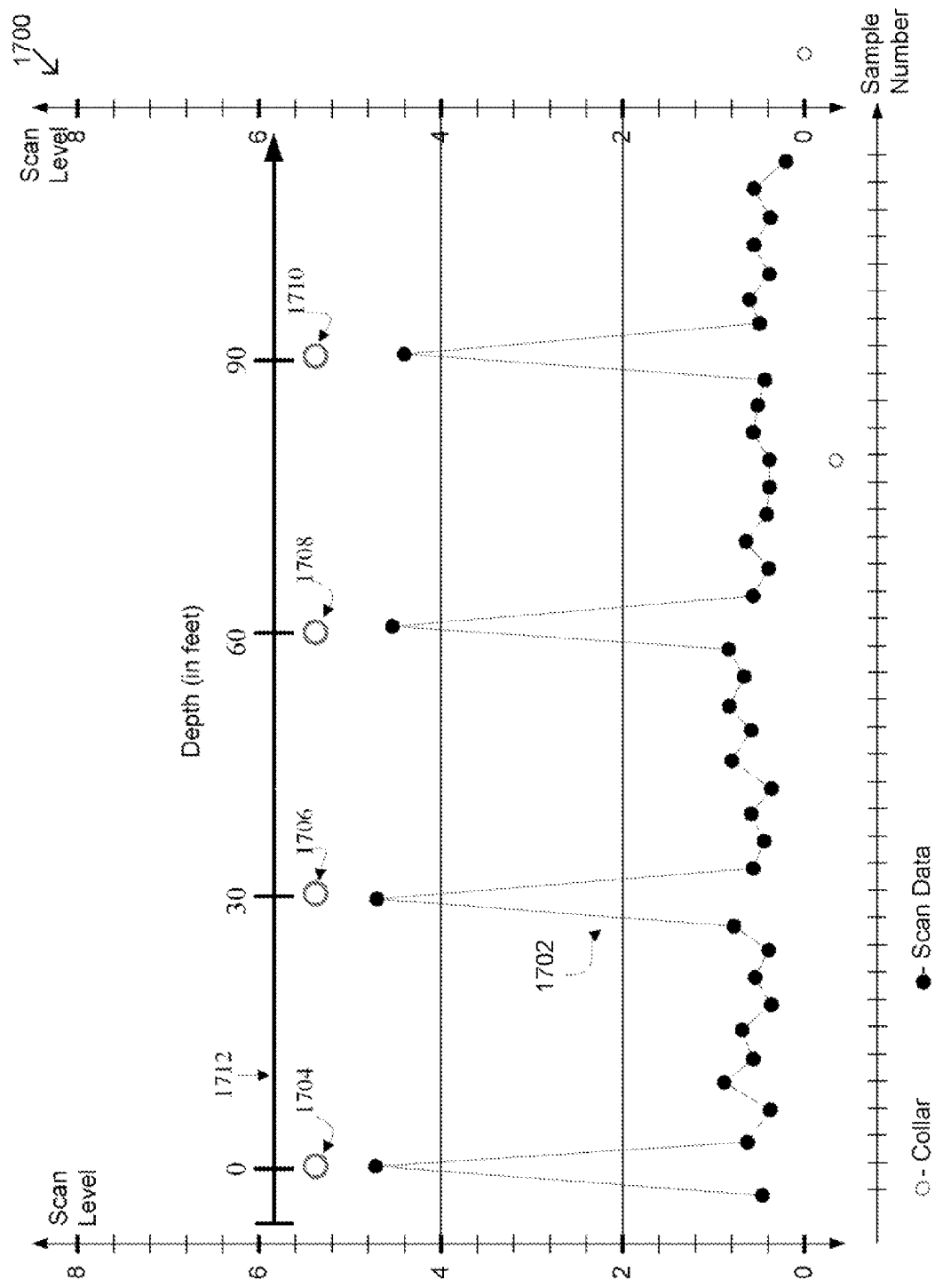
FIG. 17 is an exemplary chart showing the overlay of depth on an analysis data chart based on the position of the collars sensed by a collar locator sensor in accordance with one exemplary embodiment of the present invention.

FIG. 17 provides an view of the display methods of steps 1620 and 1640-1680 of FIG. 16. Referring to FIG. 4, the display of depth data overlying an analysis data chart based on collar position 1700 is generated based on an embodiment where the analysis data is being charted virtually simultaneous to retrieval. The analysis data is shown as scan data points 1702 in a line graph. When collars 157 are detected by the collar locators 292 and the information is passed from the collar locators 292 to the computer 130, the computer 130 inserts a mark 1704-1710. Once the tubing length and the position of the mark 1704 representing the first collar 157 detected have been determined, the computer 130 can begin generating the depth scale 1712. In the embodiment shown in FIG. 17, the first collar mark 1704 was determined to be at a depth of zero feet, however that depth can be adjusted as discussed above. The computer 130 determines the position of the next collar mark 1706 and marks the depth by extending the depth scale between the first collar mark 1704 and the second collar mark 1706 by the amount of the input tubing length. In one embodiment, the computer 130 could also insert subsets of the tubing length distance into the depth scale. For example, the computer 130 could estimate the position of ten feet and twenty feet on this scale to make exact depth easier to determine.

Once the computer 130 has determine the position of the second collar mark 1706, depth is set equal to thirty feet and the computer 130 determines the position of the third collar mark 1708. A tubing length of thirty feet is added to the distance D to equal a depth of sixty feet and the distance from thirty to sixty feet is extended between collar marks 1706 and 1708. The process can be repeated until the last collar mark is reached and the depth scale covers all or substantially all of the analysis data chart 1700. As discussed above, the method of display shown in FIG. 17 is only for exemplary purposes. Those of ordinary skill in the art could determine several other methods for marking the data once the collar 157 has been located and displaying the depth data with the analysis data without being outside the scope of this invention.

Figure 18:
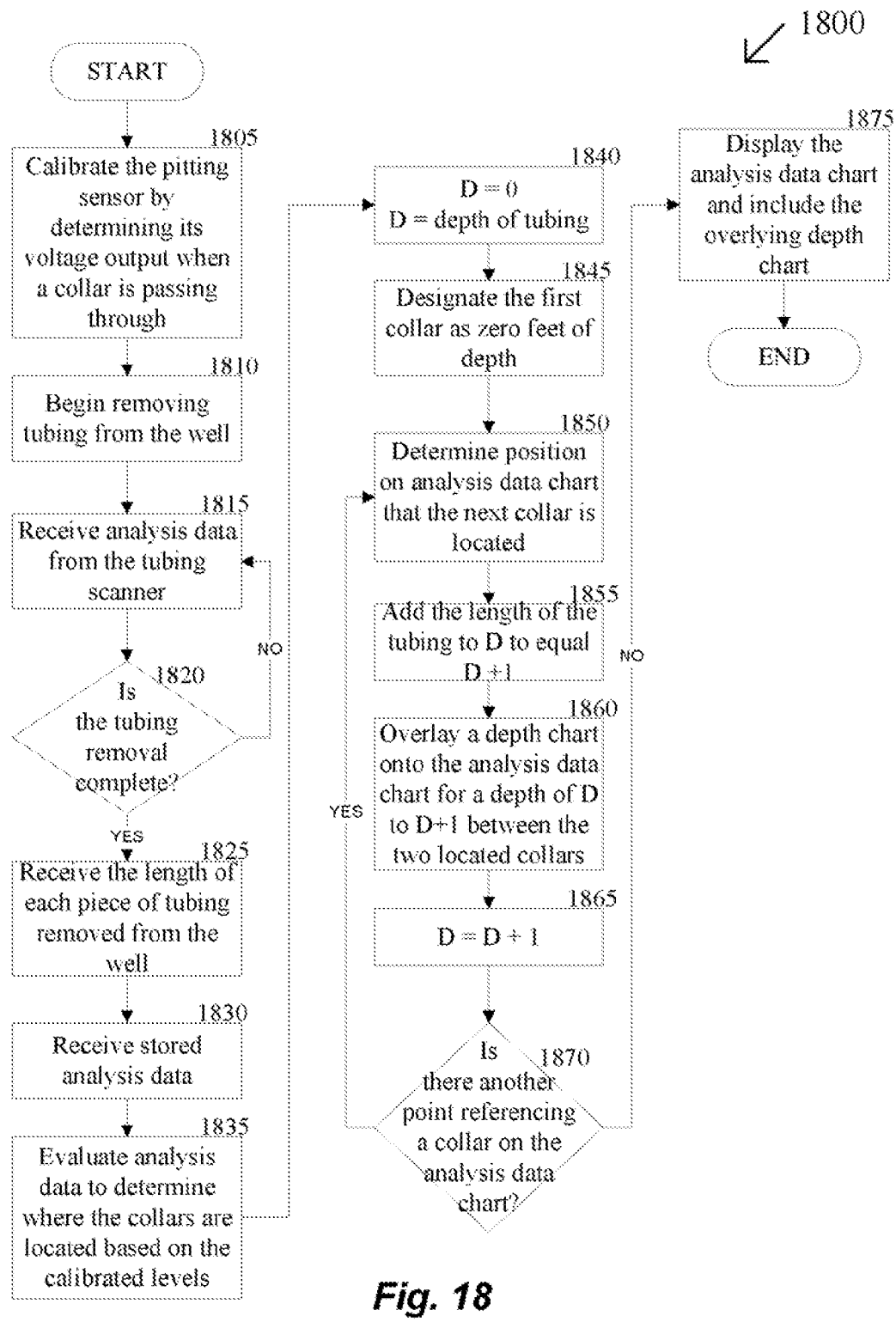
FIG. 18 is a flowchart diagram of another exemplary method for overlaying a display of depth on an analysis data chart by determining collar location based on calibration in accordance with one exemplary embodiment of the present invention.

FIG. 18 is a logical flowchart diagram illustrating another method 1800 for overlaying a display of depth on an analysis data chart based on the position of the collars 157 within the operating environment of the workover rig 140 and tubing scanner 150 of FIGS. 1 and 2. Referring to FIGS. 1, 2, and 18, the method 1800 begins at the START step and proceeds to step 1805, where a collar 157 is drawn through the pitting sensors 255 of the tubing scanner 150 to determine a calibrated or standard output by those sensors 255 when the sensors 255 sense a collar 157. In one embodiment, the collar 157 is drawn through the sensors 255 at or near the same speed that the tubing 125 will be analyzed to improve the acquisition of the scan level from the sensors 255. In another exemplary embodiment other sensors, such as the rod wear sensor 205 or pitting sensor 255 could be used in the calibration and detection of the collars 157. In yet another embodiment, the computer 130 may be programmed using fuzzy logic, neural networking program logic or other control and learning logic know to those of ordinary skill in the art in order to determine the output parameters of particular sensors when a collar 157 is passing within the sensing range of those sensors. The computer 130 could then calibrate itself to recognize when collars 157 are being sensed by particular sensors in the tubing scanner 150 and input that information into the output tables or charts.

In step 1810, the workover rig 140 begins to remove the tubing 125 from the well 175. In step 1815, the computer 130 receives analysis data from the tubing scanner 150. In one exemplary embodiment, the computer 130 receives data from the pitting sensors 255 and the rod wear sensors 205. In step 520, an inquiry is conducted to determine if the tubing removal process from the well 175 is complete. If the tubing removal process is not complete, the "NO" branch is followed to step 1815 to receive additional analysis data. Otherwise, the "YES" branch is followed to step 1825, where the length of the tubing 125 being removed from the well 175 is determined. The tubing length can be input at the computer 130 by an oilfield service operator. Alternatively, the tubing length can be received from analysis completed by the encoder 115, or other positional sensor, and passed to the computer 130. In one exemplary embodiment, the tubing 125 length is thirty feet. The computer 130 receives the stored analysis data in step 1830.

In step 1835, the computer 130 evaluates the analysis data to determine the location of the collars based on the levels obtained in the calibration procedure of step 1805. For example it may be determined during the calibration procedure that the scan level from the pitting sensors 255 is above four when a collar 157 is detected but otherwise it stays below four when tubing 125 with pitting is detected. In this example, the computer 130 would search the analysis data for data sequences above four and would mark these sequences as containing collars. Minor fluctuations in the scan levels could cause the analysis data to go above and below a scan level of four during the analysis phase. The computer 130 could also be programmed to evaluate this situation and determine if two collars have been located or one collar having multiple peaks over a scan level of four have been detected.

In step 1840, a counter variable D is set equal to zero. The counter variable D represents the depth that the tubing 125 was at within the well 175. The computer 130 designates the first collar 157 located in the analysis data as having a scan level above a predetermined level as zero feet of depth in step 1845, in another exemplary embodiment, the depth of the first collar 157 located by the computer 130 in the analysis data can be input and can be other than zero feet. In another exemplary embodiment, positional data can be retrieved from the encoder 115 or other positional sensor to determine the depth of the first collar 157. In step 1850, the computer 130 analyzes the analysis data to determine the position of the next collar 157 in the analysis data by analyzing the scan levels from the pitting sensor 255. The computer 130 adds the length of the tubing 125 that was input by the operator or detected by the encoder 115 to the current length D in step 1855. For example, if the first collar 157 was at zero feet and the tubing 125 is in thirty foot lengths, then the new depth is thirty feet.

The computer 130 displays the analysis data chart and overlays the depth from D to D plus one between the two located collars in step 1860. In step 1865, the counter variable D is set equal to D plus one. In step 1870, an inquiry is conducted by the computer 130 to determine if there is any additional analysis data from the pitting sensors 255 that is associated with a collar 157. If so, the "YES" branch is followed back to step 1850. Otherwise, the "NO" branch is followed to step 1875, where the computer 130 displays the analysis data chart with the overlying depth chart. The process then continues to the END step.

Figure 19:
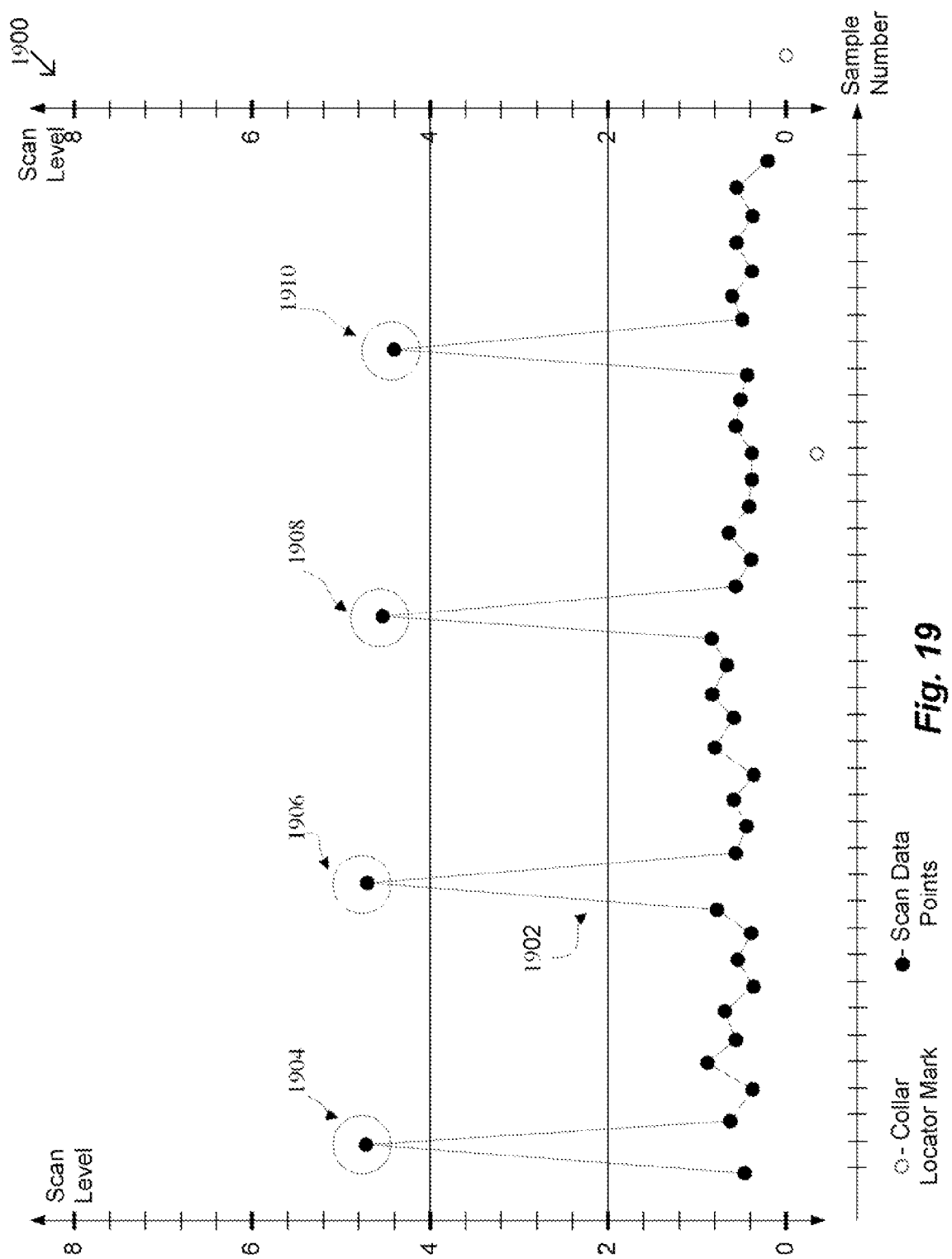
FIGS. 19 and 19A are exemplary charts showing the overlay of depth on an analysis data chart created by determining collar location based on prior calibration in accordance with one exemplary embodiment of the present invention.
Figure 19A:
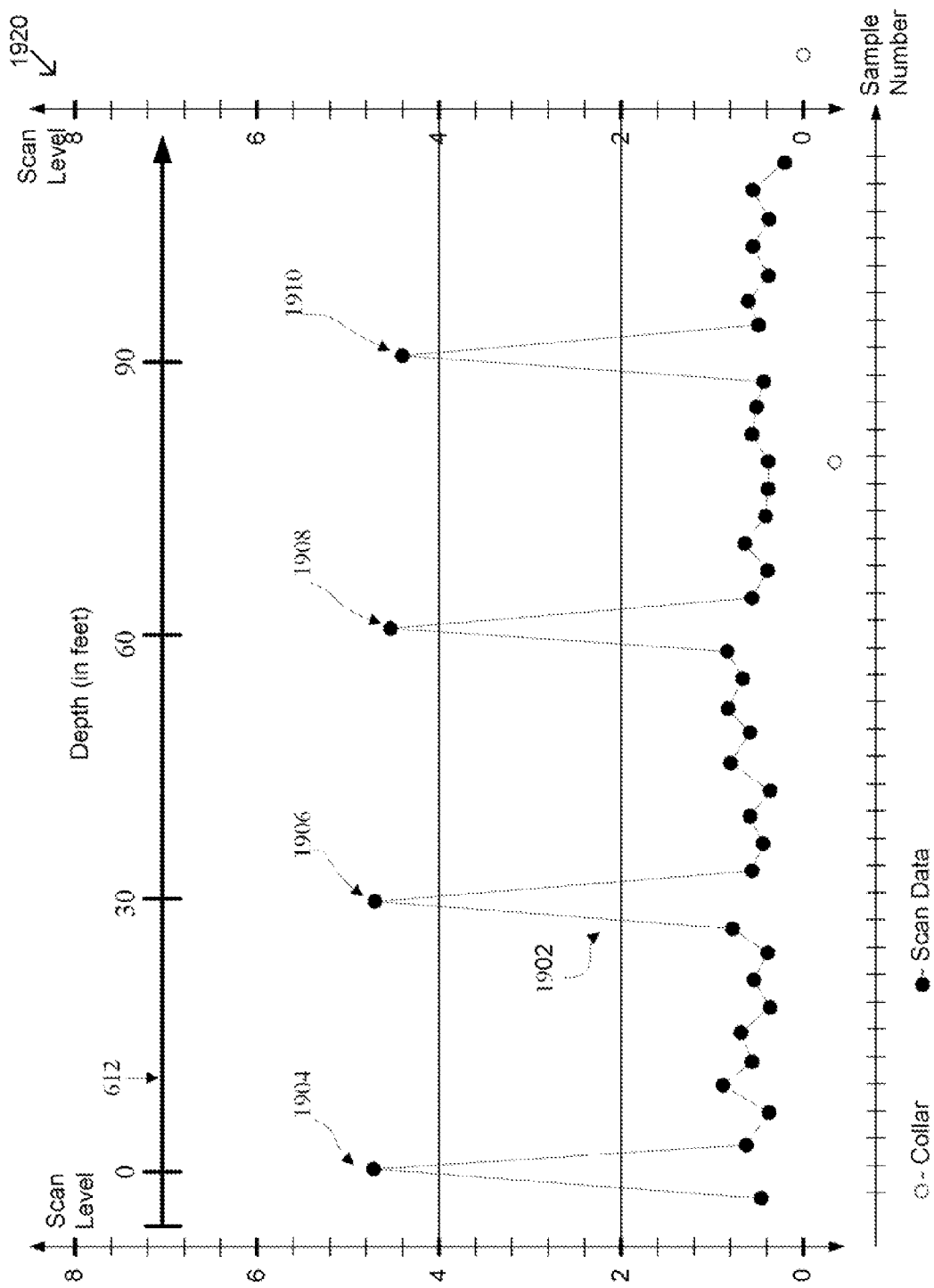

FIGS. 19 and 19A provide exemplary views of the display methods of steps 1835-1870 of FIG. 5. Now referring to FIGS. 18, 19, and 19A the exemplary display of depth data overlying an analysis data chart based on locating the collars 1900 begins with the display of the analysis data from the pitting sensors 255. The analysis data is shown as scan data points 1902 in a line graph. For this exemplary display 1900 it is assumed that the calibration step of 1805 in FIG. 5 revealed that the pitting sensors 255 output a scan level above four when the collar 157 was scanned and less than four when scanning all other parts of the tubing 125. The computer 130 analyzes the scan data 1902 to look for data points over a scan level of four.

When the computer 130 reaches the first data point 1904 having a scan level over four the computer 130 can record or highlight that data point as being a collar 157. In this exemplary display, the computer 130 associates the first collar 157 as having a depth of zero, but the initial depth of the first collar point 1904 can be other than zero, as discussed herein. The computer 130 can analyze the remainder of the analysis data to determine other collar points 1906, 1908, and 1910. Once the tubing length and the position of the first collar point 1904 representing the first collar 157 detected have been determined, the computer 130 can begin generating the depth scale.

FIG. 19A provides an exemplary view of the display of the analysis data chart 1920 with the depth scale overlying the analysis data. In the embodiment shown in FIG. 19A, the computer 130 determines the position of the next collar point 1906 and marks the depth by extending the depth scale between the first collar point 1904 and the second collar point 1906 by the amount of the input tubing length, thirty feet in this example. In one exemplary embodiment, the computer 130 could also insert subsets of the tubing length distance into the depth scale. For example, while not shown, the computer 130 could estimate the position often feet and twenty feet on this scale to make exact depth easier to determine for data points other than the collar points.

Once the computer 130 has determined the position of the second collar data point 1906, depth is set equal to thirty and the computer 130 determines the position of the third collar data point 1906. A tubing length of thirty is added to the distance to equal a depth of sixty feet and the distance from thirty to sixty feet is extended between collar data points 1906 and 1908. The process can be repeated until the last collar data point is reached and the depth scale covers all or substantially all of the analysis data chart 1920. As noted, the method of display shown in FIGS. 19 and 19A is only for exemplary purposes. Those of ordinary skill in the art could determine other methods for calibrating the sensors and determining the position of the collars based on the scan data and then, once the collars 157 had been located, display the depth data with the analysis data without being outside the scope of this invention. For example, in another exemplary embodiment, the analysis data and the depth data could be displayed on a vertically oriented chart instead of the horizontally oriented chart shown in FIGS. 19 and 19A.

Figure 20:
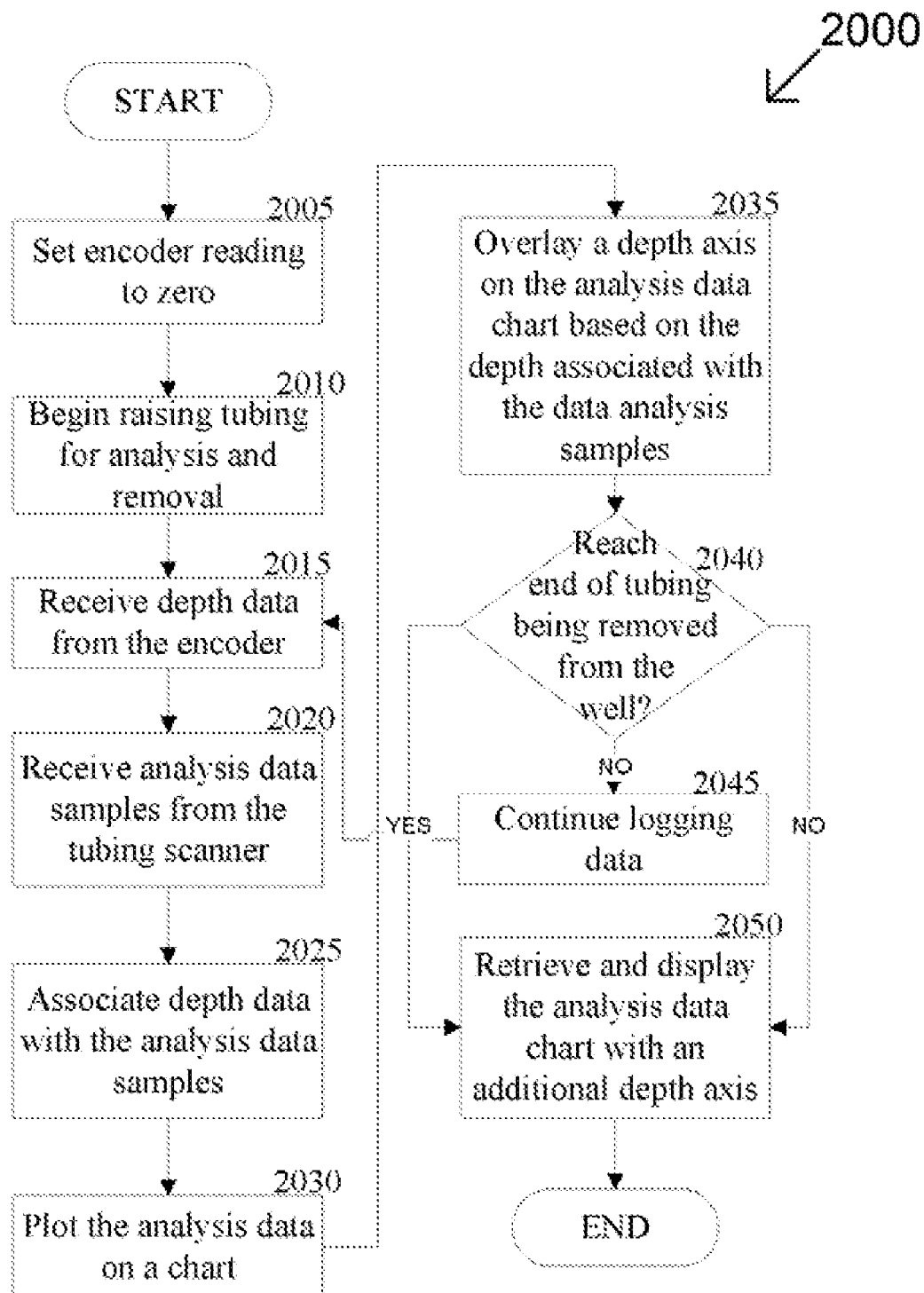
FIG. 20 is a flowchart diagram of an exemplary method for associating analysis data with the depth of the tubing that the analysis data was obtained from and displaying the analysis data with a depth component in accordance with one exemplary embodiment of the present invention.

FIG. 20 is a logical flowchart diagram illustrating a method 2000 for associating analysis data with the depth of the tubing 125 that the analysis data was obtained from and displaying the analysis data with a depth component within an exemplary operating environment of the workover rig 140 of FIG. 1 and the tubing scanner 150 of FIG. 2. Referencing FIGS. 1, 2, and 20, the method 2000 begins at the START step and proceeds to step 2005, where the encoder 115 reading at the computer 130 is set equal to zero. In step 2010, the workover rig 140 begins raising the tubing 125 from the well 175. The computer 130 receives positional or depth data from the encoder 115 or other positional sensor in step 2015. In step 2020, the computer 130 receives analysis data samples from the sensors 205, 255, 292 in the tubing scanner 150. In step 2025, the computer 130 associates the depth data from the encoder 115 with the analysis data samples. In one exemplary embodiment, each time the computer 130 receives an analysis data sample and stores it in a data fable, the computer 130 also receives a depth reading from the encoder 115 and places that data in a corresponding data table.

The computer 130 plots the analysis data on a chart and displays it on a view-screen for the oilfield service operator in step 2030. In step 2035, the computer 130 overlays a depth axis on the analysis data chart based on the depth associated with each data analysis sample in the data fables. In step 2040, an inquiry is conducted to determine if all of the tubing 125 has been removed from the well 175. If additional tubing 125 needs to be removed, the "YES" branch is followed to step 2045, where the computer 130 continues to log the data received from the encoder 115 and the tubing scanner 150. Otherwise, the "NO" branch is followed to step 2050, where the computer 130 retrieves and displays the analysis data chart with an overlying depth component. The process then continues to the END step.

Figure 21:
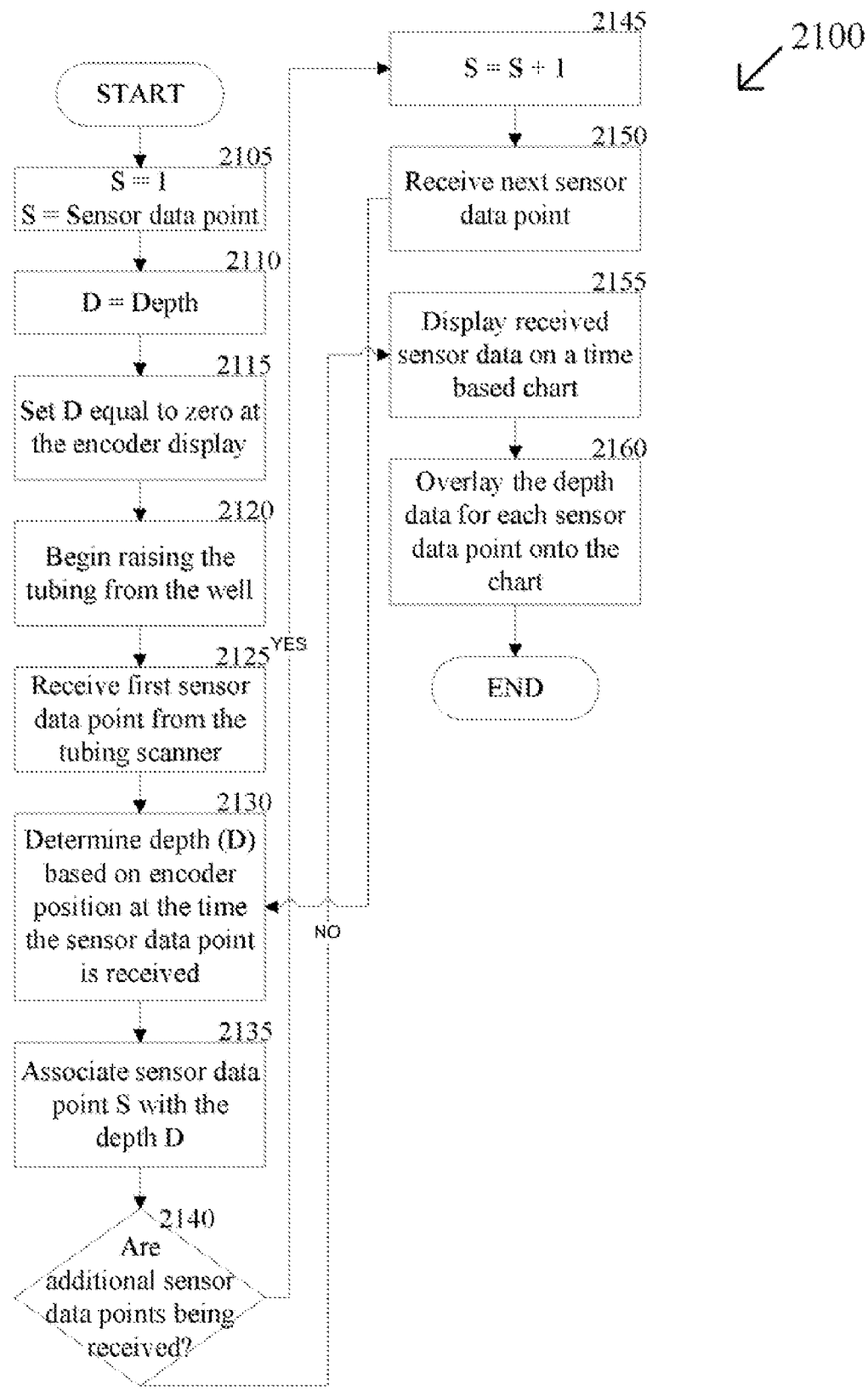
FIG. 21 is a flowchart diagram of another exemplary method for associating analysis data with the depth of the tubing that the analysis data was obtained from and displaying the analysis data with a depth component in accordance with one exemplary embodiment of the present invention.

FIG. 21 is a logical flowchart diagram illustrating another exemplary method 2100 for associating analysis data with the depth of the tubing 125 that the analysis data was obtained from and displaying the analysis data with a depth component within the exemplary operating environment of the workover rig 140 of FIG. 1 and the tubing scanner 150 of FIG. 2. Referencing FIGS. 1, 2, and 21, the exemplary method 2100 begins at the START step and proceeds to step 2105, where counter variable S is set equal to one. Counter variable S represents a sensor data point that can be received from the tubing scanner 150 and displayed on the analysis data chart. In step 2110, variable D represents the depth of the tubing 125 retrieved from the well 175. In one exemplary embodiment variable D represents the depth of the tubing 125 as it was positioned in the operating well 175 and not the variable position of each tubing section 125 as it is being removed from the well 175.

In step 2115, the variable D is set equal to zero. In one exemplary embodiment, the depth can be set equal to zero at an encoder display on the computer 130. In another exemplary embodiment, the encoder display can be located on the workover rig 140 and the computer 130 can receive and analyze the depth data form that encoder display through the use of communication means known to those of ordinary skill in the art. The workover rig 140 begins removing the tubing 125 from the well 175 in step 2120. In step 2125, the computer 130 receives the first sensor data point S from the tubing scanner 150. In one exemplary embodiment the data point can be from the pitting sensor 255, the rod wear sensor 205, the collar locators 292 or other sensors added to the tubing scanner 150. In step 2130 the computer 130 determines the depth D based on the encoder 115 position and display at the time the sensor data point is received. In one exemplary embodiment, the delay caused by the data from the tubing scanner 150 reaching and being processed by the computer 130 can be more or less than one foot. In this exemplary embodiment, the computer 130 can account for the delay and modify the current data received from the encoder 115 to overcome this delay and equate the depth with the position along the tubing 125 that the data was retrieved from.

In step 2135, the computer 130 associates sensor data point S with depth D. In one exemplary embodiment, the association is made by creating and inserting the associated data into data tables which can later be used to generate the analysis data chart and the overlying depth chart. In step 2140, and inquiry is conducted by the computer 130 to determine if additional sensor data points S are being received from the tubing scanner 150. If so, the "YES" branch is followed to step 2145, where the counter variable S is incremented by one. In step 2150, the computer 130 receives the next sensor data point S and the process returns to step 2130 to determine the depth for that, sensor data point. Returning to step 2140, if no additional sensor data points are being received, the "NO" branch is followed to step 2155, where the computer 130 displays the received sensor data on a time or samples based chart. In step 2160, the computer 130 overlays the depth data associated with each sensor data point onto the analysis data chart. The process then continues to the END step.

Figure 22:
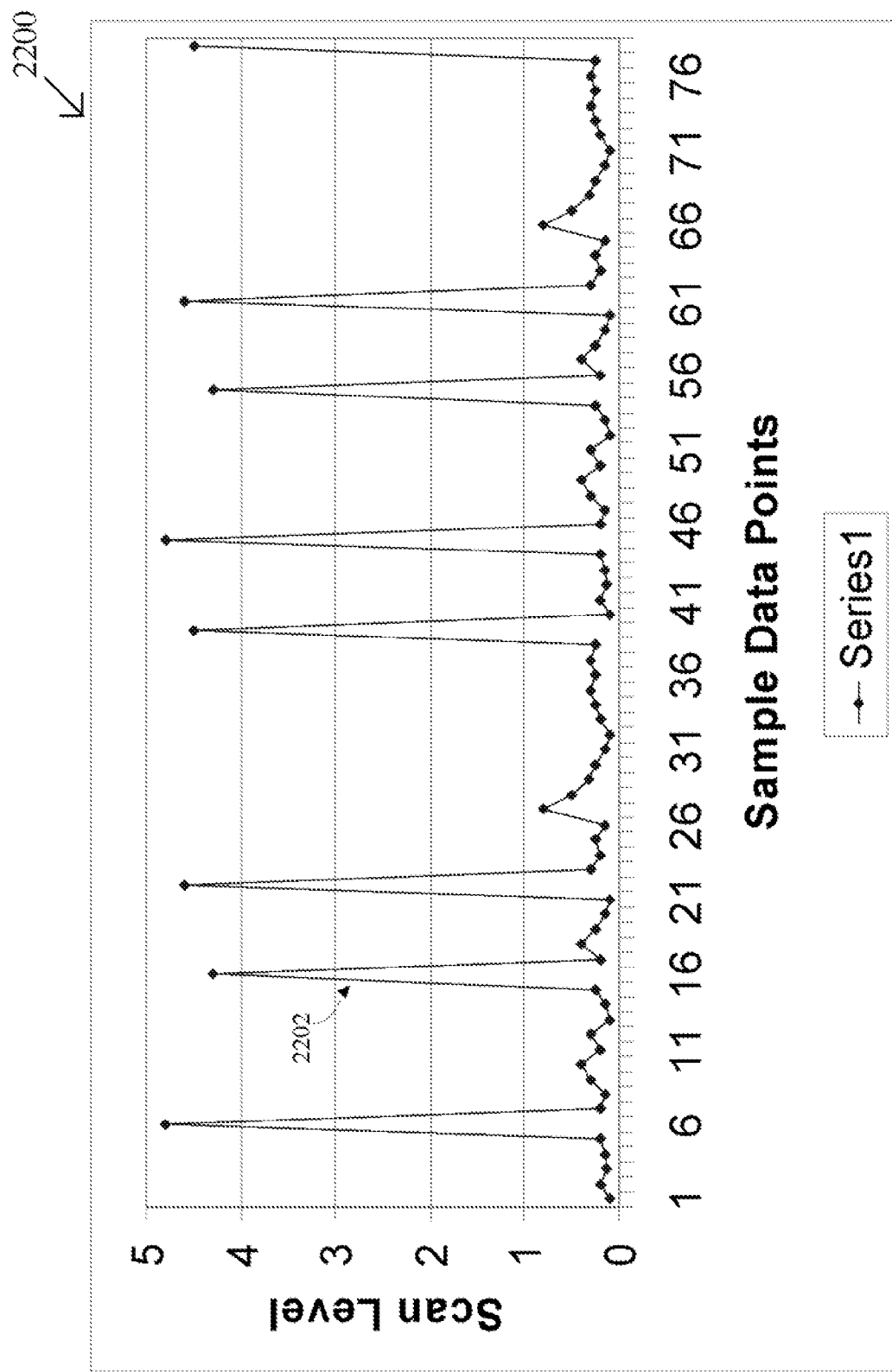
Figure 22A:
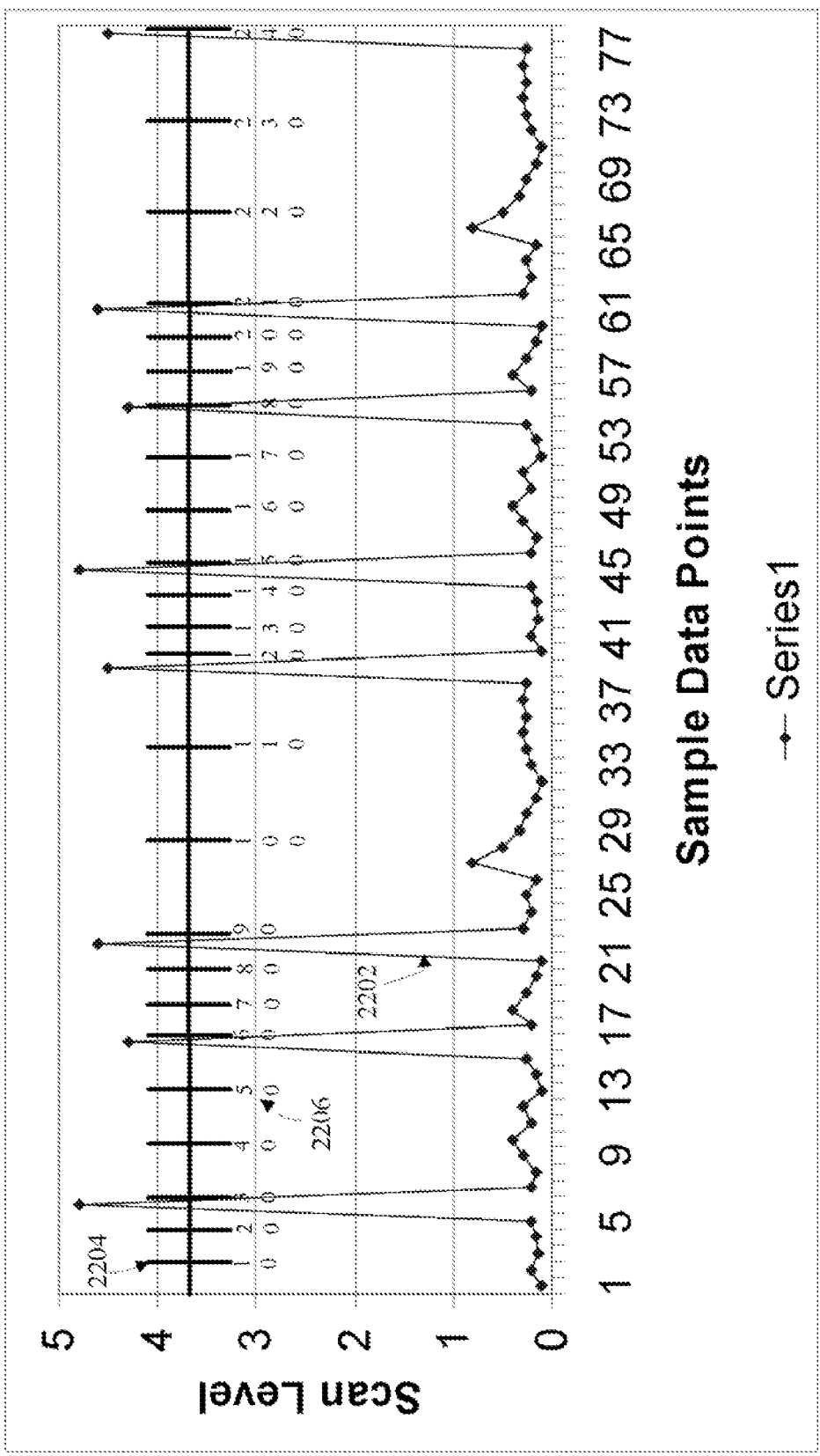

FIGS. 22, 22A, and 22B provide an exemplary view of steps 2135-2160 of FIG. 21. Now referring to FIGS. 22, 22A, and 22B, the exemplary data analysis display 900 of FIG. 22 includes a y-axis representing the scan level received from the sensors in the tubing scanner 150, an x-axis representing the sample count for the samples received from the tubing scanner 150, and analysis data 2202 that could be from any sensor in the tubing scanner 150. FIG. 22B provides an exemplary database table 2220 that includes a data sample counter 2222, designated "sensor data point counter S"; the scan level 2224 for each data point, designated "data value", a position or depth value counter 2226, designated "position counter (D)"; and the depth as received by the computer 130 from the encoder display, in feet. The exemplary database table 2220 provides only one of numerous ways to associate the depth data from the encoder display to the scan data points as described in FIG. 21.

FIG. 22A provides an exemplary data analysis display 2210 that includes the y-axis representing the scan level received from the sensors in the tubing scanner 150, the x-axis representing the sample count for the samples received from the tubing scanner 150, and analysis data 2202, shown as a line graph of data points, that could be from any sensor in the tubing scanner 150 from exemplary display 200 of FIG. 22. Exemplary display 2210 further includes an overlying depth axis 2204. The position of the depth axis 2204 can be easily modified in other exemplary embodiments. Furthermore, the display as a whole could be positioned vertically instead of horizontally as shown in exemplary displays 2200 and 2210. The exemplary depth axis 2204 is achieved by retrieving the associated depth data 2228 for each data point 2224 in the database table 2220 and scaling the depth axis 2204 to equal the position of each data point. Those of ordinary skill in the art will recognize that the novelty of displaying the depth data associated with each data point can be achieved in many other ways without falling outside the scope of this invention. Furthermore, those of skill in the art will recognize that the detail provided in the depth axis 2204 is easily adjustable based on the preferences of the oilfield service operator and the amount of detail needed to assist the oilfield service operators in making decisions about the well 175.

Figure 23:
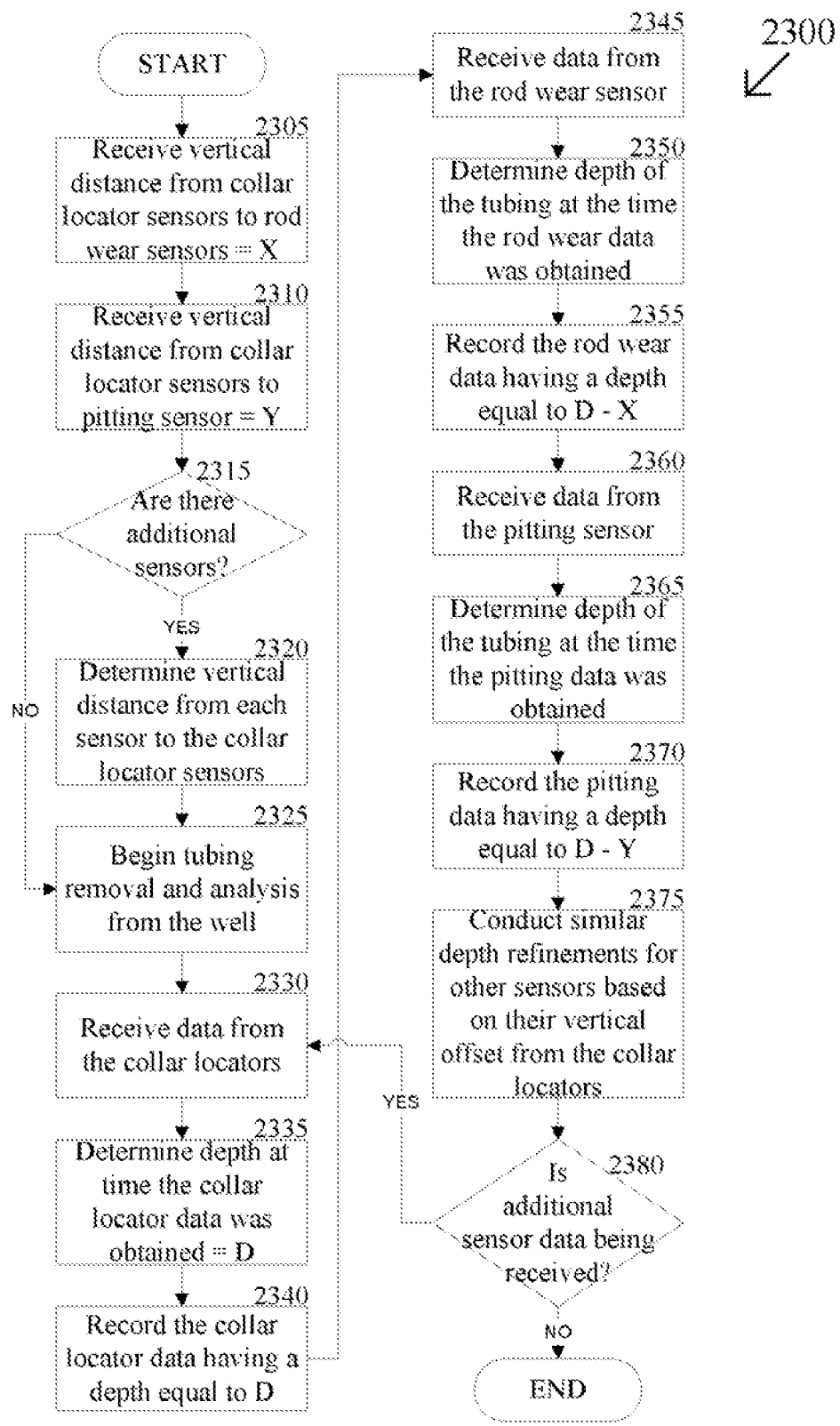
FIG. 23 is a flowchart diagram of an exemplary method for calibrating the tubing data received from several sensors to a specific depth in accordance with one exemplary embodiment of the present invention.

FIG. 23 is a logical flowchart diagram illustrating an exemplary method 1000 for calibrating the tubing data received from several sensors to a specific depth within the exemplary operating environment of the workover rig 140 of FIG. 1 and the tubing scanner 150 of FIG. 2, Referencing FIGS. 1, 2, and 23, the exemplary method 2300 begins at the START step and proceeds to step 2305, where the computer 130 receives the vertical distance from the collar locator 292 to the rod wear sensors 205, that distance being represented by the variable X. In step 2310, the computer 130 receives the vertical distance from the collar locator 292 to the pitting sensor 255 and represents that distance with variable Y. In one exemplary embodiment, the collar locators 292 are considered the base point for all depth positions, however those of ordinary skill in the art could designate other sensors or other points within or outside of the tubing scanner 150 to be the base reference for depth.

In step 2315, an inquiry is made to determine if there are additional sensors. The additional sensors may be located in or outside the tubing scanner 150 and may evaluate a range of information related to tubing 125 and well 175, including weight sensors, known to those of skill in the art. If there are additional sensors, the "YES" branch is followed to step 2320, where a vertical distance from each sensor to the collar locator 292 is determined and received by or input into a computer 130. Otherwise, the "NO" branch is followed to step 2325. In step 2325, the rig 140 begins the tubing 125 removal process.

The computer 130 or other analysis device receives data from the collar locators 292 in step 2330. In step 2335, the depth of the tubing 125 at the time the collar locator data was obtained is determined. This depth is recorded as variable D. The depth is not the depth of the tubing at the time it passes the collar locators. Instead, the depth is an estimate of the depth at which that portion of tubing 125 is located in the well 175 during the well's operation. The depth can be determined from the encoder 115 or other depth of positional sensors known to those of skill in the art. In step 2340, the computer 130 records the collar locator data as having a depth equal to D. The depth can be recorded in a database table or on a chart displaying real-time data for analysis by an oilfield service operator, or it can be recorded in another manner known to those of ordinary skill in the art. For instance, the data may be directly inserted into a spreadsheet.

In step 2345, the computer 130 receives data from the rod wear sensor 205. In step 2350, the depth of the tubing 125 at the time the rod wear data was obtained is determined. This depth is recorded as variable D. In step 2355, the computer 130 records the rod wear data as having a depth equal to D minus X. In step 2360, the computer 130 receives data from the pitting sensor 255. In step 2365, the depth of the tubing 125 at the time the pitting sensor data was obtained is determined. This depth is recorded as variable D. In step 2370, the computer 130 records the pitting sensor data as having a depth equal to D minus Y. Those of ordinary skill in the art will recognize that the depth variance to the base depth reference could be positive or negative based on relative position to the base reference and for that reason the computer 130 could also add the variance to the determined depth D if the relational position of the sensor to the base reference required it.

In step 2375, the system conducts similar depth refinements for other sensors based on vertical offset from the collar locators 292. In step 2380, an inquiry is made to determine if additional sensor data is being received. If so, the "YES" branch is followed to step 2330. Otherwise, the "NO" branch is followed to the END step.

Figure 24:
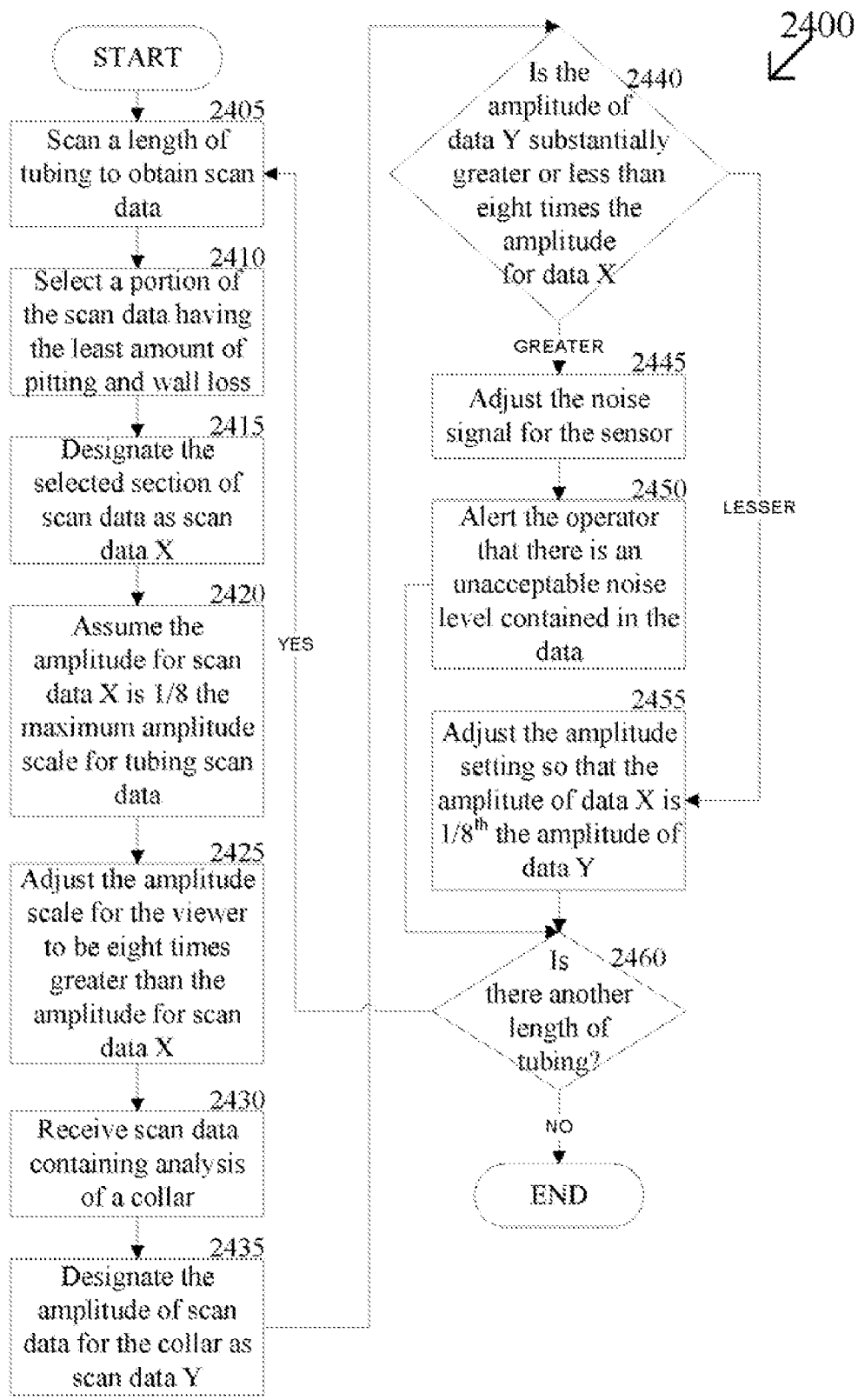
FIG. 24 is a flowchart diagram of an exemplary method for calibrating the amplitude of the tubing data received from the sensors in accordance with one exemplary embodiment of the present invention.

FIG. 24 is a logical flowchart diagram illustrating an exemplary method 2400 for calibrating the amplitude of the tubing data received from several sensors within the exemplary operating environment of the work over rig 140 of FIG. 1 and the tubing scanner 150 of FIG. 2. Referencing FIGS. 1, 2, and 24, the exemplary method 2400 begins at the START step and proceeds to step 2405, where the tubing scanner 150 scans a length of tubing 125 to obtain scan data. This scan data can be transmitted to the computer 130 or other analysis device, in one exemplary embodiment. In step 2410, the computer 130 evaluates the scan data for the piece of tubing 125 and selects a portion of the scan data having the least amount of pitting and wall loss. In one exemplary embodiment, the computer 130 selects data representing a five foot length of tubing 125. The selection of the scan data having the least amount of pitting can be accomplished by selecting the data having the smallest maximum peak amplitude, selecting the data having the smaller average amplitude or other analysis methods known to those of skill in the art.

The computer 130 designates the selected section of data as "scan data X" in step 2415. In step 2420, an assumption is input or programmed into the computer 130 regarding the ratio of the amplitude for scan data X to the amplitude of scan data for the entire length of tubing. In one exemplary embodiment, the programmed ratio is scan data X having approximately one-eighth the amplitude of the scale for the chart used to view the scan data and analyze the tubing 125. In step 2425, the amplitude scale for the viewable portion of the chart for each sensor displayed on the computer 130 or other display device is set equal to eight times the amplitude for scan data X.

In step 2430, the computer 130 receives scan data from one or more of the sensors containing analysis of a collar 157. In one exemplary embodiment, the collar portion has been noted as significant because it often generates the strongest signal for many of the sensors. However, those of ordinary skill in the art will recognize that other objects may generate the strongest signal for a sensor an those objects could be used as the measuring point discussed in the following steps. The computer 130 designates the amplitude of scan data for the collar 157 as scan data Y. In step 2440, an inquiry is conducted to determine if the amplitude of scan data Y is substantially greater than or less than the amplitude for scan data X. The variance from substantially lesser or greater to exactly equal to eight times the amount can be programmed into the computer 130 based on the current environmental conditions, the sensors being evaluated, and the type of tubing or other material being analyzed. If the amplitude is substantially greater, the "GREATER" branch is followed to step 2445, where the noise signal for the sensor is adjusted. In one exemplary embodiment, the noise signal is manually adjusted by an operator, however the signal could be automatically adjusted by the computer 130 or other control device. In step 2450, an alert is sent to the oilfield service operator that there is an unacceptable noise level contained in the data for at least one sensor. In one exemplary embodiment, this alert may include an audible signal, a visual signal (such as a flashing light), a message displayed on the computer 130 or other display device, an electronic page or electronic mad. The process then continues to step 2460.

Returning to step 2440, if the amplitude is substantially less, then the "LESSER" branch is followed to step 2455, where the amplitude setting for the data or chart display is adjusted to increase the level of the displayed sensor data in the viewable area of the display on the computer 130. In step 2460, an inquiry is conducted to determine if there is another length of tubing 125 than needs to be analyzed by tubing scanner 150. If so, the "YES" branch is followed to step 2405 to begin scanning the next length of tubing. Otherwise, the "NO" branch is followed to the END step. Those of ordinary skill in the art will recognize that the method described in FIG. 24 allows for continuous calibration of the tubing sensors and the display of the data from those sensors during the removal of tubing 125 from the well 175.

From the foregoing, it will be appreciated that an embodiment of the present, invention overcomes the limitations of the prior art. Those skilled in the art will appreciate that the present invention is not limited to any specifically discussed application and that the embodiments described herein are illustrative and not restrictive. From the description of the exemplary embodiments, equivalents of the elements shown therein will suggest themselves to those skilled in the art, and ways of constructing other embodiments of the present invention will suggest themselves to practitioners of the art. Therefore, the scope of the present invention is to be limited only by any claims that may follow.

The invention claimed is:

1. A method for interpreting tubing data comprising;
    scanning a plurality of tubing segments with a tubing scanner to produce tubing segment scan data, said scanner comprising a rod-wear sensor;
    correlating the segment scan data with positional data obtained from an encoder;
    analyzing the tubing segment scan data using pattern recognition software to identify wear patterns in the tubing segments, wherein the pattern recognition software employs Fourier transform processing; and
    displaying the tubing segment data.

2. The method of claim 1 wherein the tubing scanner further comprises a pitting sensor.

3. The method of claim 2 wherein the pattern recognition software flags regions having significant pitting without significant rod wear.

4. The method of claim 2 wherein the pattern recognition software flags regions having significant rod wear without significant pitting.

5. The method of claim 1 wherein the pattern recognition software processes the data based upon genetic algorithm, fractal mathematics, artificial intelligence, adaptive filtering, Kalman filtering, least squares analysis, partial least squares analysis, stochastic filtering, statistical pattern recognition, linear algorithm, or linear programming.

6. The method of claim 1 wherein the pattern recognition software flags wear features.

7. The method of claim 1 further comprising determining if a region of rod wear is attributable to stroke length of the sucker rod.

8. The method of claim 1 further comprising flagging the region of rod wear as being erroneous.

9. The method of claim 1 further comprising displaying the data as a function of depth.

10. A method for evaluating a tubing string comprising a plurality of tubing sections at a wellsite comprising a well, comprising the steps of:
    moving at least one tubing section into or out of the well;
    scanning the tubing section with at least one sensor to receive a plurality of wear data and a plurality of pitting data as at least a portion of the tubing section is being moved into or out of the well;
    displaying the wear data and the pitting data on a visual display; and
    analyzing the plurality of wear data and pitting data.

11. The method of claim 10, wherein the step of analyzing the wear data and pitting data comprises:
    receiving depth data for the tubing string as the at least one tubing section is being moved into or out of the well;
    correlating the wear data with corresponding depth data to comprise a wear log for the tubing string;
    correlating the pitting data with corresponding depth data to comprise a pitting log for the tubing string; and
    comparing the wear log and the pitting log for the at least one tubing section.

12. The method of claim 11, further comprising the steps of:
    identifying an indication of excessive wear on the wear log;
    determining that the indication of excessive wear does not reoccur on the wear log at a substantially regular depth interval; and
    generating a visual indicator identifying the excessive wear feature as being potentially erroneous on the display adjacent to the indication of the excessive wear feature.

13. The method of claim 11, further comprising the steps of:
    determining that the pitting log reveals significant pitting of the tubing section at a first depth;
    determining that the wear log does not reveal significant wear of the tubing section at the first depth; and
    generating a visual indicator on the display comprising an identification of a chemical issue at the first depth for the tubing section.

14. The method of claim 13, further comprising the step of generating a notification to schedule a chemical treatment for the well.

15. The method of claim 11, further comprising the steps of:
    determining that the wear log reveals significant wear of the tubing section at a first depth;
    determining that the pitting log does not reveal significant pitting of the tubing section at the first depth; and
    generating a visual indicator on the display adjacent to an indication of the first depth of the wear log comprising a notification that the wear log data revealing significant wear at the first depth is potentially erroneous.

16. The method of claim 15, wherein the visual indicator composes highlighting the wear data at the first depth.

17. The method of claim 15, wherein the visual indicator composes a comment presented adjacent the wear log at the first depth.

18. The method of claim 11, further comprising the steps of:
    determining that the wear log reveals a length of significant wear extending along a length of the tubing string at a first depth;
    determining that the length of significant wear is less than a predetermined length; and
    generating a visual indicator on the display adjacent to the display of the length of significant wear on the wear log at the first depth.

19. The method of claim 18, wherein the visual indicator composes a notification that the display of the length of significant wear on the wear log is potentially erroneous.

20. The method of claim 18, wherein the predetermined length is a stroke length for a sucker rod at the well.

21. The method of claim 11, further comprising the steps of:
    determining that the wear log reveals significant wear of the tubing string at a first depth;
    determining that the pitting log reveals significant pitting of the tubing string at the first depth;
    determining if there is a dogleg in the well at the first depth; and
    generating a visual indicator of a dogleg on the display at the indication of the first depth on the display based on a positive determination that there is a dogleg in the well at the first depth.

22. The method of claim 11, further comprising the steps of:
- determining at a first depth that the wear log reveals high wear of the tubing string and the pitting log reveals high pitting of the tubing string;
- determining at a second depth that the wear log reveals low wear on the tubing string and the pitting log reveals low pitting on the tubing string;
- determining at a third depth that the wear log reveals high wear of the tubing string and the pitting log reveals high pitting of the tubing string;
- wherein the second depth is between the first depth and the third depth; and
- generating a visual indicator of a harmonic condition.

23. The method of claim 10, wherein the wear data and the pitting data are presented on a common depth axis on the display.

24. The method of claim 10 further comprising the steps of:
- generating a confidence plot comprising an indication of a reliability of each feature presented on at least one of the wear log and the pitting log; and
- presenting the confidence plot with the wear data and the pitting data on a common depth axis on the display.

25. The method of claim 10 further comprising the step of receiving a quality grade for the tubing section.

26. The method of claim 25, wherein the quality grade is received from a manual input by an operator.

27. A method for evaluating a tubing string comprising a plurality of tubing sections at a wellsite comprising a well, comprising the steps of:
- moving at least one tubing section into or out of the well;
- scanning the tubing section with at least one sensor to receive a plurality of wear data and a plurality of pitting data as at least a portion of the tubing section is being moved into or out of the well;
- receiving depth data for the tubing string as the at least one tubing section is being moved into or out of the well;
- correlating the wear data with the corresponding depth data to comprise a wear log;
- correlating the pitting data with the corresponding depth data to comprise a pitting log;
- displaying the wear log and the pitting log on a common depth axis on a visual display; and
- analyzing the wear log and the pitting log with a pattern recognition software to identify wear patterns in the tubing string.

* * * * *